(12) United States Patent
Mirza

(10) Patent No.: US 12,268,407 B2
(45) Date of Patent: Apr. 8, 2025

(54) ENDOSCOPIC SURGICAL INSTRUMENT HAVING A RETRACTABLE CUTTING BLADE AND SURGICAL PROCEDURE USING SAME

(71) Applicant: A.M. SURGICAL, INC., Smithtown, NY (US)

(72) Inventor: Romi Mirza, Henderson, NV (US)

(73) Assignee: A.M. Surgical, Inc., Nashua, NH (US)

( * ) Notice: Subject to any disclaimer, the term of this patent is extended or adjusted under 35 U.S.C. 154(b) by 526 days.

(21) Appl. No.: 17/731,736

(22) Filed: Apr. 28, 2022

(65) Prior Publication Data

US 2022/0354526 A1 Nov. 10, 2022

Related U.S. Application Data

(63) Continuation-in-part of application No. 17/343,986, filed on Jun. 10, 2021, now Pat. No. 11,596,430.

(60) Provisional application No. 63/037,872, filed on Jun. 11, 2020.

(51) Int. Cl.
*A61B 17/32* (2006.01)
*A61B 17/00* (2006.01)

(52) U.S. Cl.
CPC ........... *A61B 17/320036* (2013.01); *A61B 2017/00367* (2013.01); *A61B 2017/00477* (2013.01)

(58) Field of Classification Search
CPC ...... A61B 17/320036; A61B 17/32002; A61B 17/320016; A61B 17/3205; A61B 2017/00367; A61B 2017/00477; A61B 2017/00907; A61B 2017/00862; A61B 2017/320032; A61B 2017/320064; A61B 2017/00353; A61B 2017/320008; A61B 90/361; A61B 2090/08021; A61B 1/00128; A61B 1/3132; A61B 1/00087; A61B 1/00135; A61B 1/018

See application file for complete search history.

(56) References Cited

U.S. PATENT DOCUMENTS

| | | | |
|---|---|---|---|
| 5,306,284 A * | 4/1994 | Agee | A61B 17/320036 606/170 |
| 5,366,465 A | 11/1994 | Mirza | 606/170 |
| 7,041,115 B2 | 5/2006 | Mirza et al. | 606/170 |
| 7,780,690 B2 * | 8/2010 | Rehnke | A61B 17/320036 606/167 |
| 8,821,383 B2 | 9/2014 | Mirza et al. | 600/114 |

(Continued)

*Primary Examiner* — Julian W Woo
*Assistant Examiner* — Osama Nemer
(74) *Attorney, Agent, or Firm* — Bodner & Bodner, PLLC; Gerald T. Bodner; Christian P. Bodner

(57) ABSTRACT

An endoscopic surgical instrument includes a front slide, a scope coupler mounted on the front slide, a hammer pivotally mounted on the front slide, a cannula having a lumen and formed with a slot, a sleeve mounted to partially rotate on a portion of the cannula, a blade tube and a retractable cutting blade assembly having a cutting blade situated within the blade tube. The blade tube extends axially from the front slide. The tube is received by the lumen of the cannula. The blade tube has a bore in which the distal end of an endoscope may be received. The instrument may be locked in one position to allow the tip of the endoscope to engage the blade assembly and cause the cutting blade to project from the cannula slot during a tissue cutting procedure, or may be locked in another position wherein the cutting blade remains retracted.

28 Claims, 57 Drawing Sheets

(56) References Cited

U.S. PATENT DOCUMENTS

| | | | |
|---|---|---|---|
| 8,911,470 B2 | 12/2014 | Mirza et al. | 606/204 |
| 8,979,880 B2 | 3/2015 | Mirza et al. | 606/170 |
| 8,992,424 B2 * | 3/2015 | Orbay | A61B 1/00052 |
| | | | 600/183 |
| 9,066,746 B2 | 6/2015 | Mirza et al. | |
| 9,179,930 B2 | 11/2015 | Mirza et al. | |
| 9,211,136 B1 | 12/2015 | Mirza et al. | |
| 9,408,623 B2 | 8/2016 | Mirza et al. | |
| 9,445,830 B2 | 9/2016 | Mirza et al. | |
| 9,610,089 B2 | 4/2017 | Mirza et al. | |
| 9,808,274 B2 | 11/2017 | Mirza et al. | |
| 9,931,133 B2 | 4/2018 | Mirza et al. | |
| 10,201,372 B2 | 2/2019 | Mirza et al. | |
| 10,265,093 B2 | 4/2019 | Mirza et al. | |
| 10,548,624 B2 | 2/2020 | Mirza et al. | |
| 11,051,848 B2 | 7/2021 | Mirza et al. | |
| 11,096,720 B2 | 8/2021 | Mirza et al. | |

\* cited by examiner

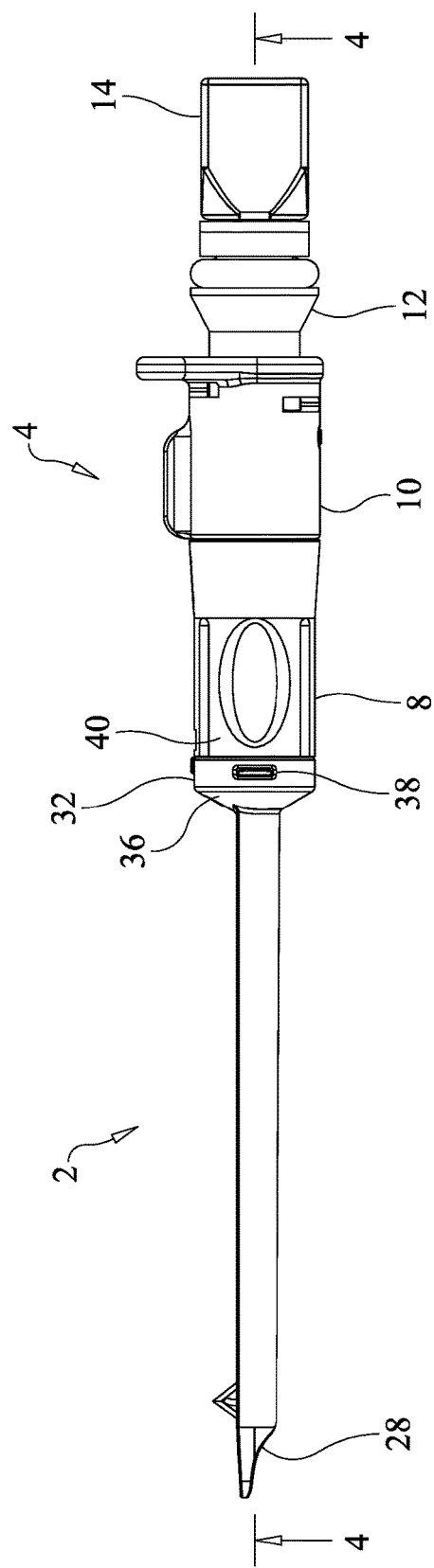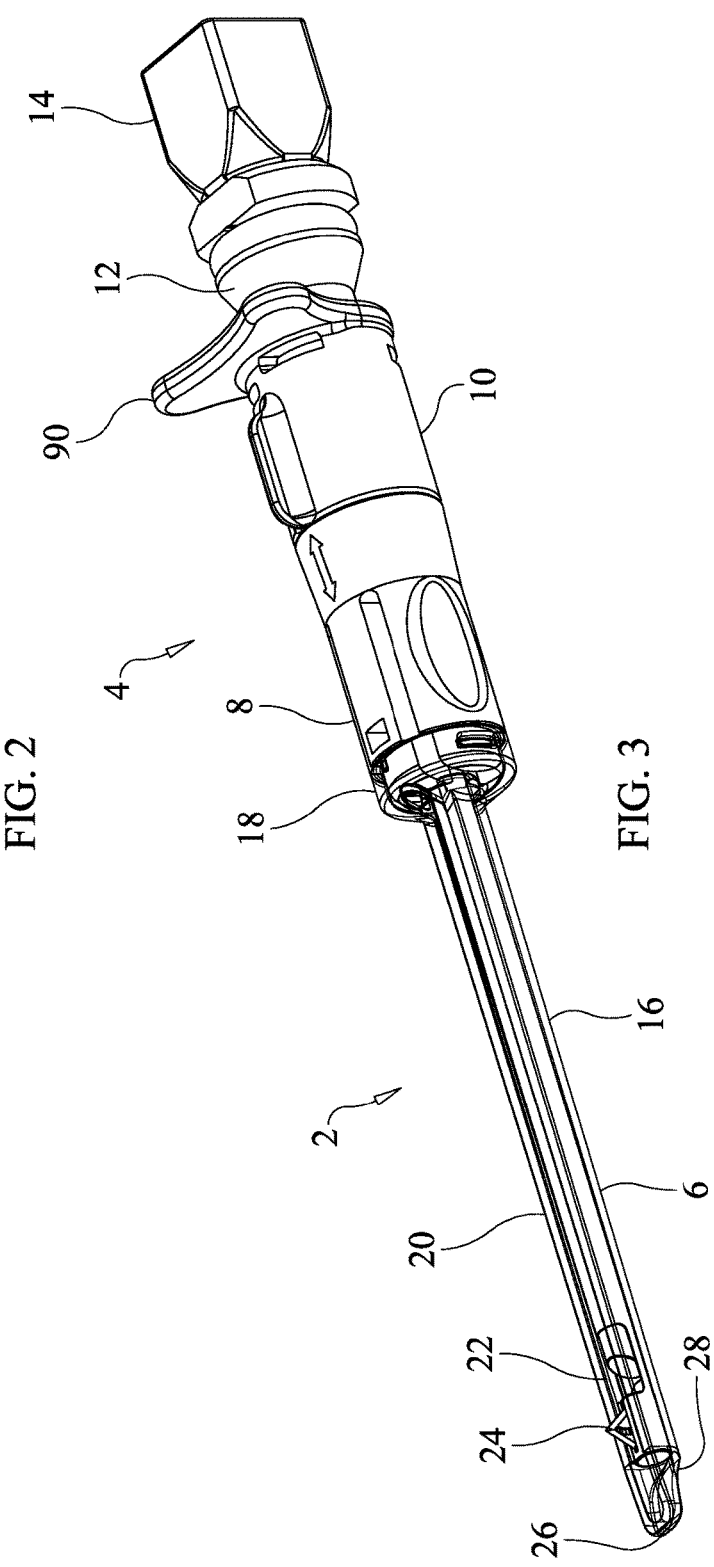

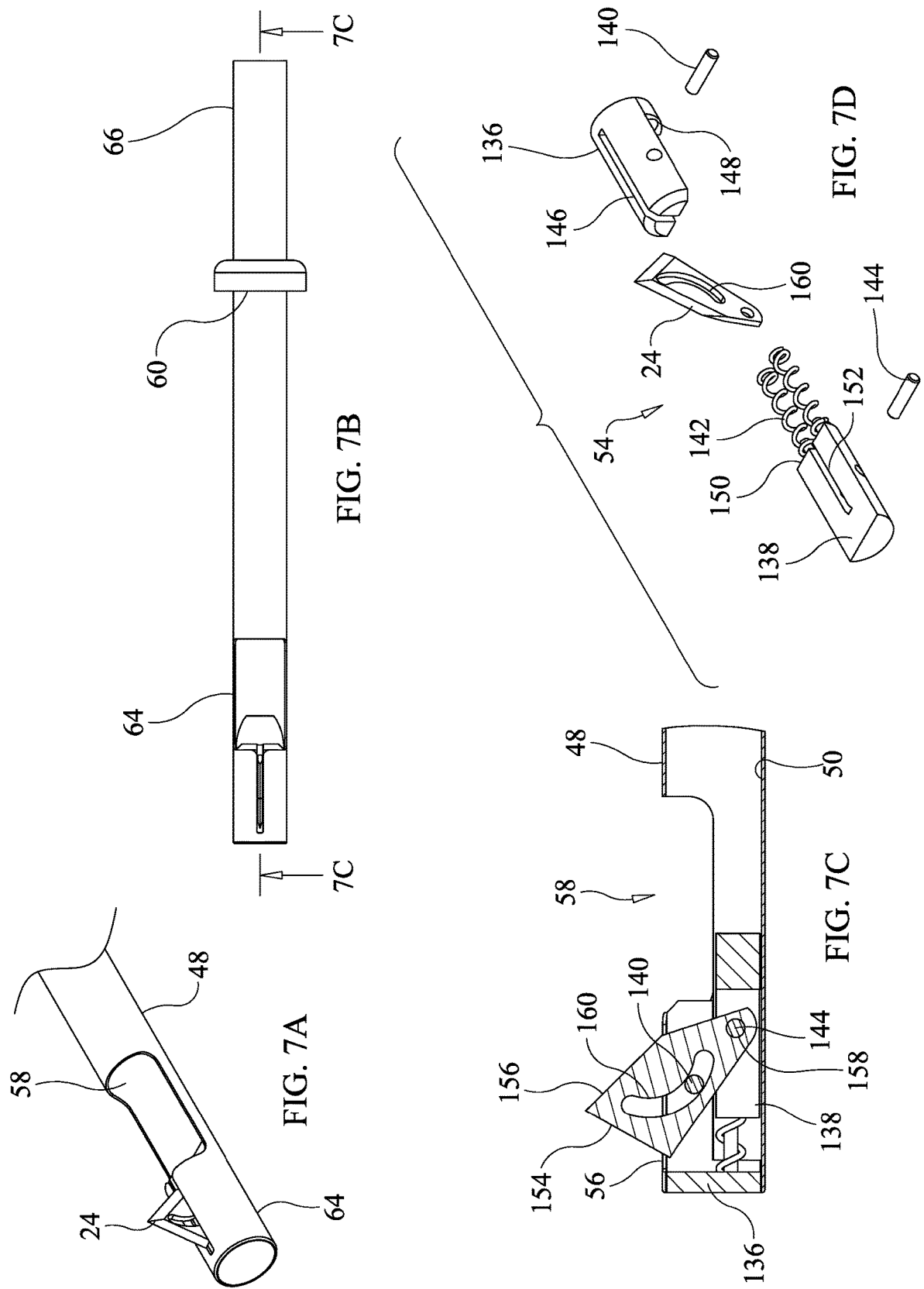

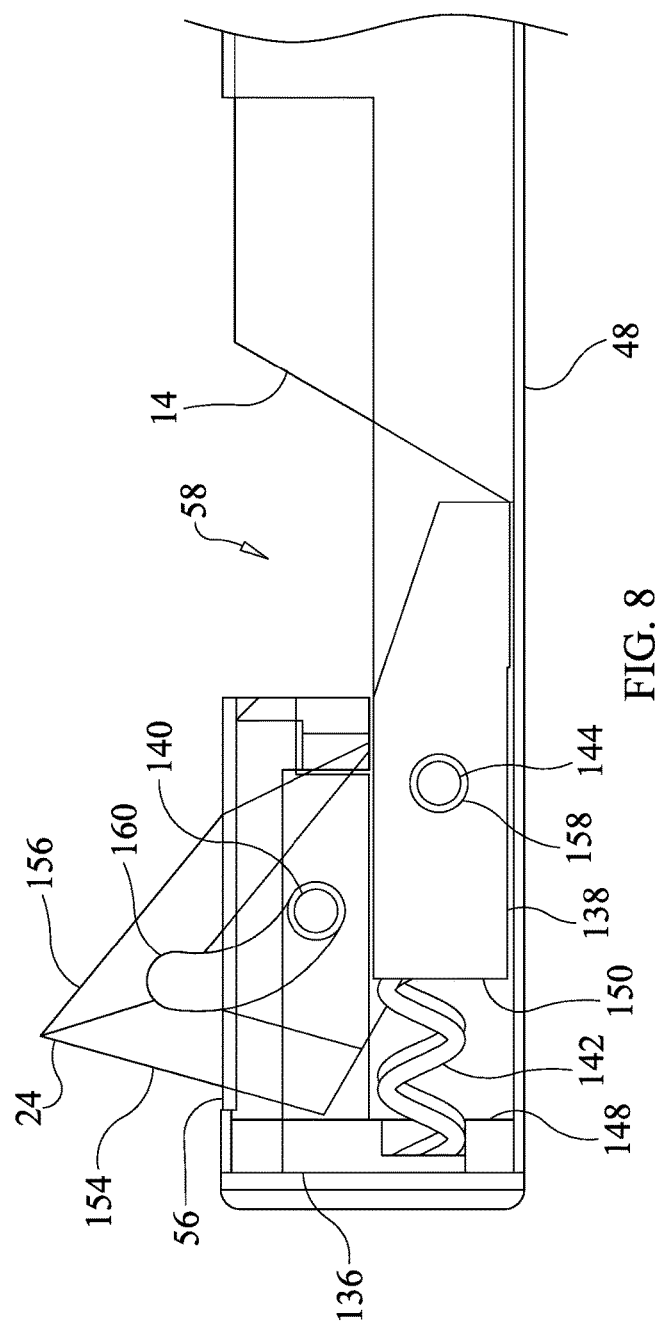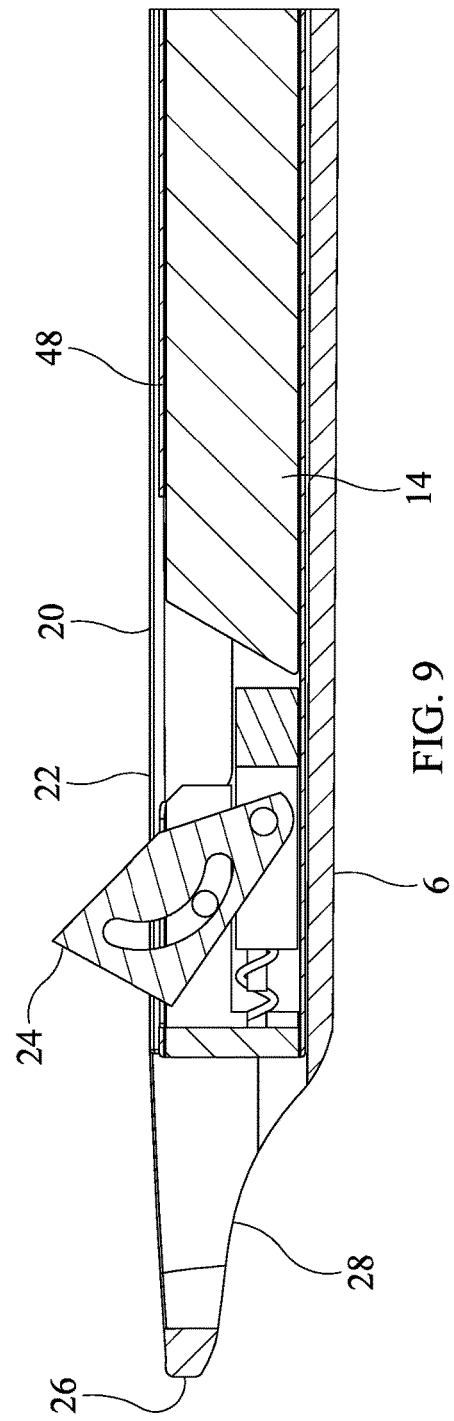

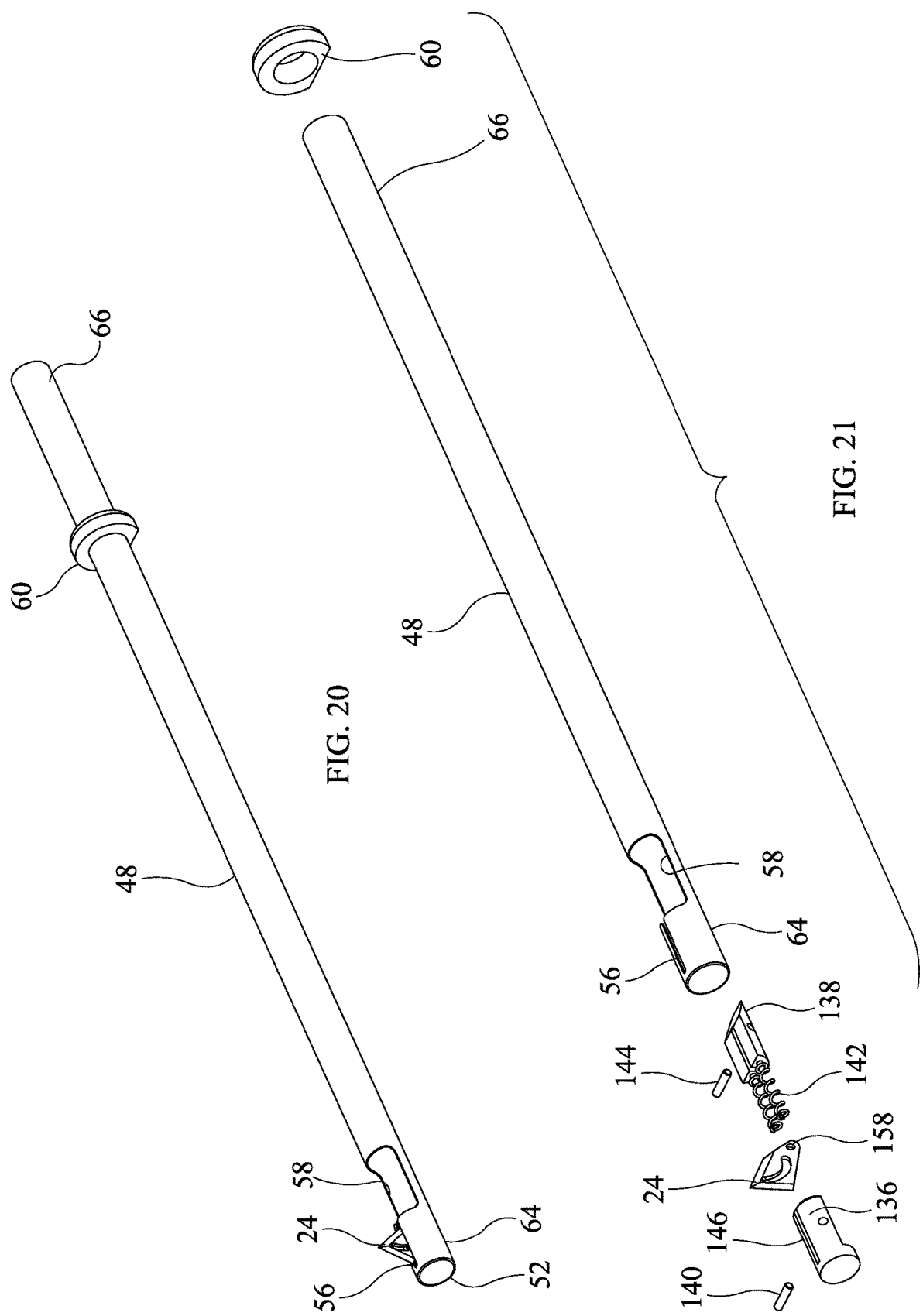

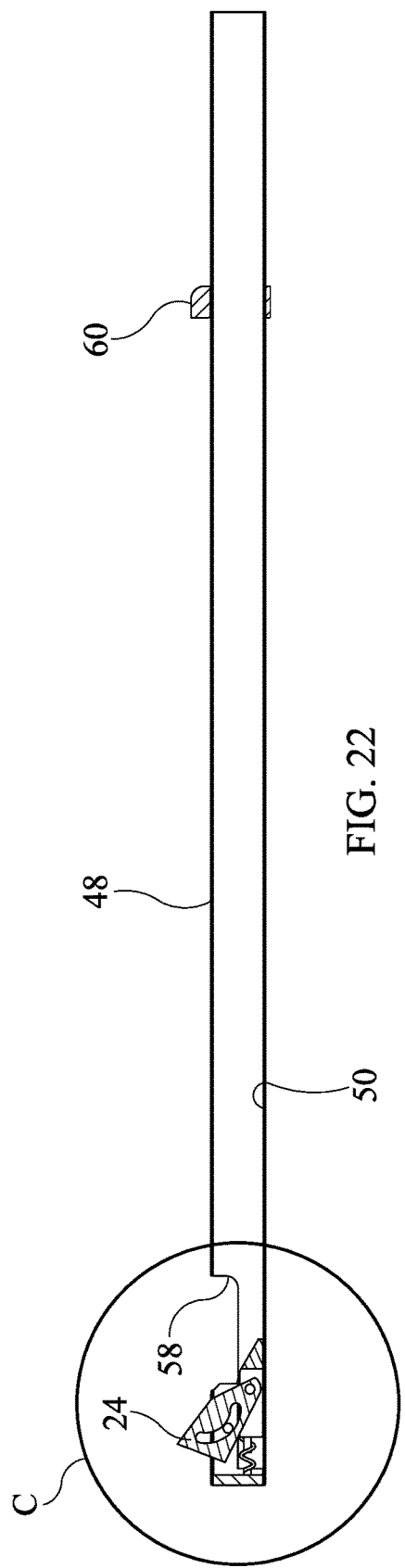
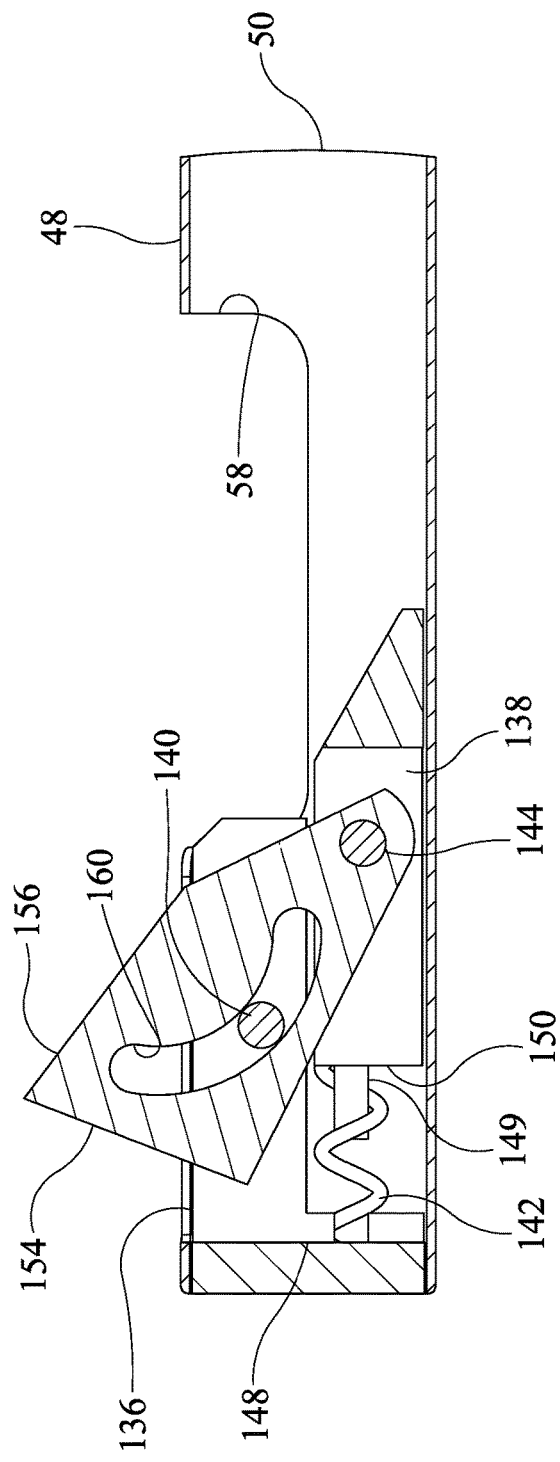

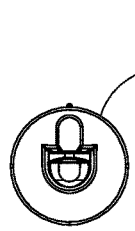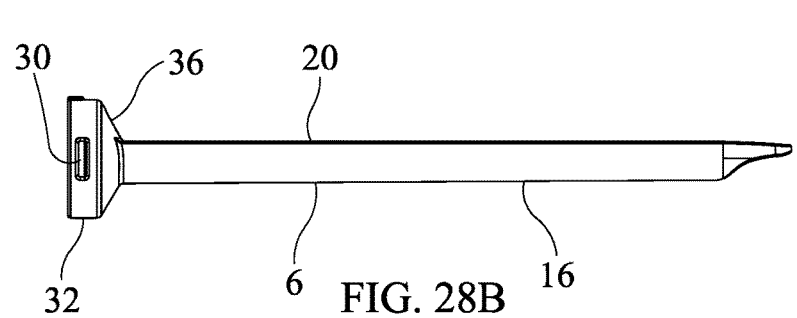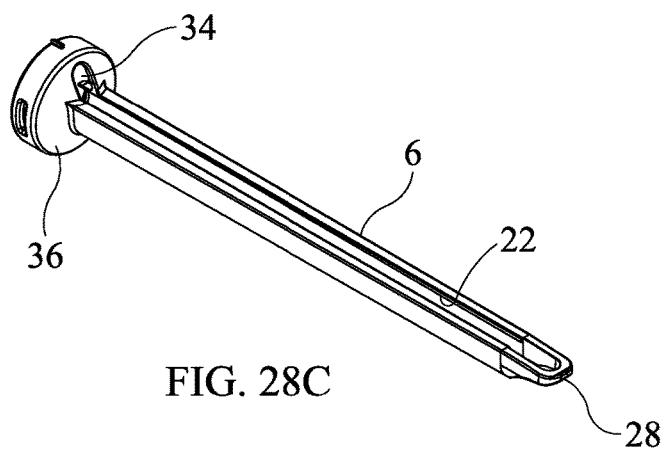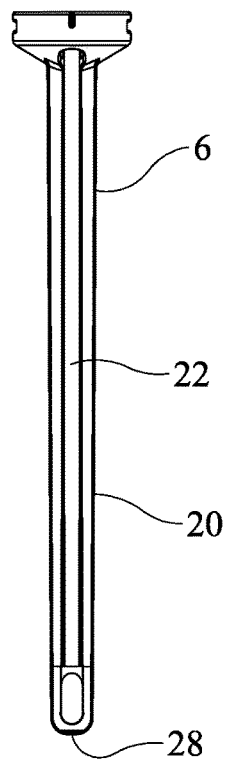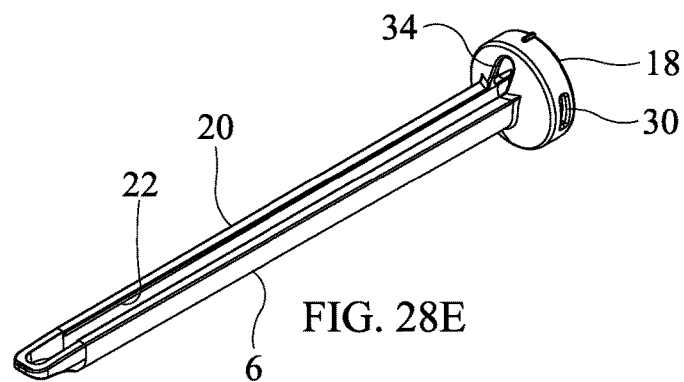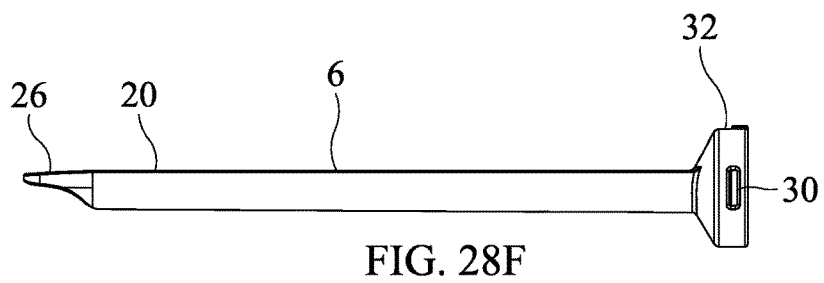
FIG. 28A
FIG. 28B
FIG. 28C
FIG. 28D
FIG. 28E
FIG. 28F

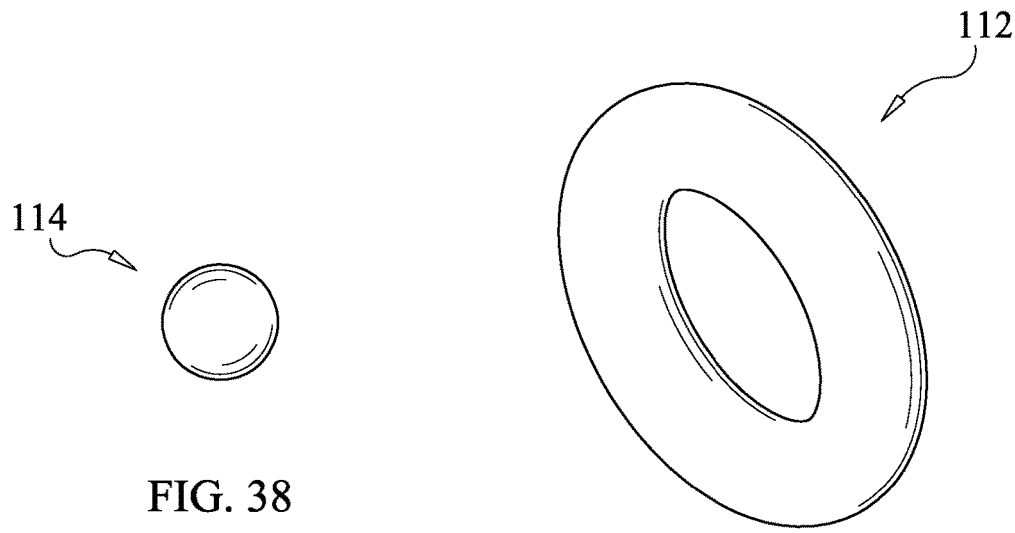
FIG. 38
FIG. 39
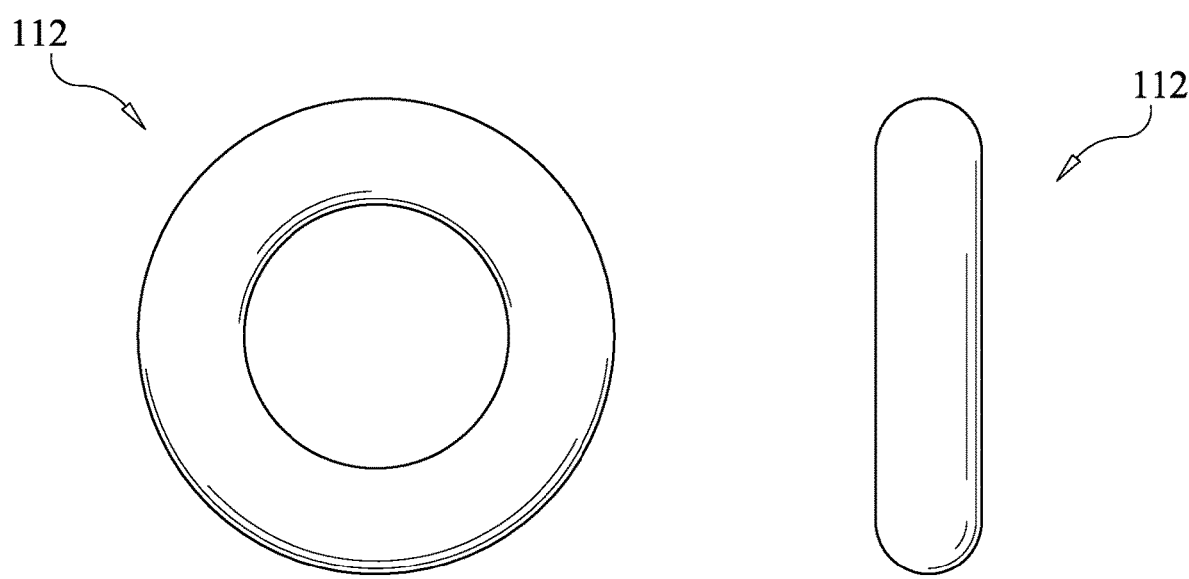
FIG. 40
FIG. 41

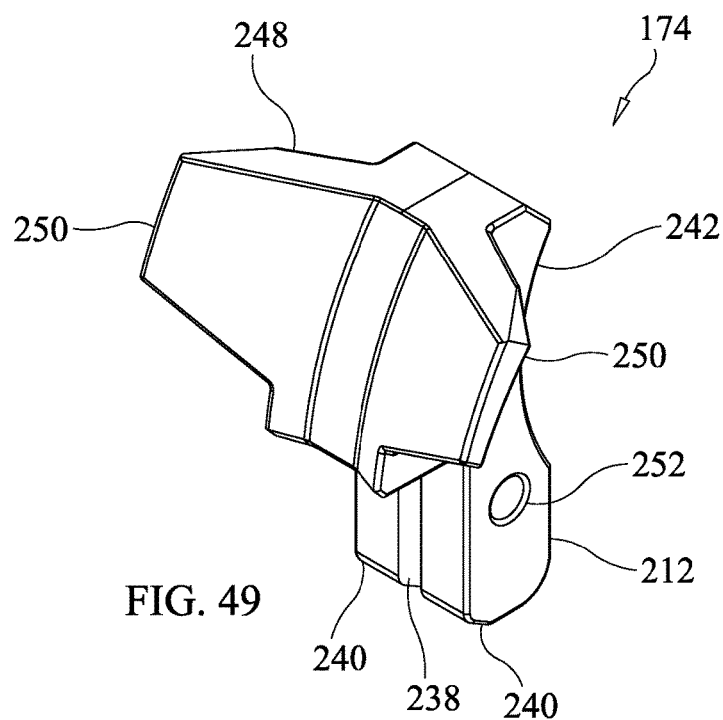
FIG. 49
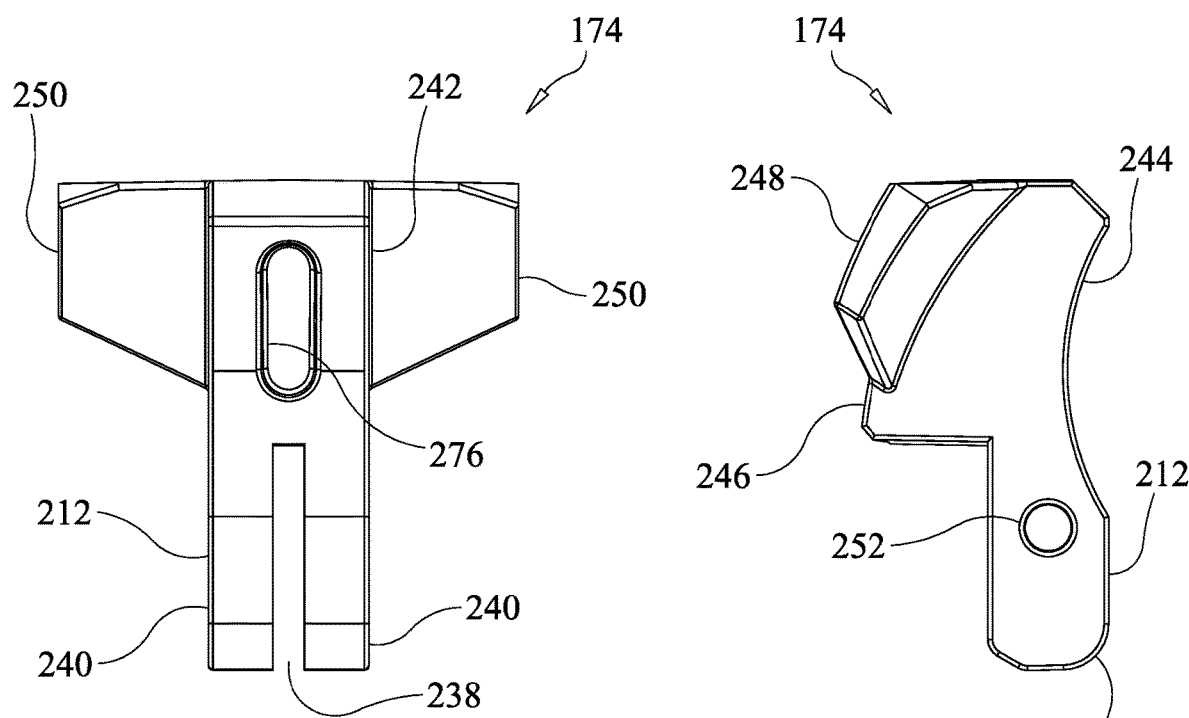
FIG. 50
FIG. 51

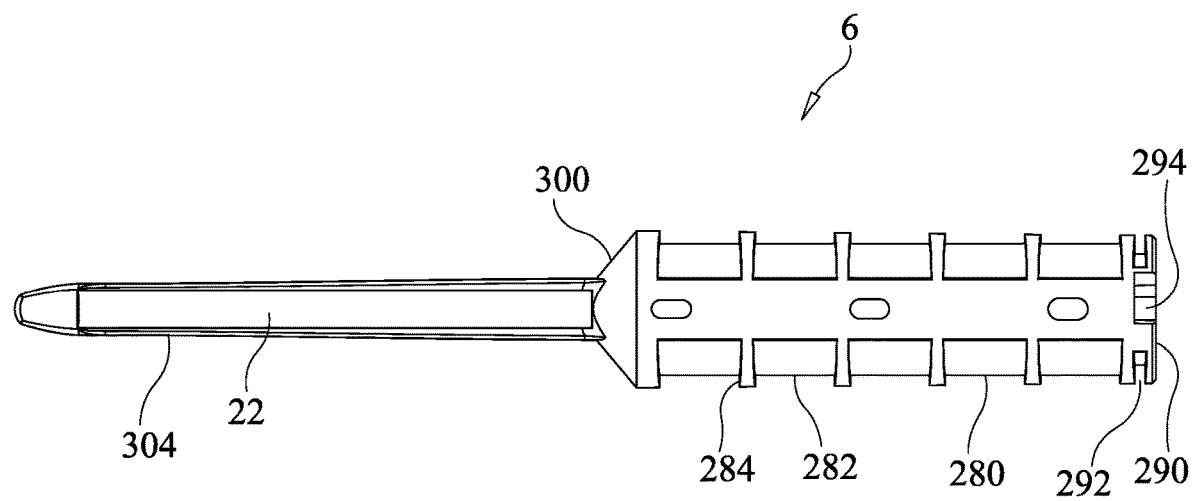
FIG. 62
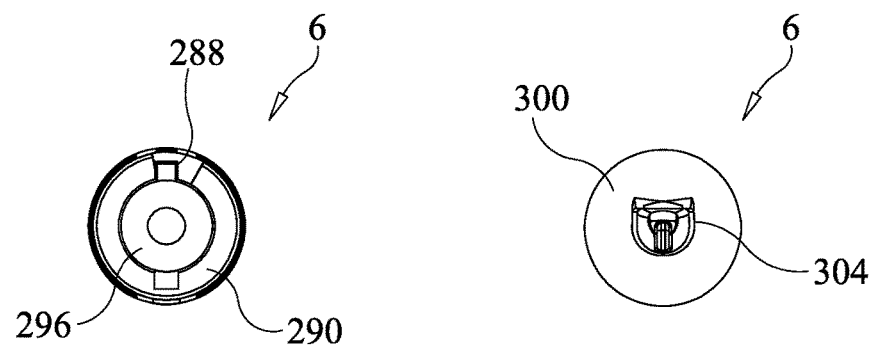
FIG. 63
FIG. 64

ENDOSCOPIC SURGICAL INSTRUMENT HAVING A RETRACTABLE CUTTING BLADE AND SURGICAL PROCEDURE USING SAME

CROSS-REFERENCE TO RELATED APPLICATIONS

This application is a continuation-in-part of co-pending U.S. patent application Ser. No. 17/343,986, filed on Jun. 10, 2021, and titled "Endoscopic Surgical Instrument Having a Retractable Cutting Blade and Surgical Procedure Using Same", which is related to U.S. Provisional Patent Application Ser. No. 63/037,872, filed on Jun. 11, 2020, and titled "Endoscopic Surgical Instrument Having a Retractable Cutting Blade and Surgical Procedure Using Same", the disclosure of each of which is hereby incorporated by reference and on each of which priority is hereby claimed.

BACKGROUND OF THE INVENTION

Field of the Invention

The present invention generally relates to medical devices, and more particularly relates to devices and methods for endoscopic surgery. Even more specifically, this invention relates to procedures and endoscopic surgical instruments used in carpal tunnel or pulley release surgery, or any soft tissue release surgery (e.g., cubital tunnel and gastroc releases).

Description of the Prior Art

Endoscopic surgery is a minimally invasive surgical procedure that is performed through small incisions or natural body openings. An endoscopic procedure typically involves use of specialized devices and remote-control manipulation of instruments with indirect observation of the surgical field through an endoscope or similar device. Comparing to open surgery, endoscopic surgery may result in shorter hospital stays, or allow outpatient treatment.

Carpal tunnel syndrome is an entrapment median neuropathy resulting from compression of the median nerve at the wrist in the carpal tunnel. Symptoms of carpal tunnel syndrome include tingling, numbness, weakness, or pain felt in the fingers supplied by the median nerve or in the palm. Repetitive tasks, force, posture, and vibration have been cited as causative or contributing factors to carpal tunnel syndrome. Palliative treatments for carpal tunnel syndrome include direct corticosteroid injections, splinting, oral corticosteroids and/or behavior modification.

Typically, endoscopic surgery has involved a number of steps and separate devices for performing tendon, pulley or tunnel division. After making an incision and opening a path to the pulley or tunnel using a blunt instrument, a cannula is inserted into the path. Briefly, in order to smoothly insert the cannula, the central lumen of the cannula must be filled with a device, such as an obturator. The obturator is then removed and an endoscope, or arthroscope, is inserted into the cannula to view the pulley or tunnel. The endoscope is then withdrawn from the cannula, a knife is either advanced into the cannula for division or a specialized knife assembly is affixed to the endoscope and the knife/endoscope assembly is advanced into the cannula for division.

A.M. Surgical, Inc., the applicant herein, has developed and patented numerous compact surgical instruments for uniportal endoscopic pulley or tunnel release surgery that eliminate the need for a separate device, such as an obturator, for filling the cannula during insertion and eliminate the need to remove the endoscope in order to insert a cutting blade or blade assembly. Such instruments have revolutionized and simplified carpal tunnel surgical procedures, in particular, and many other surgical procedures, in general (for example, uniportal plantar fascia release, lateral release for patella realignment, release of the posterior and other compartments of the leg, and forearm fascia release for fascial compartment syndrome, and other endoscopic surgical divisions or partial separation of a tendon or ligament, cutting, dividing, separating or making an incision in connective tissue, muscle, cartilage, membranes, skin, other body tissues or organs, and other procedures).

One such endoscopic surgical instrument is disclosed in U.S. Pat. No. 8,911,470 (Mirza et al.), assigned of record to A.M. Surgical, Inc., the disclosure of which is incorporated herein by reference. The instrument includes a slotted clear (transparent) cannula, a cutting blade and a housing to which the slotted cannula is attached. The blade is "parked" within the instrument housing in a revolver assembly until deployed. The revolver assembly may be rotated to position the cutting blade in alignment with the cannula and, by doing so, the blade mounts to the distal end of a guidance tube passing through the housing and the revolver assembly. The guidance tube, with the cutting blade affixed to the end thereof, is advanced on the housing through the lumen of the cannula. The cutting blade protrudes through the cannula slot as it advances thereon from the proximate end to the distal end thereof such that any tissue or ligaments exposed to the cutting blade during a surgical procedure will be cut or severed. Other patents disclosing compact endoscopic surgical instruments that are assigned of record to A.M. Surgical include U.S. Pat. Nos. 8,979,880; 9,066,746; 9,179, 930; 9,211,136; 9,408,623; 9,445,830; 9,610,089; 9,808, 274; 9,931,133; 10,265,093; and 10,548,624, the disclosure of each of which is incorporated herein by reference.

The surgical instruments disclosed in the aforementioned patents work fine for their intended purpose, but each of these instruments has its cutting blade always protruding through the cannula slot when moved into the cannula. Thus, during a surgical procedure, when the cannula is properly positioned at the surgical site, any tissue or ligament in proximity to the cannula will be exposed to the cutting blade and will be cut or severed as the blade is advanced or retracted on the cannula.

OBJECTS AND SUMMARY OF THE INVENTION

It is an object of the present invention to provide an endoscopic surgical instrument having a retractable cutting blade.

It is another object of the present invention to provide an endoscopic surgical instrument having a retractable cutting blade sharpened at both edges which can perform an antegrade (forward) and retrograde (reverse) cut at the choice of the user.

It is a further object of the present invention to provide an endoscopic surgical instrument having a cannula formed with an axially-extending slot from which a cutting blade may be selectively caused to protrude or be retracted into the cannula at a selected position along at least a portion of the cannula.

It is still another object of the present invention to provide an endoscopic surgical instrument having a cannula with an axially-extending slot formed thereon, and which further includes a locking mechanism which prevents an endoscope or other tubular member inserted in the cannula from causing the blade to project from the cannula slot inadvertently.

It is a further object of the present invention to provide an endoscopic surgical instrument having a spring-biased blade situated in a tube that is received in the lumen of a slotted cannula, the blade being biased by the spring to be in a retracted state within the tube and selectively positionable in a projected state in which the blade protrudes from the tube and the slotted cannula when a force is applied thereto against the bias of the spring.

It is yet a further object of the present invention to provide an endoscopic surgical instrument having a retractable cutting blade and a cannula formed with an axially-extending slot from which the blade may be selectably caused to project, and which the instrument cooperates with an endoscope or arthroscope.

It is another object of the present invention to provide a surgical instrument which is attachable to an endoscope or arthroscope and having a retractable cutting blade, and which may be easily manipulated by a surgeon during a surgical procedure and used either for viewing the surgical site with the endoscope and with the blade retracted or for viewing with the endoscope while simultaneously cutting tissue with the retractable blade at the surgical site.

It is yet another object of the present invention to provide a surgical procedure using the endoscopic surgical instrument of the present invention.

In accordance with one form of the present invention, an endoscopic surgical instrument includes a main body assembly composed of several sections, and a cannula which is selectively attachable to and detachable from the main body assembly, the cannula having a bore or lumen extending axially therethrough, and an axially-extending slot formed thereon, the slot being in communication with the internal lumen of the cannula.

A tube, which houses a spring-biased retractable cutting blade assembly, is mounted on one end of the main body assembly and extends axially therefrom. The tube is receivable within the lumen of the cannula, and may be particularly oriented within the cannula lumen such that the cutting blade may be caused to project not only from the tube but also through the slot of the cannula, when such is desired by a surgeon during a surgical procedure. The inner tube has an axially-extending bore in which an endoscope or arthroscope may be received. The instrument, when mounted on the endoscope or arthroscope, may be locked in one position by a surgeon during a surgical procedure to allow the distal end of the endoscope to engage the blade assembly and cause the cutting blade to project from the inner tube and slot of the cannula during a tissue cutting procedure, or may be locked in another position to prevent the distal end of the endoscope from engaging the blade assembly so that the cutting blade remains retracted within the inner tube and without projecting therefrom or the slotted cannula.

In accordance with another form of the present invention, an endoscopic surgical instrument includes a front slide having a rear main body and an elongated, tubular member. The rear main body has an outer side wall defining a hammer receiving opening and an internal bore in communication with the hammer receiving opening. The main body further has a front wall joined to the outer side wall, the elongated, tubular member being joined to the main body at the front wall thereof and extending axially outwardly from the front wall. The elongated, tubular member has a bore extending axially therethrough, the bore of the elongated, tubular member being in communication with the internal bore of the rear main body.

The surgical instrument of this second form of the present invention further includes a scope coupler assembly, the scope coupler assembly including a scope coupler and having structure for removably mounting an endoscopic or arthroscope on the scope coupler. At least a portion of the scope coupler is received by the internal bore of the front slide such that the scope coupler is mounted on the rear main body of the front slide and is reciprocatingly movable within the internal bore of the rear main body.

The surgical instrument of this second form of the present invention also includes a hammer, the hammer being pivotally mounted on the rear main body of the front slide. The hammer has a main body, the hammer main body including an upper portion which extends outwardly of the rear main body of the front slide and through the hammer receiving opening formed therein, and a lower portion disposed opposite the upper portion and extending inwardly of the rear main body of the front slide and into the internal bore thereof. The hammer is pivotable on the rear main body of the front slide between a blade retracted position and a blade extended position, the lower portion of the hammer being engagable with the scope coupler such that the scope coupler is in a first, forward position on the front slide when the hammer is in the blade extended position and is in a second, rearward position on the front slide which is different from the first, forward position when the hammer is in the blade retracted position.

The surgical instrument in this alternative form additionally includes a cannula, the cannula having a generally cylindrical rear section and an elongated, slotted tubular member. The rear section of the cannula has an outer side wall defining an interior bore formed in the rear section, and a front wall having an opening formed through the thickness thereof, the slotted tubular member being joined to and extending outwardly from the front wall of the rear section of the cannula. The tubular member includes an outer side wall defining a lumen within the tubular member and has a slot formed through the thickness of the outer side wall in communication with the lumen. The slot extends at least partially along the axial length of the tubular member of the cannula. The lumen is in alignment and communication with the opening formed in the front wall of the rear section of the cannula. The cannula is mounted on the front slide such that the tubular member of the front slide is received by the interior bore of the rear section of the cannula.

There is also a sleeve in this second embodiment of the surgical instrument of the present invention. The sleeve is mounted on the rear section of the cannula and is at least partially rotatable thereon.

Additionally, this alternative form of the surgical instrument of the present invention has a blade tube, the blade tube having a proximal end portion and a distal end portion disposed axially opposite the proximal end portion. The proximal end portion is at least partially received by the bore of the tubular member of the front slide, and the distal end portion of the blade tube is received by the lumen of the tubular member of the cannula. The blade tube has formed therein a bore extending axially thereon and a blade slot formed thereon. The blade tube is positioned within the lumen of the tubular member of the cannula such that the blade slot is in alignment and communication with the axially-extending slot formed on the tubular member of the cannula.

Furthermore, like the earlier-described version, this alternative embodiment of the surgical instrument of the present invention has a retractable cutting blade assembly, the retractable cutting blade assembly being mounted in the internal axial bore of the blade tube in proximity to the distal end portion thereof. The retractable cutting blade assembly has a cutting blade, the cutting blade being positioned to be in alignment with the blade slot formed on the blade tube so as to selectively project outwardly from the blade tube through the blade slot of the blade tube and through the axially-extending slot formed in the tubular member of the cannula and to selectively retract into the bore of the blade tube.

The front slide and blade tube are configured to receive at least a distal viewing end portion of an endoscope or arthroscope such that the distal viewing end portion of the endoscope or arthroscope is selectively engagable with the retractable cutting blade assembly. When the hammer on the front slide is in the blade retracted position, the scope coupler is in the second, rearward position on the front slide to prevent the distal viewing end portion of an endoscope or arthroscope coupled to the scope coupler from exerting a blade extending force on the retractable cutting blade assembly, thereby maintaining the cutting blade in a retracted position within the bore of the blade tube. When the hammer on the front slide is in the blade extended position, the scope coupler is in the first, forward position on the front slide to allow the distal viewing end portion of an endoscope or arthroscope coupled to the scope coupler to exert a blade extending force on the retractable cutting blade assembly, thereby causing the cutting blade to project outwardly of the blade tube through the blade slot formed therein and outwardly of the tubular member of the cannula through the axially-extending slot formed therein.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 2 is a side view of the surgical instrument of the present invention, with the attached endoscope, shown in FIG. 1.

FIG. 3 is a perspective view of the surgical instrument of the present invention and endoscope partially received thereby, as shown in FIGS. 1 and 2, with the cannula of the instrument being shown as transparent to illustrate how the distal end of the endoscope causes the retractable blade of the surgical instrument to project outwardly from a slot formed in the cannula.

FIG. 7A is a perspective view of the inner tube and retractable cutting blade forming part of the surgical instrument of the present invention.

FIG. 7B a top plan view of the inner tube and retractable cutting blade forming portions of the surgical instrument of the present invention.

FIG. 7C is a longitudinal cross-sectional view of the distal end portion of the inner tube and cutting blade assembly forming portions of the surgical instrument of the present invention, taken along line 7C-7C of FIG. 7B.

FIG. 7D is an exploded perspective view of the spring-biased, retractable blade assembly forming a portion of the surgical instrument of the present invention.

FIG. 8 is a cross-sectional view of the inner tube, shown in transparency, and the retractable blade assembly mounted therein and forming portions of the surgical instrument of the present invention.

FIG. 9 is cross-sectional view of the distal end portion of the cannula of the surgical instrument of the present invention, and illustrating the inner tube and retractable blade assembly forming portions of the surgical instrument of the present invention situated therein.

FIG. 20 is another perspective view of the inner tube and retractable cutting blade forming part of the surgical instrument of the present invention.

FIG. 21 is an exploded perspective view of the inner tube and retractable cutting blade of the surgical instrument of the present invention shown in FIG. 20.

FIG. 22 is a longitudinal cross-sectional view of the inner tube and cutting blade assembly of the surgical instrument of the present invention shown in FIGS. 20 and 21.

FIG. 23 is a longitudinal cross-sectional view of the distal end portion of the inner tube and cutting blade assembly of the surgical instrument of the present invention shown in FIGS. 20-22.

FIGS. 28A-28L are various views of the cannula forming part of the endoscopic surgical instrument of the present invention.

FIG. 38 is a perspective view of a ball bearing forming part of the second embodiment of the endoscopic surgical instrument of the present invention shown in FIGS. 29-31, and further forming part of the scope coupler assembly.

FIG. 39 is a perspective view of an O-ring forming part of the second embodiment of the endoscopic surgical instrument of the present invention shown in FIGS. 29-31, and further forming part of the scope coupler assembly.

FIG. 40 is a front view of the O-ring of the present invention shown in FIG. 39.

FIG. 41 is a side view of the O-ring of the present invention shown in FIGS. 39 and 40.

FIG. 49 is a perspective view of a hammer forming part of the second embodiment of the endoscopic surgical instrument of the present invention shown in FIGS. 29-31, and further forming part of the front slide assembly.

FIG. 50 is a rear view of the hammer of the present invention shown in FIG. 49.

FIG. 51 is a side view of the hammer of the present invention shown in FIGS. 49 and 50.

FIG. 62 is a top plan view of the cannula of the present invention shown in FIGS. 60 and 61.

FIG. 63 is a rear view of the cannula of the present invention shown in FIGS. 60-62.

FIG. 64 is a front view of the cannula of the present invention shown in FIGS. 60-63.

FIG. 117 is an end view of the slotted spring pin of the present invention shown in FIGS. 115 and 116.

FIG. 118 is a perspective view of an end cap forming part of the second embodiment of the endoscopic surgical instrument of the present invention shown in FIGS. 29-31.

FIG. 119 is a side view of the end cap of the present invention shown in FIG. 118.

FIG. 120 is a rear view of the end cap of the present invention shown in FIGS. 118 and 119.

FIG. 121 is a top plan view of the second embodiment of the endoscopic surgical instrument of the present invention shown in FIGS. 29-31, and illustrating an endoscope mounted on the surgical instrument, with the surgical instrument being shown in a blade retracted state.

FIG. 122 is a cross-sectional view of the surgical instrument of the present invention and the endoscope mounted thereon shown in FIG. 121, taken along line A-A of FIG. 121.

FIG. 123 is a detailed side view of a portion of the blade tube and retractable cutting blade assembly of the present invention and the distal end of the endoscope shown in FIGS. 121 and 122, the portion being shown encircled by the circular line A of FIG. 122.

FIG. 124 is a top plan view of the second embodiment of the endoscopic surgical instrument of the present invention shown in FIGS. 29-31, and illustrating an endoscope mounted on the surgical instrument, with the surgical instrument being shown in a blade extended state.

FIG. 125 is a cross-sectional view of the surgical instrument of the present invention and the endoscope mounted thereon shown in FIG. 124, taken along line A-A of FIG. 124.

FIG. 126 is a detailed side view of a portion of the blade tube and retractable cutting blade assembly of the present invention and the distal end of the endoscope shown in FIGS. 124 and 125, the portion being shown encircled by the circular line A of FIG. 125.

DETAILED DESCRIPTION OF THE PREFERRED EMBODIMENTS

Figure 1:
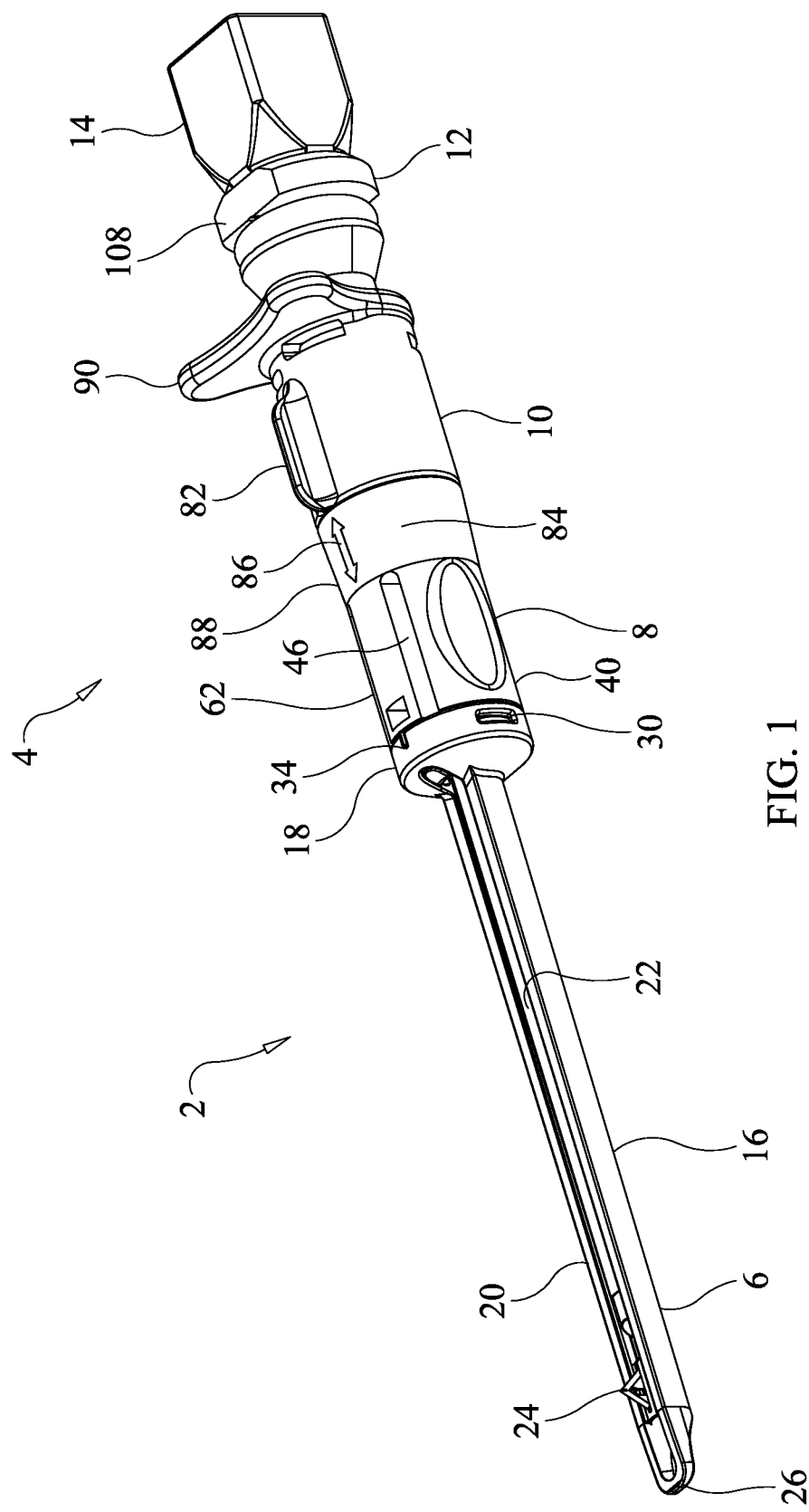
FIG. 1 is a perspective view of a first embodiment of an endoscopic surgical instrument formed in accordance with the present invention, and illustrating a portion of an endoscope partially received by the instrument.
Figure 4:
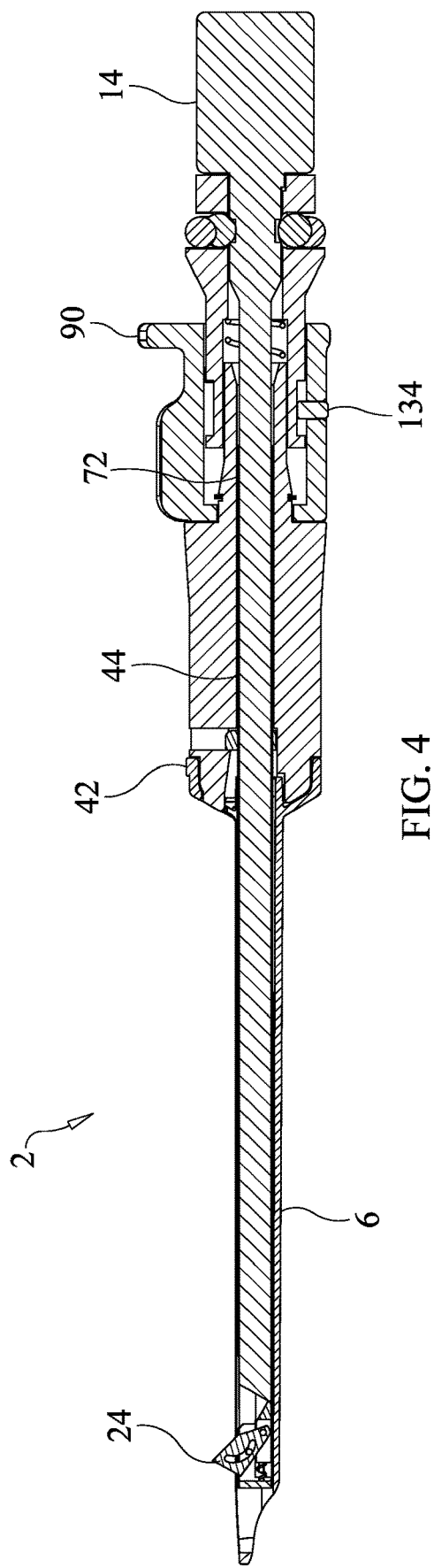
FIG. 4 is a cross-sectional view of the surgical instrument of the present invention and the endoscope shown in FIGS. 1-3, taken along line 4-4 of FIG. 2.
Figure 5:
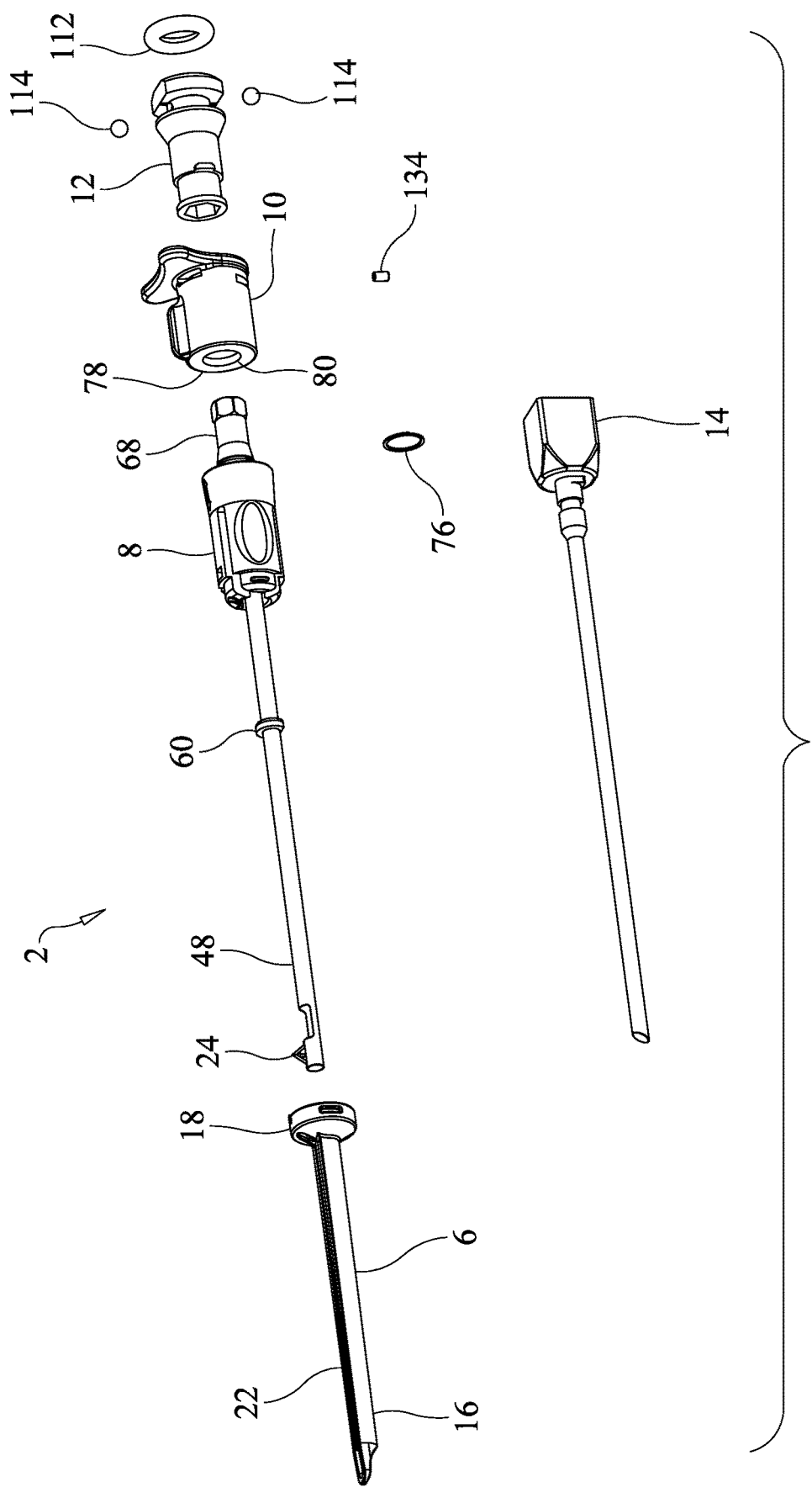
FIG. 5 is a partially exploded view of the surgical instrument of the present invention shown in FIGS. 1-4.

Referring initially to FIGS. 1-5, 10-19 and 25A-28L of the drawings, it will be seen that an endoscopic surgical instrument 2 formed in accordance with the present invention includes a main body assembly 4 and a cannula 6 mounted to the main body assembly 4. More specifically, the main body assembly 4 includes three sections, that is, a front section 8, a middle section 10 that is mounted on the front section 8 and partially rotatable thereon, and a rear section 12 mounted on the middle section 10. The cannula 6 of the surgical instrument 2 is removably attached to the front section 8 of the main body assembly 4. An endoscope or arthroscope 14 is received through the main body assembly 4 and attaches to the rear section 12 thereof, with the distal end of the endoscope extending into the cannula 6, as will be more fully described herein.

The cannula 6 of the surgical instrument 2 includes a tubular member 16 having an internal lumen that extends from an enlarged diameter (when compared to that of the tubular member), cup-shaped member 18 that attaches to the front end of the front section 8 of the main body assembly 4. The tubular member 16 of the cannula 6 includes a flattened top wall 20, and a slot 22 formed through the thickness of the flattened top wall 20 and extending axially thereon over most or at least a portion of the longitudinal length thereof. The slot 22 is provided to allow a retractable blade 24 to project therefrom, as will be explained in greater detail. Preferably, the cannula 6, and at least the tubular member 16 thereof, is transparent so that an endoscope or arthroscope 14 received by the surgical instrument 2 of the present invention and which passes through at least a portion of the lumen of the cannula 6 can view through the clear, transparent cannula 6 in preferably all rotational directions any tissue and other anatomical features at a surgical site when a surgeon is performing a procedure on a patient.

As can be seen in FIGS. 1-5 of the drawings, the distal end 26 of the cannula 6 is preferably closed and blunt, with a curved end 28, to define an obturator thereat so that the cannula 6, when being positioned at a surgical site, will minimize any injury to the tissue that the cannula 6 comes in contact with. The retractable blade 24, as can be seen in FIGS. 1-5, is positioned at the distal end 26 of the cannula 6, but slightly axially inwardly of the obturator end 26 thereof.

The cup-shaped proximate end 18 of the cannula 6 preferably includes two diametrically opposed slots or recesses 30 positioned on a cylindrical side wall 32 thereof, as well as an opening 34 formed through the thickness of a cone-shaped wall 36 interposed between the cylindrical side wall 32 and the tubular member 16 of the cannula 6. The slots 30 receive complementary-shaped protrusions 38 formed on the front end of the front section 8 of the main body assembly 4 for removably attaching and securing the cannula 6 to the front section 8 thereof. The protrusions 38 reside on the free ends of two diametrically opposed resilient members 40 forming part of the front section 8 of the main body assembly 4. The resilient members 40 may be squeezed together radially inwardly of the front section 8 so that the cup-shaped proximate end 18 of the cannula 6 may be fitted thereon, with the protrusions 38 being received by their corresponding slots 30 formed in the cup-shaped proximate end 18 of the cannula 6. The resilient members 40 of the front section 8 are biased to expand radially outwardly to secure the cannula 6 in place on the front section 8 of the main body assembly 4.

The opening 34 formed through the thickness of the conical wall 36 of the cup-shaped proximate end 18 of the cannula 6 serves two purposes. The first is that the opening 34 is formed in the conical wall 36 in communication and in alignment with the slot 22 formed in the flat top wall 20 of the tubular member 16 of the cannula 6 so that the cutting blade 24 of the surgical instrument 2 projecting from the slot 22 in the cannula 6 may be drawn from the distal end 26 to the proximate end 18 of the cannula 6 and through the opening 34 formed in the conical wall 36 of the cup-shaped proximate end 18, if such is necessary during a surgical procedure. Furthermore, the opening 34 formed in the conical wall 36 of the cup-shaped proximate end 18 of the cannula 6 is dimensioned to receive a small projection 42 formed on the front end of the front section 8 of the main body assembly 4 to ensure that the cannula 6 is properly oriented on the main body assembly 4 when it is affixed to the front section 8 thereof.

The front section 8 of the main body assembly 4 of the surgical instrument 2 has an overall generally cylindrical shape and a central bore 44 passing axially therethrough. The two resilient members 40 used to hold the cannula 6 to the main body assembly 4 reside adjacent chordally extending slots 46 to provide space for the resilient members 40 to flex inwardly on the front section 8. The front section 8 also has a tubular member (referred to herein as the inner tube 48) that extends axially outwardly from the front end thereof.

The inner tube 48 defines a bore 50 that extends axially therethrough, and has a closed distal end 52. As will be explained in greater detail, the inner tube 48 is receivable by the tubular member 16 of the cannula 6 in the lumen thereof.

In proximity to the distal end 52 of the inner tube 48, within the bore 50 thereof, is located the retractable cutting blade assembly 54. The cutting blade 24 selectively projects from and retracts into the bore 50 through a narrow slot 56 formed in the side wall of the inner tube 48. Slightly axially inwardly from the distal end 52 of the inner tube 48 is a window 58 defined by a cutaway portion of the side wall over about a 180°, or slightly greater, portion of the side wall. This window 58 is provided so that the distal end of an endoscope or arthroscope 14, which is angled at about 30°, may view through this window 58 and through the clear, transparent cannula 6 any tissue or anatomical structure of a patient at a surgical site during a surgical procedure. As will be explained in greater detail, the distal tubular portion of the endoscope 14 is received by the bore 50 of the inner tube 48 so that the viewing end thereof is positioned in proximity to the window 58 formed in the side wall of the inner tube 48.

Near the proximate end of the inner tube 48, or spaced partially axially inwardly thereof, is fixedly mounted an alignment ring 60 extending radially outwardly from the side wall of the inner tube 48. This alignment ring 60 is force fitted between two diametrically opposed legs 62 forming part of the front section 8 of the main body assembly 4. The legs 62 have radially inwardly facing walls in which are formed arcuate recesses which receive diametrically opposite sides of the alignment ring 60 to secure the proximate end of the inner tube 48 to the front section 8 of the main body assembly 4. The alignment ring 60 is fixedly positioned on the inner tube 48 at a predetermined location on the axial length thereof so that the distal portion 64 of the inner tube 48 projects axially from the front end of the front section 8 of the main body assembly 4 a predetermined distance so as to be received by and extend through most of the full axial length of the cannula lumen. A proximate end portion 66 of the inner tube 48 that extends axially beyond the alignment ring 60 passes through at least a portion of a central bore 44 formed axially through the front section 8 of the main body assembly 4.

The front section 8 of the main body assembly 4, at the rear side thereof, includes an extended, generally tubular portion 68 that projects axially therefrom. This tubular extended portion 68 includes a hexagonally-shaped free end 70 through which the central bore 44 of the front section 8 extends, the extended portion 68 of the front section 8 being received by an axial bore 72 formed centrally in the middle section 10 of the main body assembly 4, as will be explained below.

The middle section 10 of the main body assembly 4 is mounted on the extended portion 68 of the front section 8 at the rear end thereof and is at least partially rotatable on the extended portion 68 of the front section 8, which is received by the central bore 72 of the middle section 10. The middle section 10 is rotatably held in place on the front section 8. To accomplish the mounting of the middle section 10 on the front section 8, the extended portion 68 of the front section 8 includes a circumferential groove 74 formed in the side wall thereof, and a retainer ring or O-ring 76 received in the groove 74. The front end of the middle section 10 is formed as a washer-like disc 78 having a central opening 80 that leads to and communicates with the bore 72 formed through the middle section 10, the central opening 80 being particularly dimensioned to closely fit onto the extended portion 68 of the front section 8 near where the extended portion 68 projects axially from the rear end of the larger diameter portion of the front section 8, that is, between the rear end of the front section 8 and where the retainer ring or O-ring 76 is situated on the extended portion thereof. The middle section 10 is forced axially onto the extended portion 68 of the front section 8 and over the retainer ring 76 such that the retainer ring 76 holds the middle section 10 in place at the rear of the front section 8 but allows the middle section 10 to at least partially rotate thereon.

The middle section 10 of the main body assembly 4 has a generally cylindrical shape. The middle section 10 includes a switch 82 formed as a protruding tab extending radially outwardly from the outer side wall thereof. This switch 82 is movable by finger pressure and facilitates the surgeon rotating the middle section 10 on the front section 8 in at least three different positions. More specifically, the middle section 10 may be rotated about 30° in opposite directions with respect to the front section 8 of the main body assembly 4 such that the switch 82 (i.e., the protruding tab) is in alignment with first indicia 84, preferably reading the word "SCOPE" located on the cylindrical outer wall of the front section 8 adjacent to the middle section 10, when the switch 82 is in the +30° position relative to the front section 8; or in alignment with second indicia 86 (preferably a double-ended arrow) also located on the outer wall of the cylindrical portion of the front section 8, when the switch 82 is in a 0° position relative to the front section 8; or in alignment with third indicia 88 (preferably reading the word "BLADE") also located on the outer wall of the cylindrical portion of the front section 8 of the main body assembly 4, when the switch 82 on the middle section 10 is in the −30° position relative to the front section 8 of the main body assembly 4.

As will be explained in greater detail, when the switch 82 on the middle section 10 is rotated to the "SCOPE" indicia 84 on the front section 8, the distal end of an endoscope or arthroscope 14 inserted through the main body assembly 4 and bore 50 of the inner tube 48 of the surgical instrument 2 will be prevented from axially extending more than a predetermined distance in the inner tube bore 50 so as not to engage the retractable blade assembly 54 such that the retractable cutting blade 24 does not project outwardly from the slot 56 formed in the inner tube 48 and the slot 22 formed in the cannula 6. When the middle section 10 is rotated such that the switch 82 is in alignment with the word "BLADE" 88 on the front section 8, the distal end of the endoscope 14 is permitted to engage the retractable blade assembly 54 and to cause the cutting blade 24 to project through the slot 56 formed in the side wall of the inner tube 48 and the slot 22 formed in the cannula 6. When the middle section 10 is rotated such that the switch 82 is in alignment with the double arrow indicia 86 situated on the front section 8, this position of the switch 82 allows the endoscope or arthroscope 14 to move axially forward on the surgical instrument 2 and permits a transition from the "SCOPE" state of the surgical instrument 2, where the cutting blade 24 remains safely retracted within the bore 50 of the inner tube 48, to the "BLADE" state of the surgical instrument 2, where the distal end of the endoscope 14 may engage the retractable blade assembly 54 to cause the cutting blade 24 to project outwardly from the inner tube 48 and the slot 22 formed in the cannula 6.

At the rear axial end of the middle section 10 of the main body assembly 4 is located a double wing handle 90 formed as a protruding planar flange extending radially from the cylindrical outer wall of the middle section 10. This double wing handle 90 is graspable by a surgeon during a surgical procedure and facilitates not only axial movement of the endoscope 14 relative to the surgical instrument 2 as the surgical instrument 2 and endoscope 14 transition between the "SCOPE" state and the "BLADE" state, but also axial movement of the cutting blade 24 along at least a portion of the length of the cannula slot 22 when the cannula 6 is disengaged from the main body assembly 4 of the instrument 2 and properly positioned at a surgical site.

The cylindrical inner wall of the middle section 10 which defines the central bore 72 has formed near the rear end of the middle section 10 first and second pairs of diametrically opposed, arcuate notches, recesses or slots 92, 94 formed therein, each slot or recess 92, 94 extending about 30° on the inner wall. More specifically, a first set of arcuate recesses or slots 92 formed in the inner wall is located near the rear axial end of the middle section 10, and a second set of arcuate recesses or slots 94 is formed in the inner wall of the middle section 10 but more axially inwardly thereon from where the first set of arcuate recesses or slots 92 is situated. Even more specifically, the second set of arcuate slots 94 is more axially inwardly situated with respect to the location of the first set of arcuate slots 92 by about 3/16 inches. This difference in the location of the first and second sets of arcuate recesses or slots 92, 94 determines whether the distal end of the endoscope 14 received by the surgical instrument 2 of the present invention will be permitted to engage, or will be prevented from engaging, the retractable blade assembly 54. As will be explained below, each slot 92, 94 of the first and second sets can receive a corresponding tab 96 protruding from opposite sides of the outer wall of the rear section 12 of the main body assembly 4 which is received by the central bore 72 of the middle section 10.

The rear section 12 of the main body assembly 4 of the surgical instrument 2 is also generally cylindrical in shape and has a bore 98 formed axially therethrough. The rear end 100 of the rear section 12 has a larger diameter than the axially opposite front end 102, with a conically-shaped mid-portion 104 that transitions from the larger diameter rear end 100 to the smaller diameter front end 102. The rear end wall 106 of the rear section 12 may include diametrically opposite flattened sides 108 to make it easier to slip an O-ring 112 into a circular groove 110, as described in more detail below.

On the outer wall of the rear section 12, and between the rear wall 106 and the conically-shaped mid-portion 104 of the rear section 12, is located a circular groove 110 in which an O-ring 112 is received. Ball bearings 114 are received in openings 116 formed on diametrically opposite sides of the outer wall of the rear section 12 in the groove 110 and underneath the O-ring 112. Each opening 116 extends through the thickness of the outer wall so as to be in communication with the axial bore 98 formed centrally in the rear section 12. Furthermore, these openings 116 have a smaller diameter than that of each ball bearing 114 so that only a portion of each ball bearing 114 projects into the bore 98 of the rear section 12. The ball bearings 114 are held in place in their respective openings 116 and biased radially inwardly towards the central bore 98 of the rear section 12 by the O-ring 112.

Figure 6:
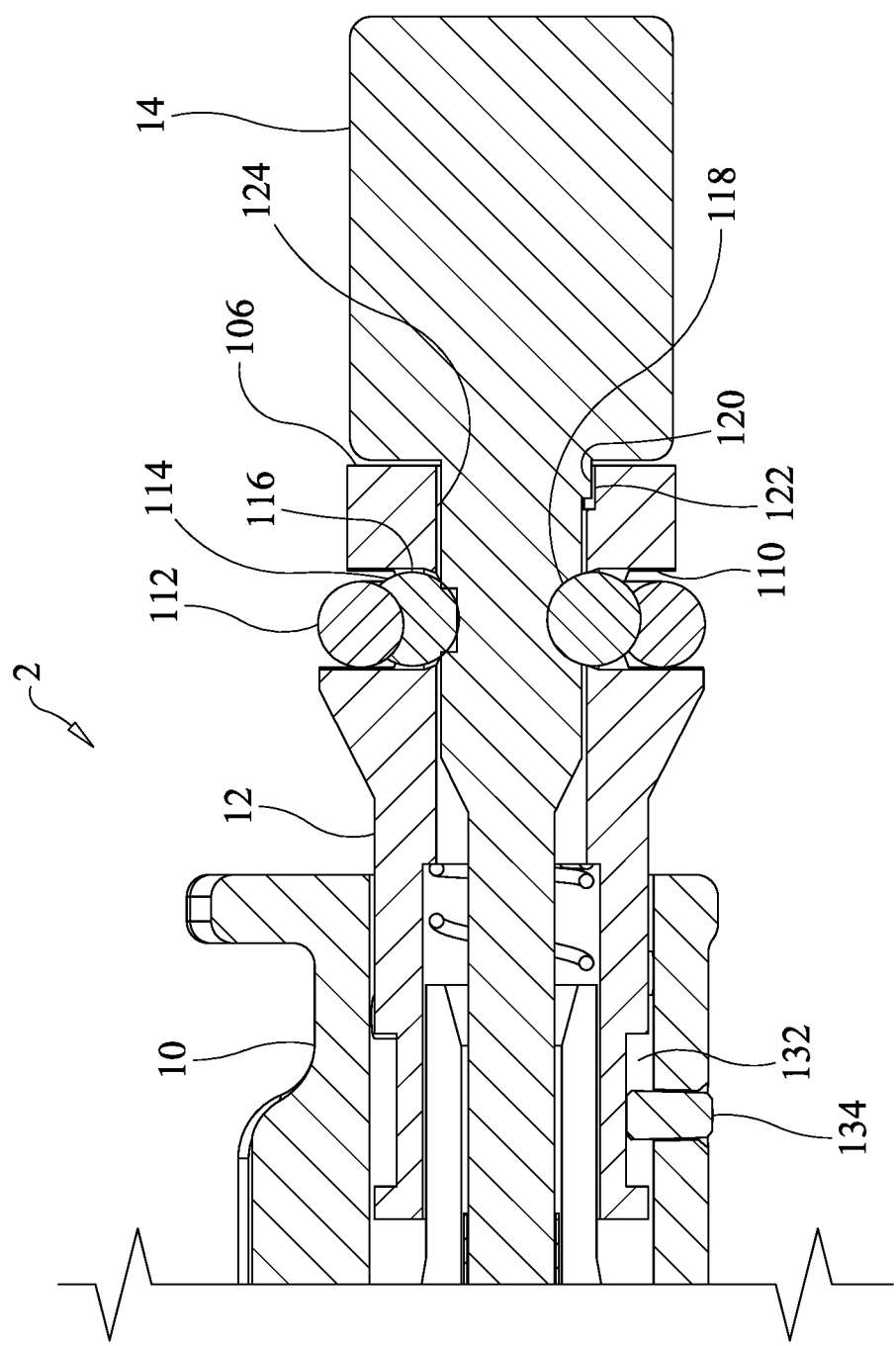
FIG. 6 is a cross-sectional view of the proximate end portion of the surgical instrument of the present invention shown in FIGS. 1-5, and further illustrating an endoscope being received thereby.
Figure 10:
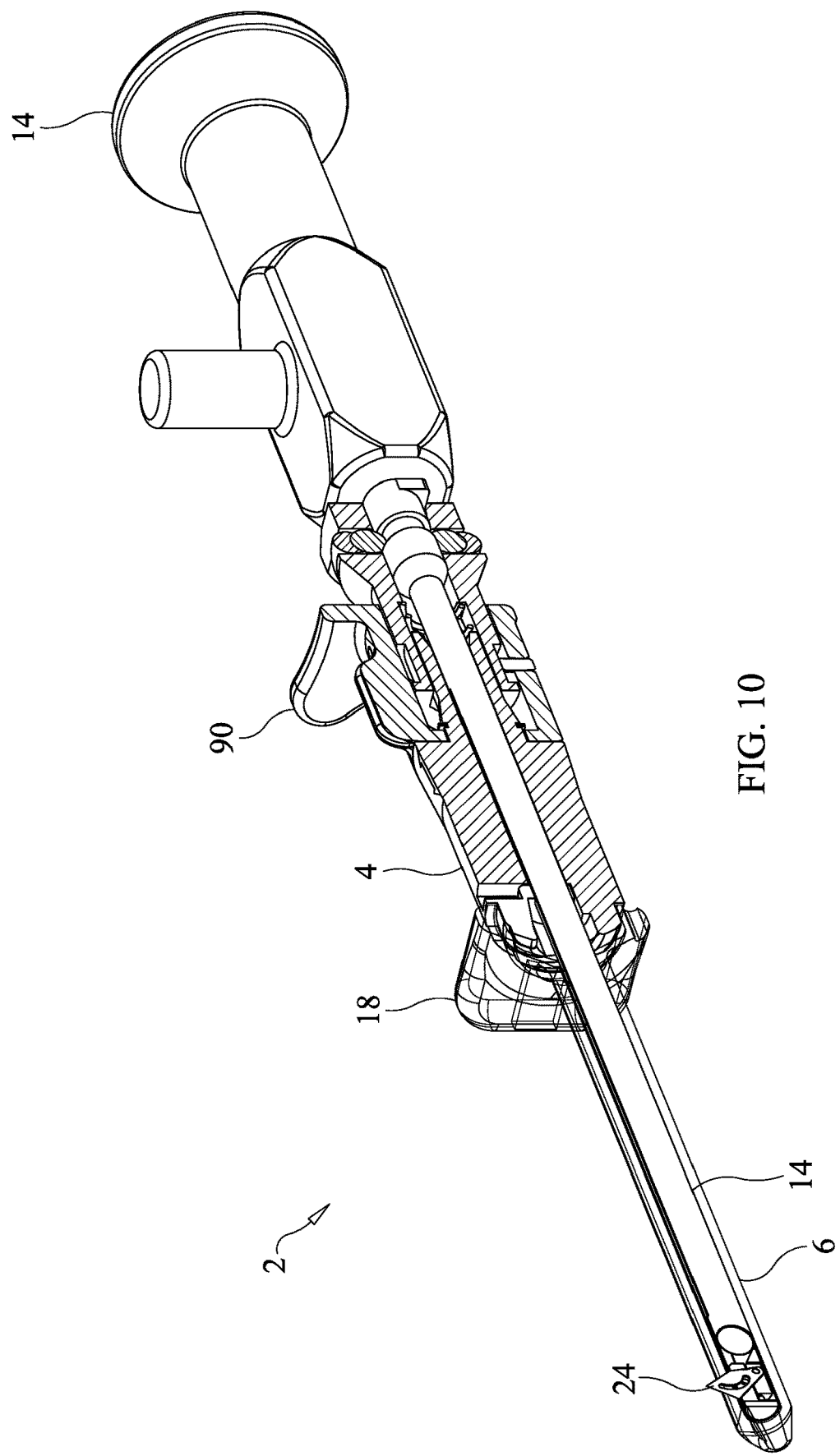
FIG. 10 is a perspective view of the surgical instrument of the present invention, shown with a portion thereof cut away, and illustrating the surgical instrument being mounted on the distal end of an endoscope.
Figure 11:
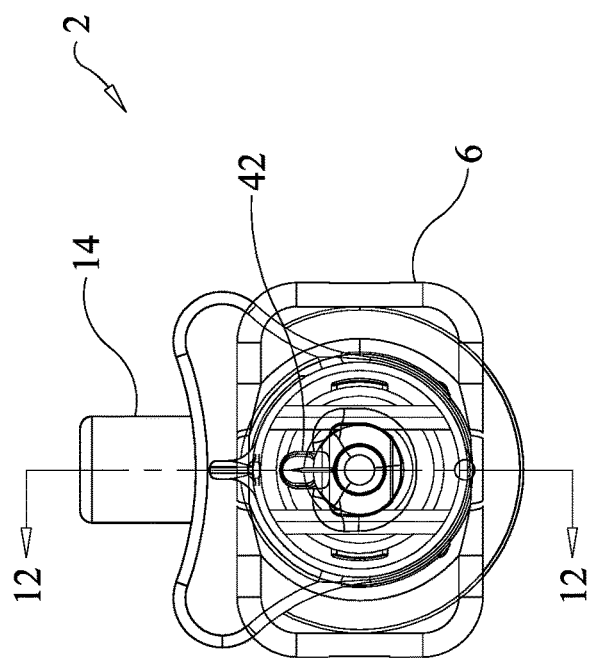
FIG. 11 is a front elevational view of the surgical instrument of the present invention and endoscope on which the surgical instrument is mounted shown in FIG. 10.
Figure 12:
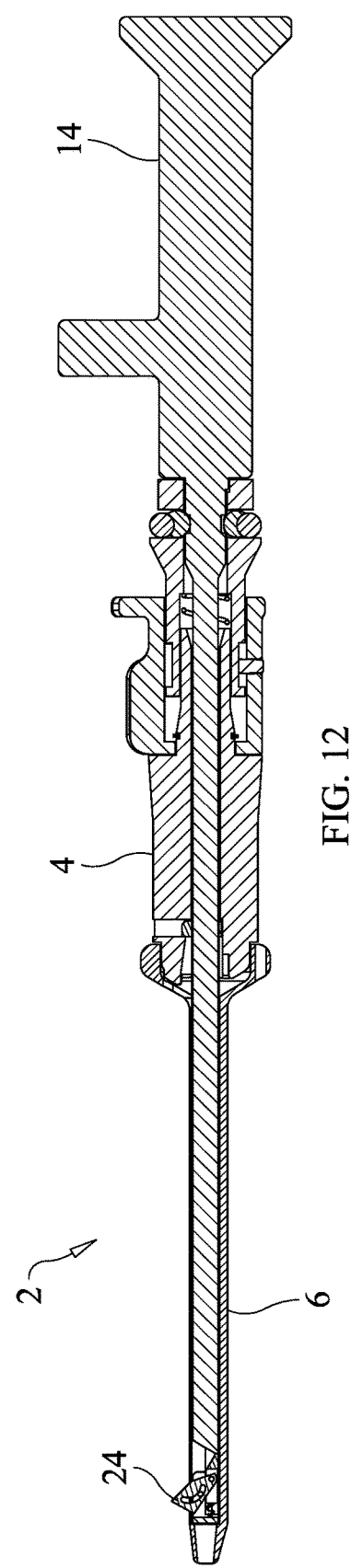
FIG. 12 is a transverse cross-sectional view of the surgical instrument of the present invention and endoscope shown in FIGS. 10 and 11, taken along line 12-12 of FIG. 11.
Figure 13:
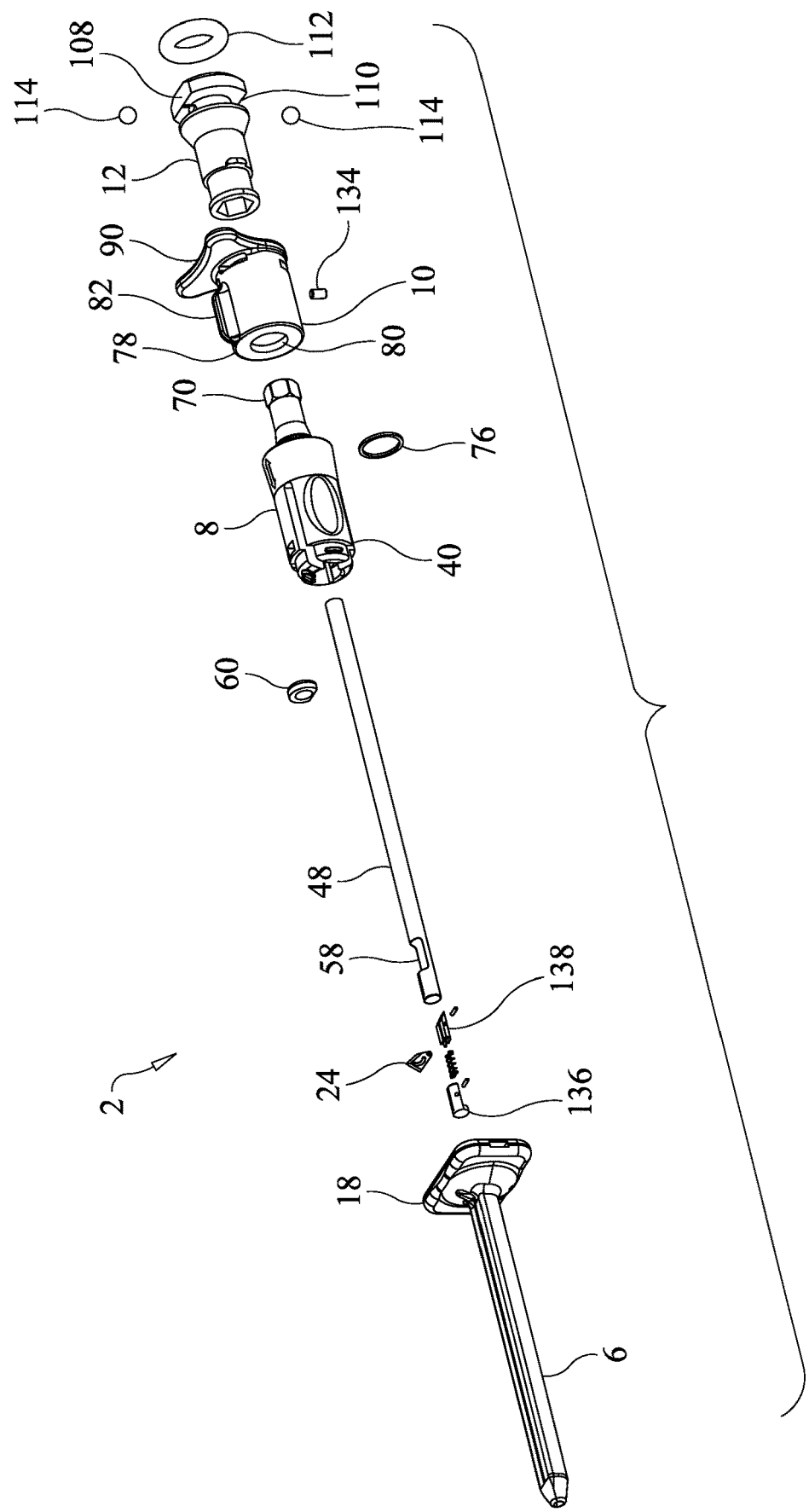
FIG. 13 is an exploded view of the surgical instrument of the present invention shown in FIGS. 10-12.
Figure 14:
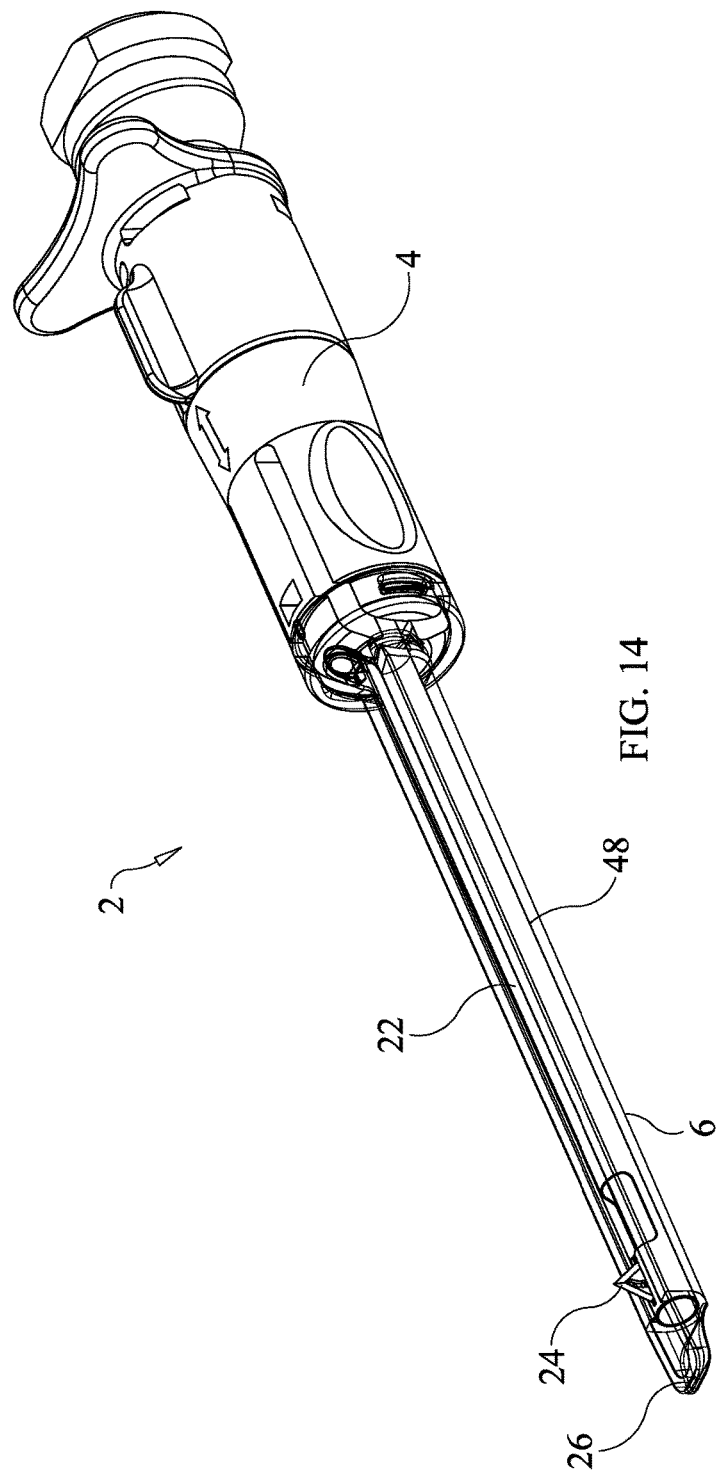
FIG. 14 is another perspective view of the endoscopic surgical instrument formed in accordance with the present invention.
Figure 15:
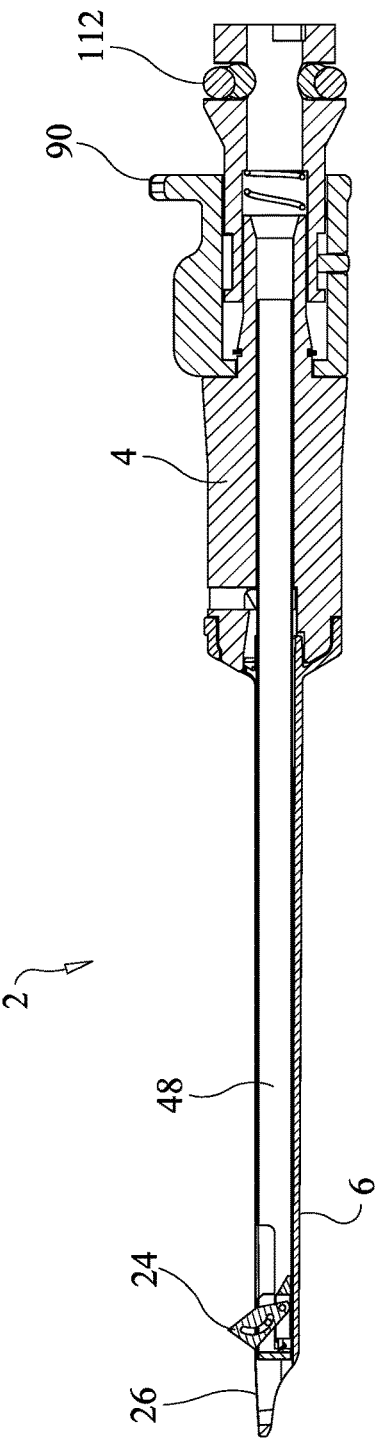
FIG. 15 is a longitudinal cross-sectional view of the endoscopic surgical instrument of the present invention shown in FIG. 14.
Figure 16:
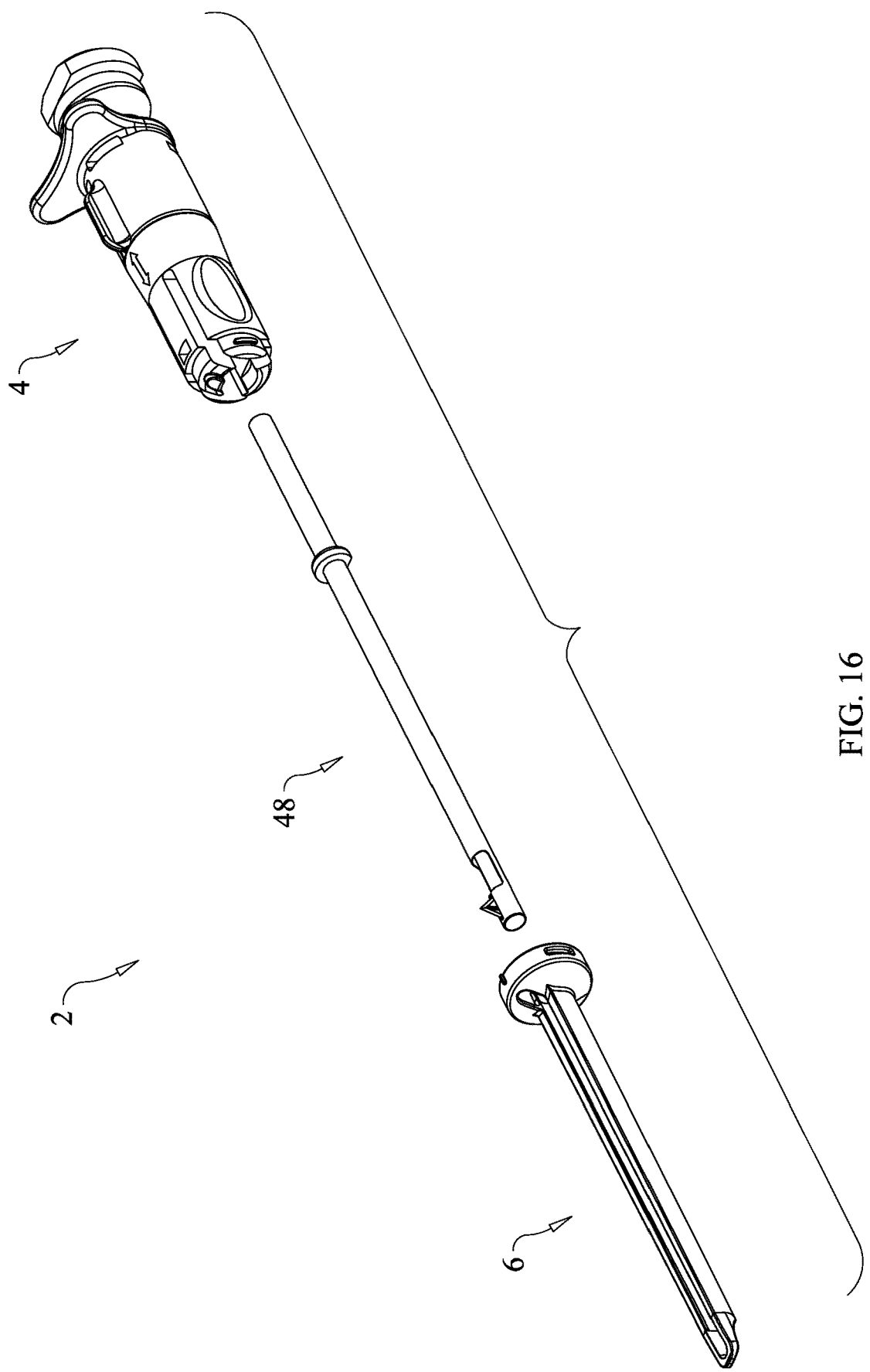
FIG. 16 is a partially exploded perspective view of the endoscopic surgical instrument of the present invention shown in FIGS. 14 and 15.
Figure 17:
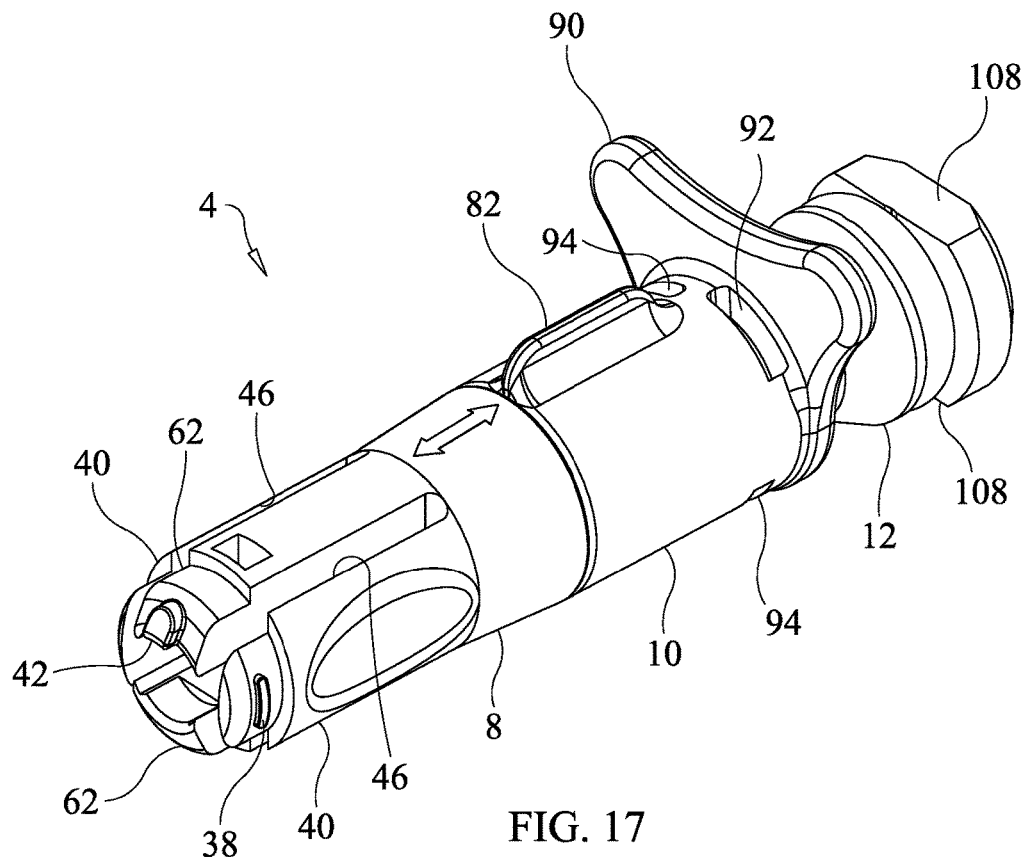
FIG. 17 is a perspective view of the main body assembly forming part of the endoscopic surgical instrument of the present invention.
Figure 18:
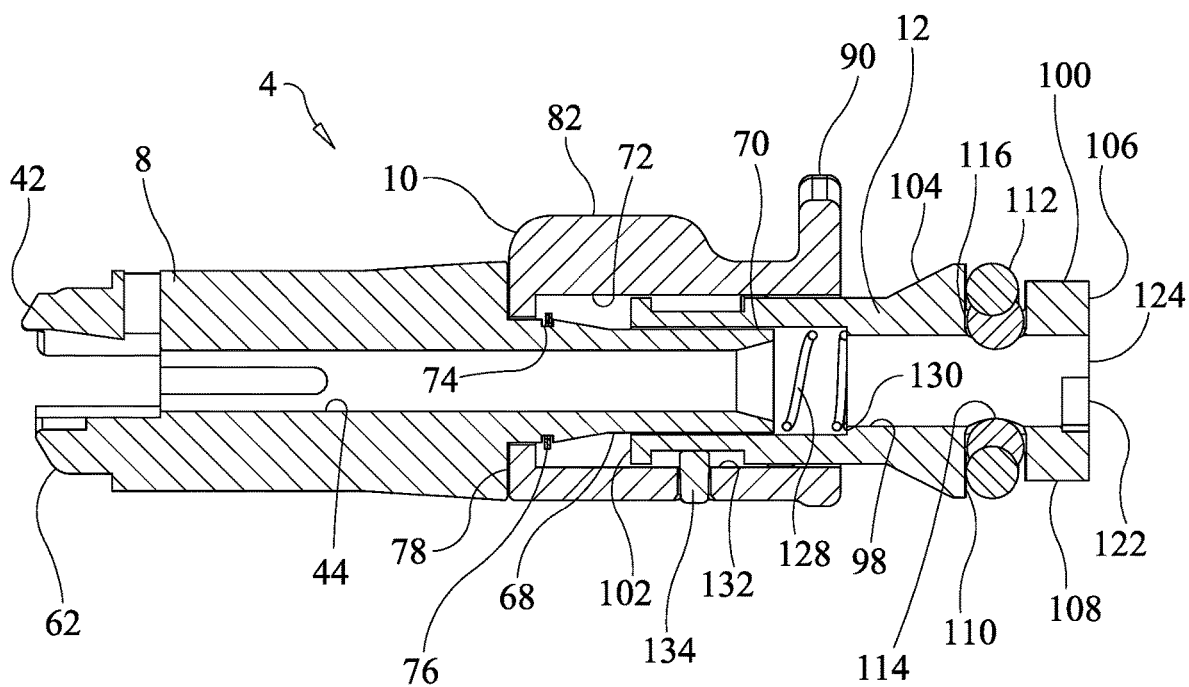
FIG. 18 is a longitudinal cross-sectional view of the main body assembly of the endoscopic surgical instrument of the present invention shown in FIG. 17.
Figure 19:
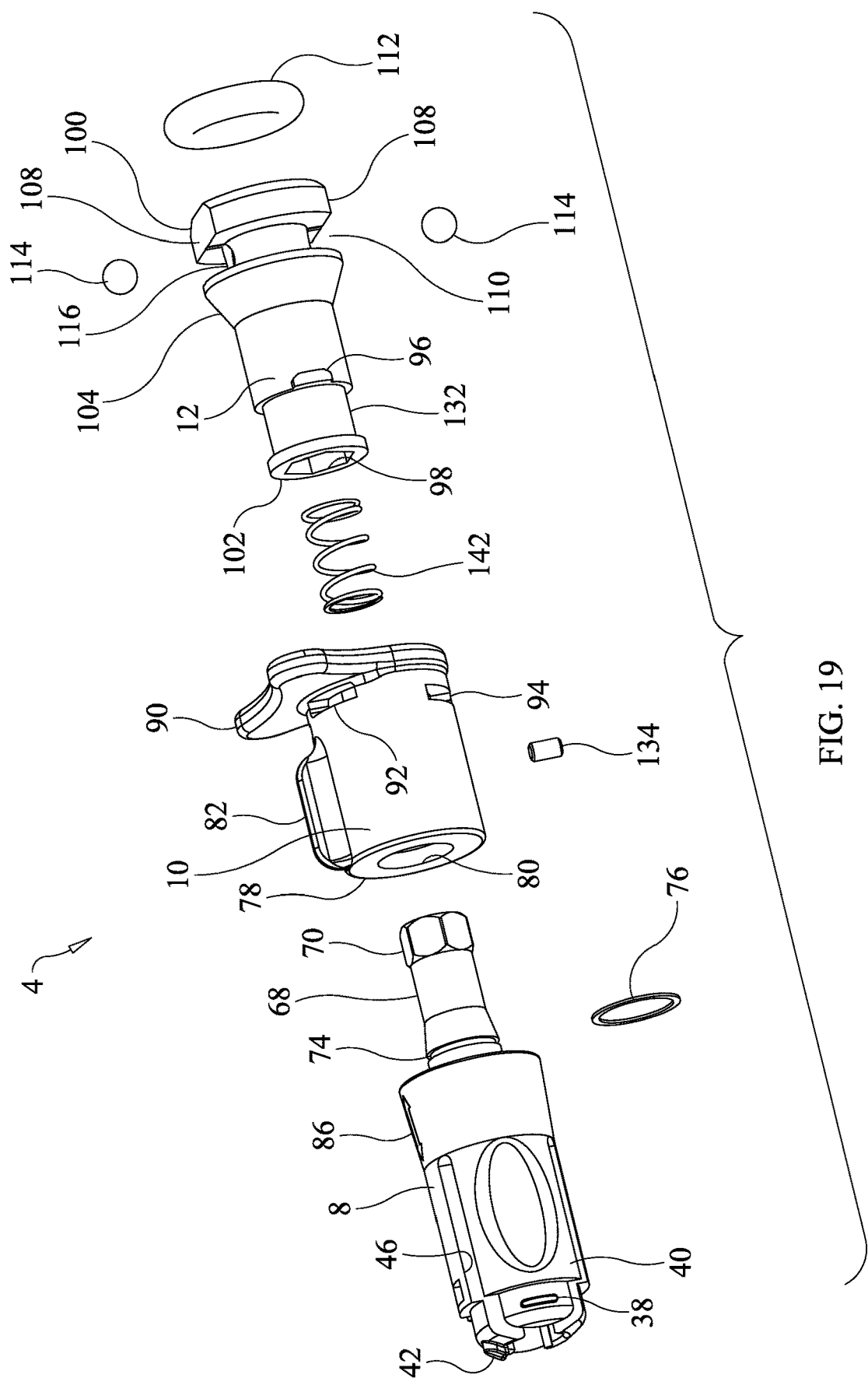
FIG. 19 is an exploded perspective view of the main body assembly of the endoscopic surgical instrument of the present invention shown in FIGS. 17 and 18.
Figure 24:
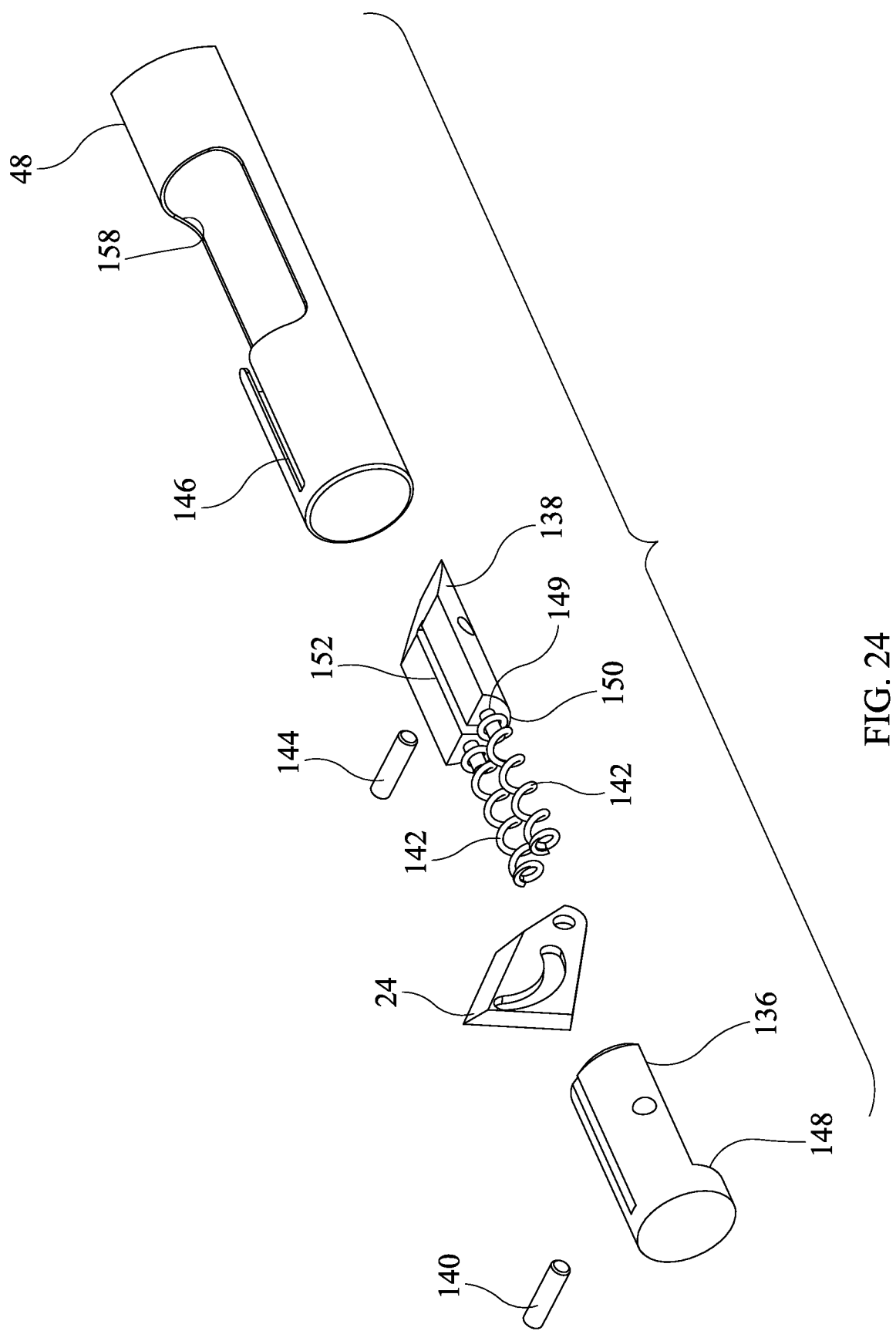
FIG. 24 is an exploded view of the spring-biased, retractable blade assembly forming a portion of the surgical instrument of the present invention shown in FIGS. 20-23.
Figure 25A:
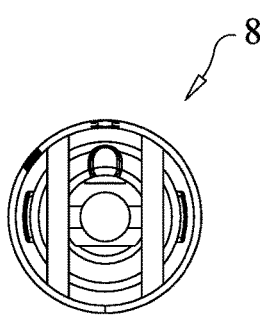
FIGS. 25A-25I are various views of the front section of the main body assembly forming part of the endoscopic surgical instrument of the present invention.
Figure 25B:
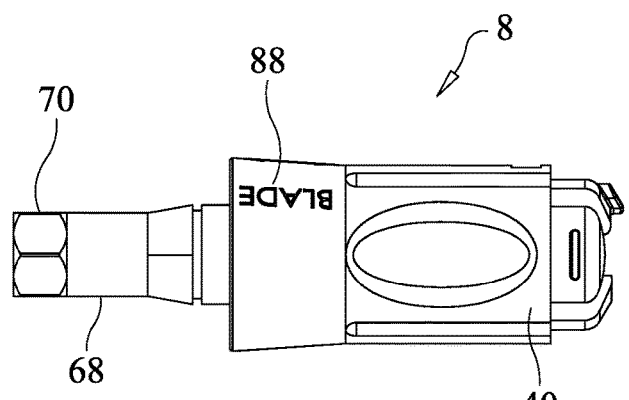
Figure 25C:
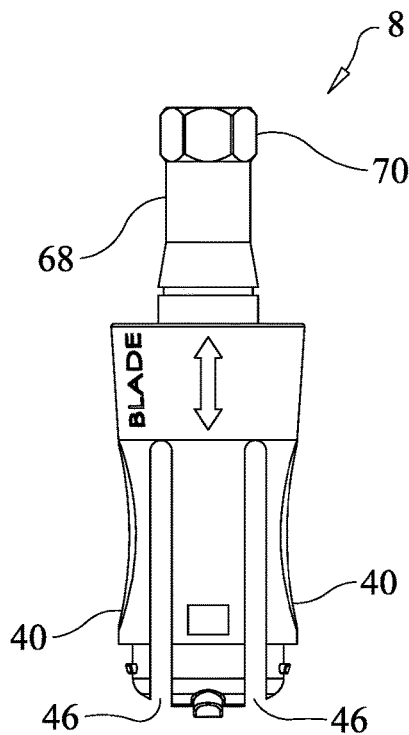
Figure 25D:
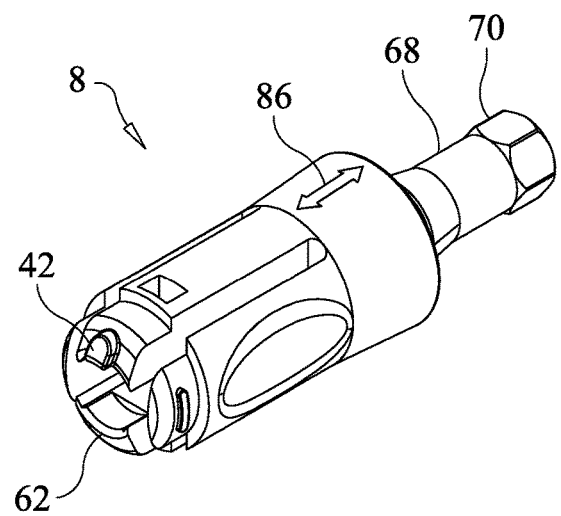
Figure 25E:
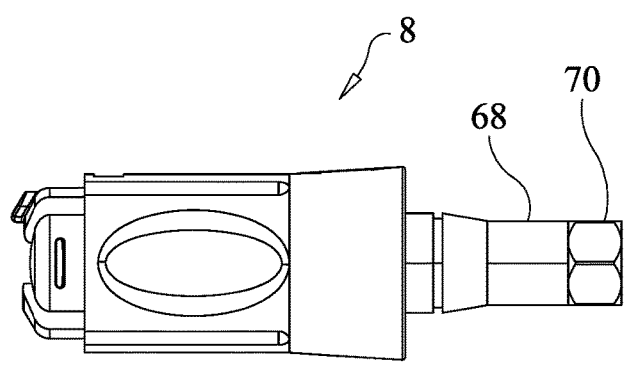
Figure 25F:
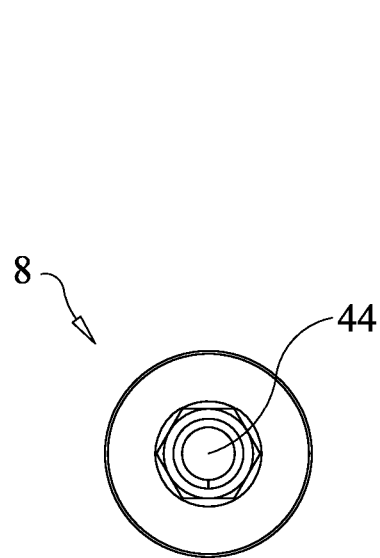
Figure 25G:
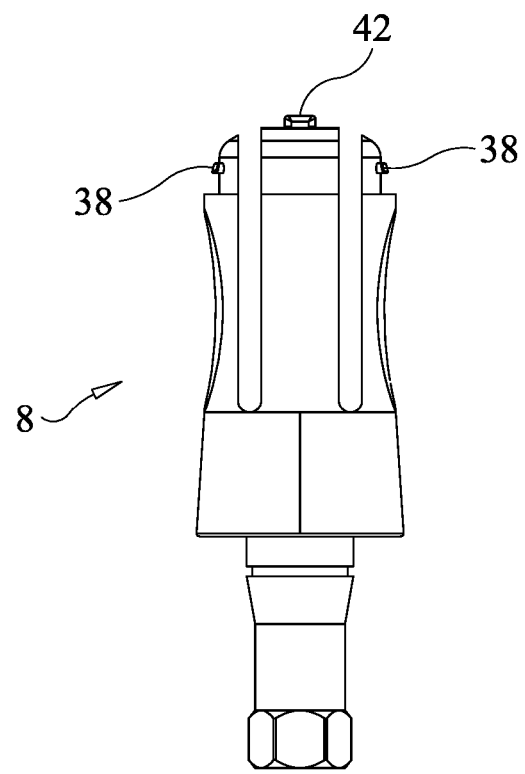
Figure 25H:
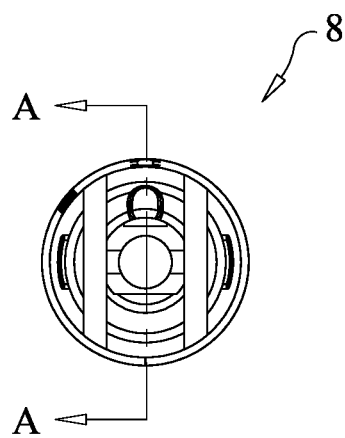
Figure 25I:
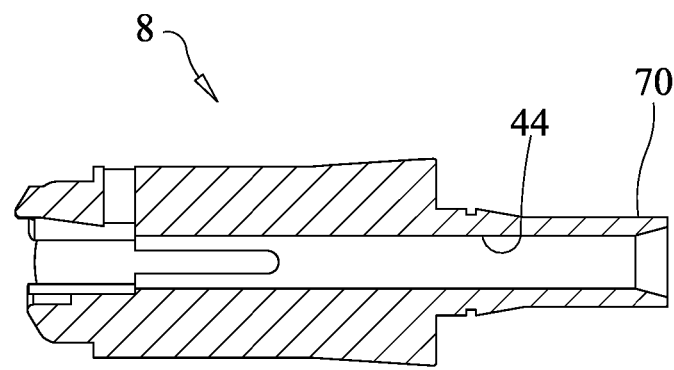
Figure 26A:
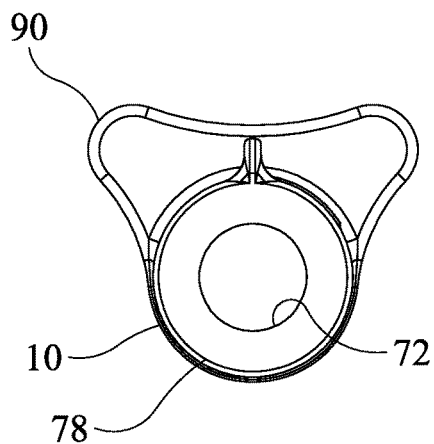
FIGS. 26A-26L are various views of the middle section of the main body assembly forming part of the endoscopic surgical instrument of the present invention.
Figure 26B:
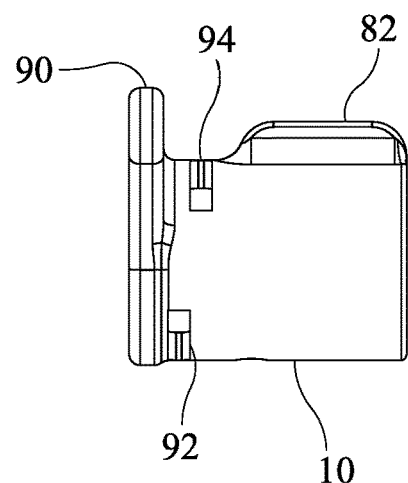
Figure 26C:
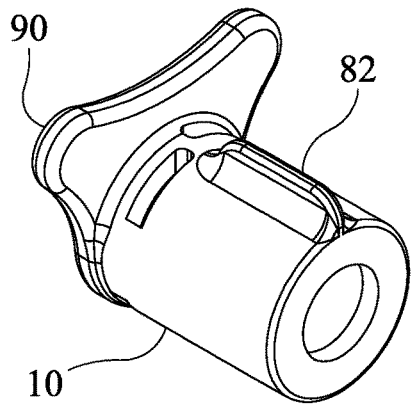
Figure 26D:
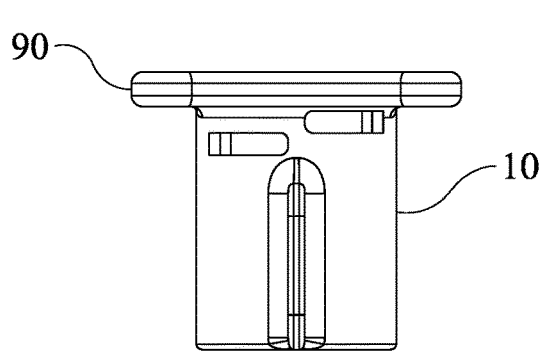
Figure 26E:
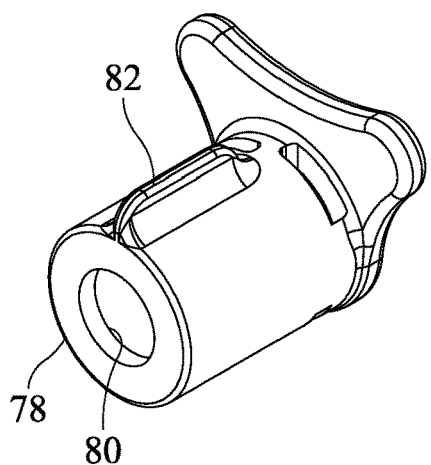
Figure 26F:
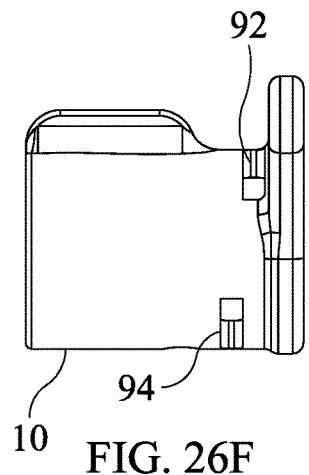
Figure 26G:
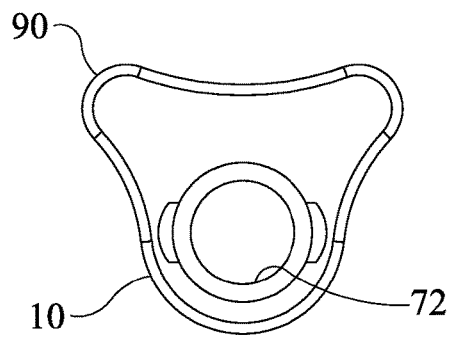
Figure 26H:
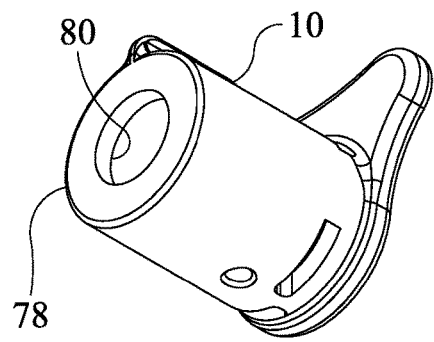
Figure 26I:
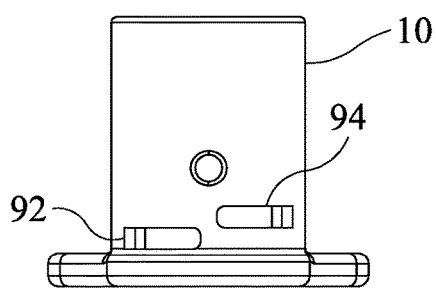
Figure 26J:
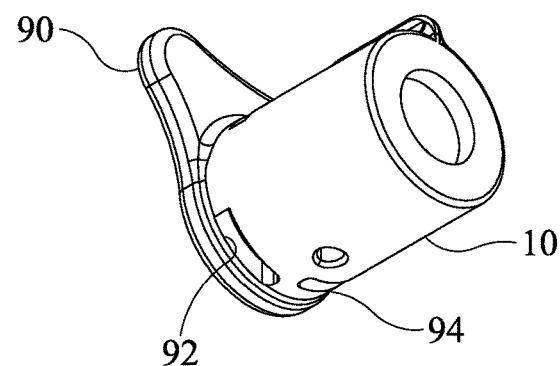
Figure 26K:
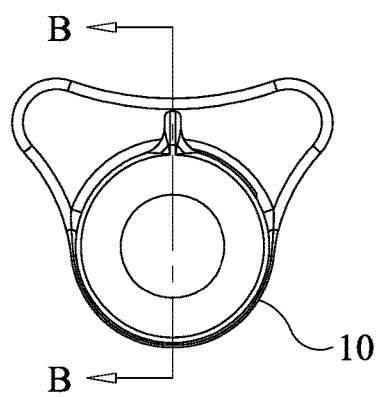
Figure 26L:
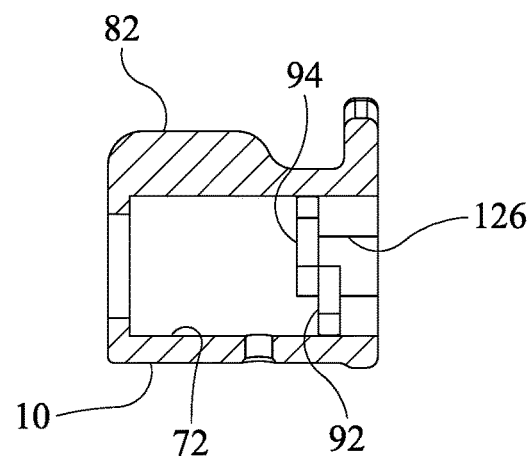
Figure 27A:
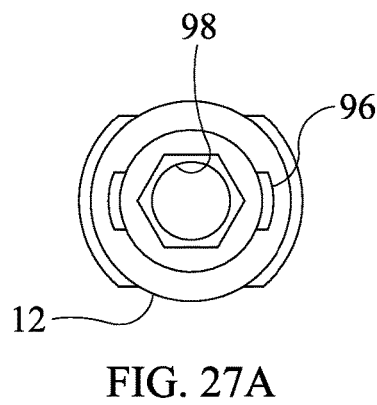
FIGS. 27A-27L are various views of the rear section of the main body assembly forming part of the endoscopic surgical instrument of the present invention.
Figure 27B:
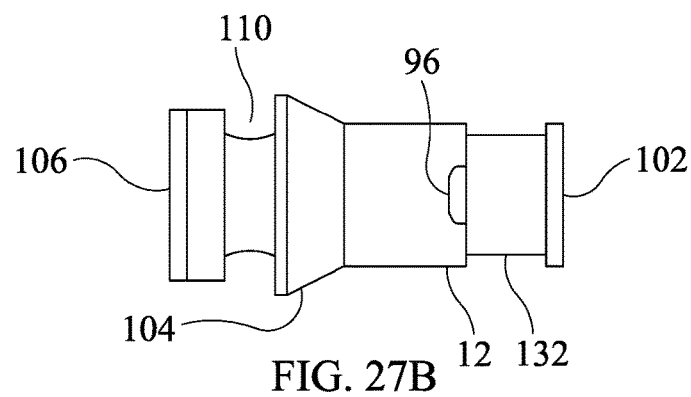
Figure 27C:
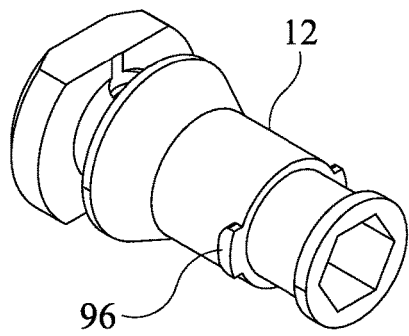
Figure 27D:
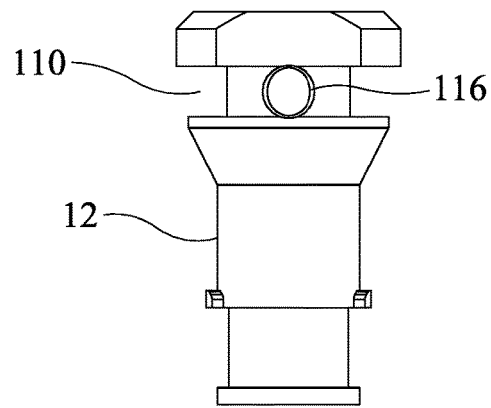
Figure 27E:
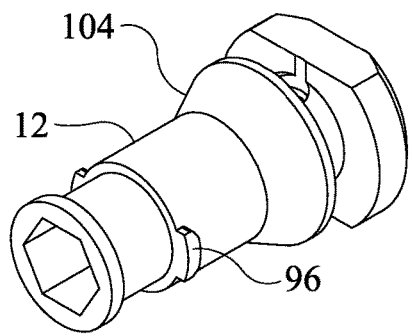
Figure 27F:
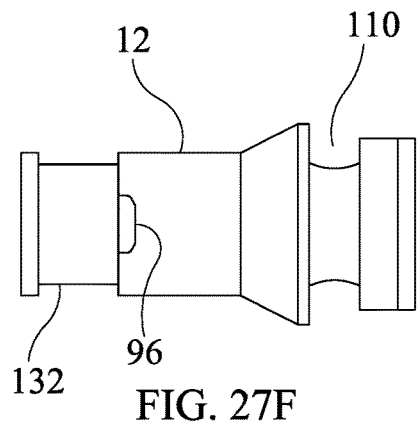
Figure 27G:
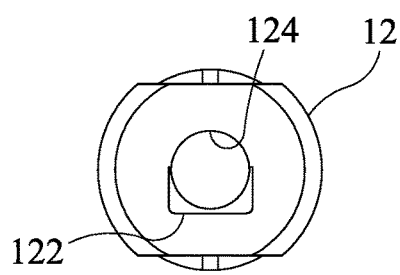
Figure 27H:
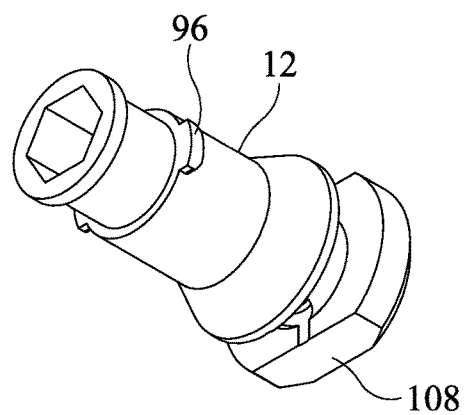
Figure 27I:
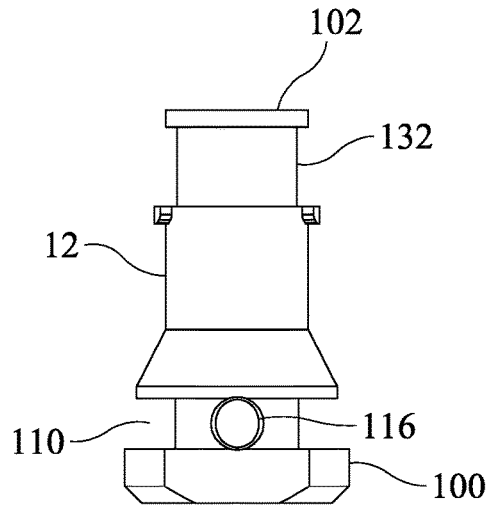
Figure 27J:
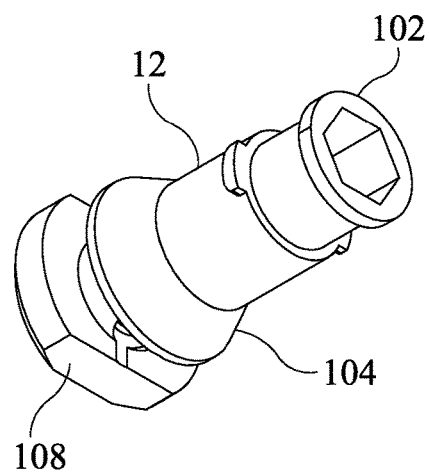
Figure 27K:
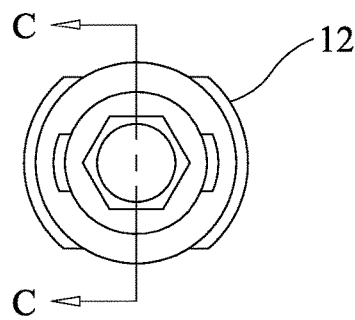
Figure 27L:
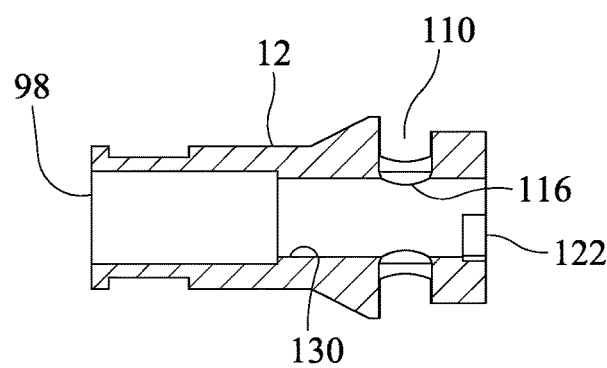
Figure 28G:
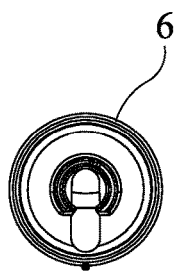
Figure 28H:
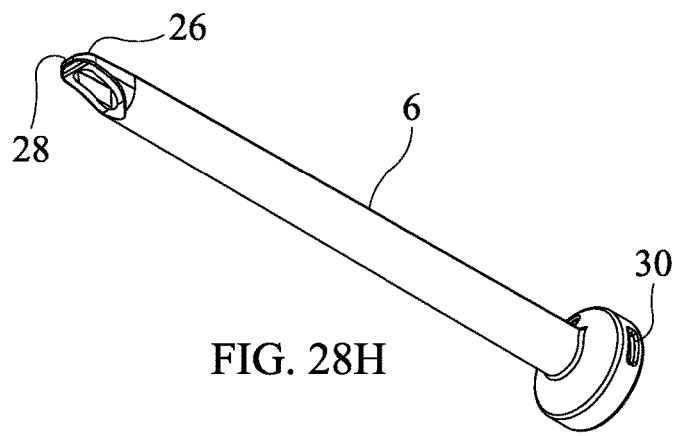
Figure 28I:
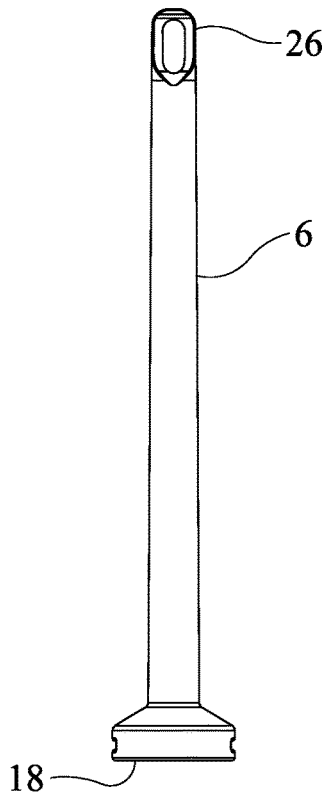
Figure 28J:
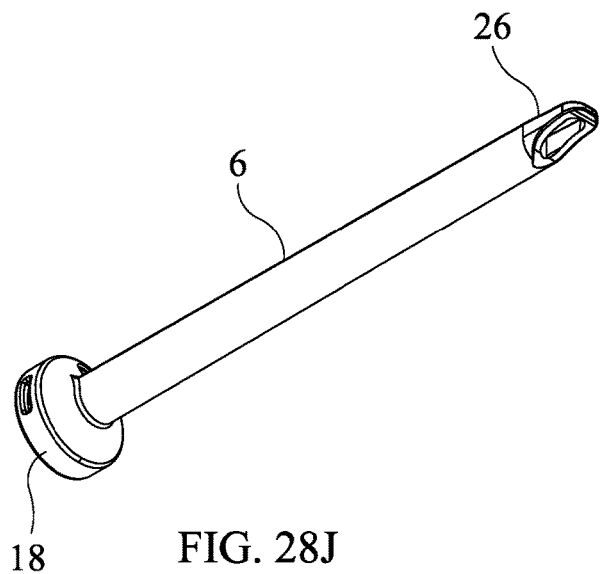
Figure 28K:
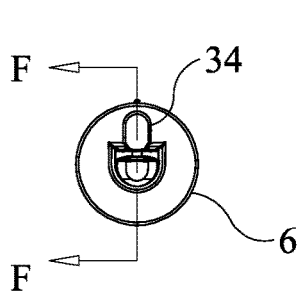
Figure 28L:
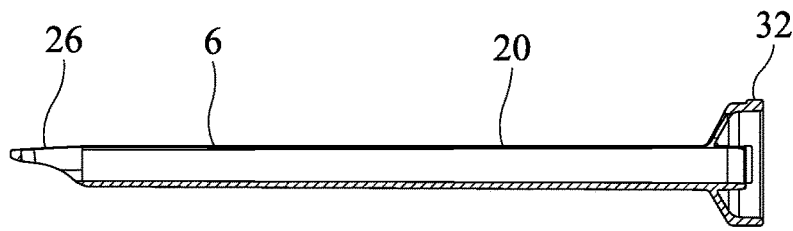

The purpose of using the combination of a retaining O-ring 112 and ball bearings 114 is to allow an endoscope 14 to be securely retained axially on the surgical instrument 2 of the present invention until forcibly removed therefrom. As shown in FIG. 6 of the drawings, many endoscopes 14 have a circular groove 118 formed in a cylindrical outer wall thereof. When the endoscope 14 is inserted into the main body assembly 4 of the surgical instrument 2 of the present invention, the groove 118 on the endoscope 14 is aligned with the openings 116 and inwardly protruding ball bearings 114 on the rear section 12 of the main body assembly 4. The endoscope 14 is pushed axially by the surgeon into the main body assembly 4 through the central bore 98 of the rear section 12 until the ball bearings 114 come to rest in the groove 118 of the endoscope 14, locking the endoscope 14 in place within the surgical instrument 2 of the present invention. The endoscope 14 may be removed axially from the surgical instrument 2 by overcoming the force exerted thereon by the ball bearings 114 and O-ring 112 of the surgical instrument 2. Additionally, it should be noted that, preferably, one side of the groove 118 formed in the outer wall of the endoscope 14 is deeper than a diametrically opposite side of the groove 118. Furthermore, the cylindrical outer wall of the endoscope 14 is formed with a shoulder 120 at a circumferential portion thereof, which shoulder 120 may be received by a notch or flattened portion 122 of an opening 124 formed in the rear wall 106 of the rear section 12 of the main body assembly 4 to ensure that the endoscope 14 is properly oriented with respect to the surgical instrument 2 and the slot 22 formed in the cannula 6 when the endoscope 14 and surgical instrument 2 are mated together.

The two tabs 96 mentioned previously that are formed on the exterior of the rear section 12 of the main body assembly 4 are situated more towards the front end 102 of the rear section 12 and are received in either the first set of diametrically opposed arcuate recesses or slots 92 formed in the inner wall of the middle section 10, or the more axially inwardly situated second set of diametrically opposed arcuate recesses or slots 94 formed in the inner wall of the middle section 10. The tabs 96 are received in axially extending, diametrically opposed grooves 126 formed in the inner wall of the middle section 10 at the rear wall 106 thereof, the grooves 126 leading to and communicating with the first set of arcuate recesses or slots 92 and the second set of arcuate recesses or slots 94, the tabs 96 being received in either set of recesses or slots 92, 94 depending upon how far the rear section 12 is pushed into the middle section 10 and which way the middle section 10 is rotated on the front section 8 and the rear section 12 of the main body assembly 4. The axial bore 98 formed in the rear section 12 receives a compression spring 128, one axial end thereof resting against a decreased diameter seat 130 formed in the bore 98 of the rear section 12. The other axial end of the compression spring 128 engages the hexagonal end face of the extended portion 68 of the front section 8, which extended portion 68 is received within the bore 98 of the rear section 12 at the front end portion 102 thereof. The inner wall of the front end portion 102 of the rear section 12 which defines the axial bore 98 therein is also hexagonally shaped to receive the hexagonally-shaped extended portion 68 of the front section 8 so that the hexagonal end of the extended portion 68 of the front section 8 is closely received by the hexagonal bore 98 of the rear section 12 to join the front and rear sections 8, 12 together but allowing relative axial movement between the two sections 8, 12.

The front end portion 102 of the rear section 12 of the main body assembly 4 includes a cylindrical, relatively wide, groove 132 of decreased diameter formed in the outer wall thereof. This groove 132 has an axial length sufficient to allow relative axial movement between the rear section 12 and the front section 8 of the main body assembly 4 so that the tabs 96 may transition between and may be received by either the first set of recesses or slots 92 formed in the middle section 10 or the second set of recesses or slots 94. The middle section 10, mounted on the extended portion 68 of the front section 8, can rotate at least partially with respect to the front section 8 and the rear section 12.

The compression spring 128, captively retained within the bore 98 of the rear section 12 of the main body assembly 4, biases the rear section 12 axially outwardly from the middle section 10 so that the endoscope 14 received by the surgical instrument 2 of the present invention does not inadvertently engage the retractable blade assembly 54 and cause the cutting blade 24 to project through the slot 22 of the cannula 6. A pin 134 is received in a radially extending opening formed through the thickness of the outer wall of the middle section 10 and into the bore 72 thereof, and is received within the relatively wide groove 132 formed in the outer side wall of the rear section 12 of the main body assembly 4. The pin 134 thus retains the rear section 12 to the middle section 10 and, indirectly, to the front section 8, but allows axial and rotatable partial movement between the middle section 10 and the rear section 12, in order to allow the tabs 96 on the rear section 12 to transition between the first set of grooves or slots 92 and the second set of grooves or slots 94 formed on the middle section 10.

The retractable blade assembly 54 will now be described, and reference should be had to FIGS. 7A-D, 8, 9 and 20-24 of the drawings. The retractable blade assembly 54 is positioned at the distal end 52 of the inner tube 48 and forms a closure at the open end of the tube 48. The retractable blade assembly 54 includes a top blade housing 136, a bottom blade housing 138, an actuator pin 140, a retractable cutting blade 24, a compression spring 142 and a pivot pin 144.

More specifically, and as shown in FIGS. 7A-D and 20-24 of the drawings, the top blade housing 136 is situated at the distal end 52 of the inner tube 48, as mentioned previously, and closes the end of the tube 48. Thus, the top blade housing 136 is fixedly mounted in the inner tube 48. The top blade housing 136 includes a slot 146 formed through the thickness thereof through which the cutting blade 24 may extend from and retract into. This slot 146 in the top blade housing 136 is positioned to be in alignment with a similar slot 56 formed through the thickness of the outer wall of the inner tube 48 so that the blade 24 may project from and retract into both slots 146, 56.

The bottom blade housing 138 slides reciprocatingly in the bore 50 of the inner tube 48 and at least partially under the top blade housing 136. The bottom blade housing 138 is slidably joined to the top blade housing 136 by one or two compression springs 142, one axial end of each of which is connected to a shoulder 148 of the top blade housing 136, and the opposite axial end of each of which is mounted on a respective retaining post 149 extending outwardly from an end wall 150 of the bottom blade housing 138 that faces the shoulder 148 of the top blade housing 136. The bottom blade housing 138 also includes a slot 152 formed in an upper surface thereof, which slot 152 is positioned to be in alignment with the slot 146 of the top blade housing 136. The slot 152 in the bottom blade housing 138 also at least partially receives a portion of the cutting blade 24, as will be described below.

There is a pivot pin 144 that passes transversely through the body of the bottom blade housing 138. This pivot pin 144 holds one end of the cutting blade 24 in place in the slot 152 of the bottom blade housing 138, and allows the cutting blade 24 to pivot thereon and within the slot 152. Similarly, there is an actuator pin 140 which passes transversely through the top blade housing 136 and through the slot 146 formed therein.

The retractable cutting blade 24 includes a forward facing sharpened edge 154 and a rearward facing sharpened edge 156. The blade 24 also includes an opening 158 formed transversely therethrough located generally opposite the cutting edges 154, 156 and at a lower portion of the blade 24. This opening 158 receives the pivot pin 144 of the bottom blade housing 138, and the pivot pin 144 secures the blade 24 to the bottom blade housing 138 but allowing it to pivot thereon.

The retractable cutting blade 24 further includes an arcuate slot 160 formed through the thickness thereof and at an upper portion thereof, nearer the sharpened edges 154, 156 than where the pivot pin opening 158 is located. This arcuate slot 160 is provided for receiving the actuator pin 140 that passes through the top blade housing 136. The actuator pin 140, when received by this arcuate slot 160 formed in the cutting blade 24, causes the cutting blade 24 to move within the slot 146 of the top blade housing 136 between an extended position (when the actuator pin 140 is at or near the bottom end of the arcuate slot 160) and a retracted position (when the actuator pin 140 is located at or near the upper end of the arcuate slot 160).

The compression spring 142 biases the bottom blade housing 138 away from the top blade housing 136. When pressure is exerted on the bottom blade housing 138 by the tip of an endoscope or arthroscope 14 to compress the spring 142, the bottom blade housing 138 moves forward, towards the top blade housing 136. As a result, the cutting blade 24 pivots on the pivot pin 144 of the bottom blade housing 138 and is guided in its movement by the actuator pin 140 situated within the arcuate slot 160 formed therein. Since the top blade housing 136 is fixed within the inner tube 48, movement of the bottom blade housing 138 towards the top blade housing 136 causes the cutting blade 24 to move from a retracted state, with the actuator pin 140 being situated at or near the upper end of the arcuate slot 160 formed in the blade 24, to an extended state, with the actuator pin 140 being located at or near the lower end of the arcuate slot 160 formed through the blade 24, such that the blade 24 extends outwardly of the slot 146 formed in the top blade housing 136 as well as the aligned slot 56 formed in the inner tube 48.

When the tip of the endoscope or arthroscope 14 is withdrawn in the inner tube 48, the compression spring 142 relaxes and causes the bottom blade housing 138 to move away from the top blade housing 136, resulting in the cutting blade 24 being retracted within the slot 146 formed in the top blade housing 136 and the slot 56 formed in the inner tube 48, due to the blade 24 pivoting on the pivot pin 144 and being affixed to the slidable bottom blade housing 138, and with the actuator pin 140 now occupying the top end of the arcuate slot 160 formed in the cutting blade 24. Accordingly, the retraction and extension of the cutting blade 24 through the slot 56 in the inner tube 48 and the slot 22 of the cannula 6 may be easily controlled by the surgeon at any time during a surgical procedure by how far the tip of the endoscope 14 extends into the inner tube 48 of the surgical instrument 2.

More specifically, the surgeon may easily control the extent to which the distal end or tip of the endoscope or arthroscope 14 extends into the inner tube 48 of the surgical instrument 2 by locating the switch 82 on the middle section 10 of the main body assembly 4 in the "SCOPE" position or the "BLADE" position. Even more specifically, when the surgical instrument 2 is in the "SCOPE" position, an endoscope or arthroscope 14 received by the surgical instrument 2 will not extend into the inner tube 48 so far as to actuate the retractable blade assembly 54 and, accordingly, the cutting blade 24 will remain in a retracted position within the inner tube 48. However, by rotating the switch 82 on the main body assembly 4 to the "BLADE" position, the tip or distal end of the endoscope or arthroscope 14 will now engage the retractable blade assembly 54 and, in particular, cause the bottom blade housing 138 to slide against the bias of the compression spring 142 towards the top blade housing 136, causing the cutting blade 24 to extend upwardly through the slot 56 of the inner tube 48 and the slot 22 of the outer cannula 6 to effect the cutting of tissue during a surgical procedure.

A surgical procedure using the endoscopic surgical instrument 2 of the present invention will now be described. By way of example only, the surgical procedure described herein relates to treatment of a patient afflicted with carpel tunnel syndrome in which the flexor retinaculum or transverse carpal ligament is severed in the surgical procedure.

An incision is made just proximal or distal to the transverse carpal ligament, making an entry portal. The distal end 26 of the cannula 6, attached to the surgical instrument 2 or another instrument, such as an endoscope or arthroscope 14, is inserted into the entry portal, and the front edge of the cannula 6 is introduced into the incision and used to create a passage under the carpal transverse ligament, but superficial to the median nerve, with the slot 22 of the cannula 6 facing the transverse carpal ligament. The procedure is observed with the optical system of the endoscope 14. The optical system is moved axially or rotated within the transparent cannula 6, when detached from the surgical instrument 2, to observe and image the target tissue and surrounding tissues. The distal end of the endoscope or arthroscope 14, received by the inner tube 48 of the surgical instrument 2, may view such tissue through the window 58 formed in the inner tube 48, without actuating the retractable blade assembly 54 so that the cutting blade 24 remains retracted within the inner tube 48 of the surgical instrument 2.

The instrument 2, during this procedure of observation of the tissue at the surgical site, is in the "SCOPE" mode to prevent the distal end or tip of the endoscope 14 from inadvertently actuating the retractable blade assembly 54. Also, during this tissue visualization step in the surgical procedure, the transparent cannula 6 may be released from the main body assembly 4 of the surgical instrument 2 by squeezing the diametrically opposed resilient members 40 of the front section 8 together so that the distal end of the endoscope 14 may be rotated within the disassociated cannula 6 and moved axially therein to view all aspects of the surrounding tissue at the surgical site. The optical system of the endoscope 14 is used to visualize not only the transverse carpal ligament but also all surrounding tissue and the location of the median nerve. It should be noted that the slot 22 of the transparent cannula 6, formed on the flat top wall 20 thereof, will remain positioned in alignment to face the transverse carpal ligament and will be in proper position when the blade 24 is extended from the cannula slot 22.

After the visualization step has been performed, as described above, the inner tube 48 of the surgical instrument 2 is repositioned in the cannula 6 such that the blade slot 56 of the inner tube 48 is aligned with the slot 22 formed in the cannula 6 so that the cutting blade 24, when the retractable blade assembly 54 is actuated, will project through both slots 56, 22. The surgical instrument 2 is now switched by the surgeon to the "BLADE" position on the main body assembly 4 thereof. This causes the distal end of the endoscope 14 to engage the retractable blade assembly 54, causing the cutting blade 24 to project outwardly not only from the slot 56 in the inner tube 48 but also the slot 22 of the cannula 6. Even though the angle-cut distal end of the endoscope 14 has moved forward within the inner tube 48 to engage the retractable blade assembly 54, it is still in alignment with the viewing window 58 to observe the tissue being severed at the surgical site.

Also, an advantage of the surgical instrument 2 of the present invention is that it allows the surgeon to extend the cutting blade 24 in any axial position on the cannula 6 such that the transverse carpal ligament may be severed starting from the distal margin thereof or the proximal margin thereof, or any point in between, since the retraction and extension of the cutting blade 24 may be easily controlled by the surgeon during the surgical procedure.

The surgeon may grasp the wing handle 90 of the surgical instrument 2 in one hand while manipulating the switch 82 on the main body assembly 4 of the surgical instrument 2 with the other hand in order to change between the "SCOPE" position, where the cutting blade 24 is retracted within the inner tube 48, and the "BLADE" position, where the cutting blade 24 projects through the slot 56 of the inner tube 48 and the slot 22 of the cannula 6. The blade 24 is extended through the slot 22 of the cannula 6 and the cutting edge 154, 156 of the blade 24 is moved into contact with the transverse carpal ligament. The transverse carpal ligament is severed by either withdrawing the cutting blade 24 or advancing the cutting blade 24 in either axial direction on the cannula 6 which remains detached from the surgical instrument 2 and remains positioned at the surgical site under the transverse carpal ligament.

Alternatively, the cannula 6 may remain fixed to the surgical instrument 2 and, with the blade 24 extended from the slot 22, the cutting edge 156 of the blade 24 is moved into contact with the far margin of the transverse carpal ligament and the transverse carpal ligament is divided by withdrawing the cannula 6 and the surgical instrument 2 towards the entry portal, thereby drawing the cutting edge 156 of the blade 24 through the transverse carpal ligament. The blade 24 may then be retracted back into the cannula 6 when the near margin of the transverse carpal ligament has been reached and severed by switching the surgical instrument 2 to the "SCOPE" position.

After the transverse carpal ligament has been severed, the switch 82 on the surgical instrument 2 may then be rotated by the surgeon to the "SCOPE" position to retract the cutting blade 24 through the cannula slot 22. If, after the cutting operation, and with the cannula 6 detached from the surgical instrument 2 and remaining in place at the surgical site, the endoscope 14, still attached to the surgical instrument 2, may view the surgical site through the transparent cannula 22 and window 58 of the inner tube 48 to visualize the cut edges of the transverse carpal ligament. If any strands of the transverse carpal ligament remain uncut, the blade 24 can then be extended out from the cannula slot 22 again to sever those strands. Alternatively, if the cannula 6 remains attached to the surgical instrument 2 during the cutting procedure and is withdrawn towards the entry portal while the cutting edge 156 of the blade 24, extending through the cannula slot 22, is drawn through the transverse carpal ligament, the cutting blade 24 may then be retracted, and the cannula 6, affixed to the surgical instrument 2, may then be moved back towards the far margin of the transverse carpal ligament through the formed passage, and the optical system of the endoscope 14 is used to visualize the cut edges of the transverse carpal ligament to determine if any strands or sections of the ligament remain uncut.

The surgical instrument 2 of the present invention permits at all times the visualization of the integrity of the underlying median nerve and tendons attached to the digits. While visualizing the nerves and tendons, release is confirmed by passive manipulation of the digits through their range of motion. The cannula 6 is then withdrawn and removed from the entry portal. The cannula 6 is detached from the surgical instrument 2 and properly discarded as medical waste. The wound is closed and a soft bandage is applied. In some cases, a splint is also applied to immobilize the wrist for up to a week.

Figure 29:
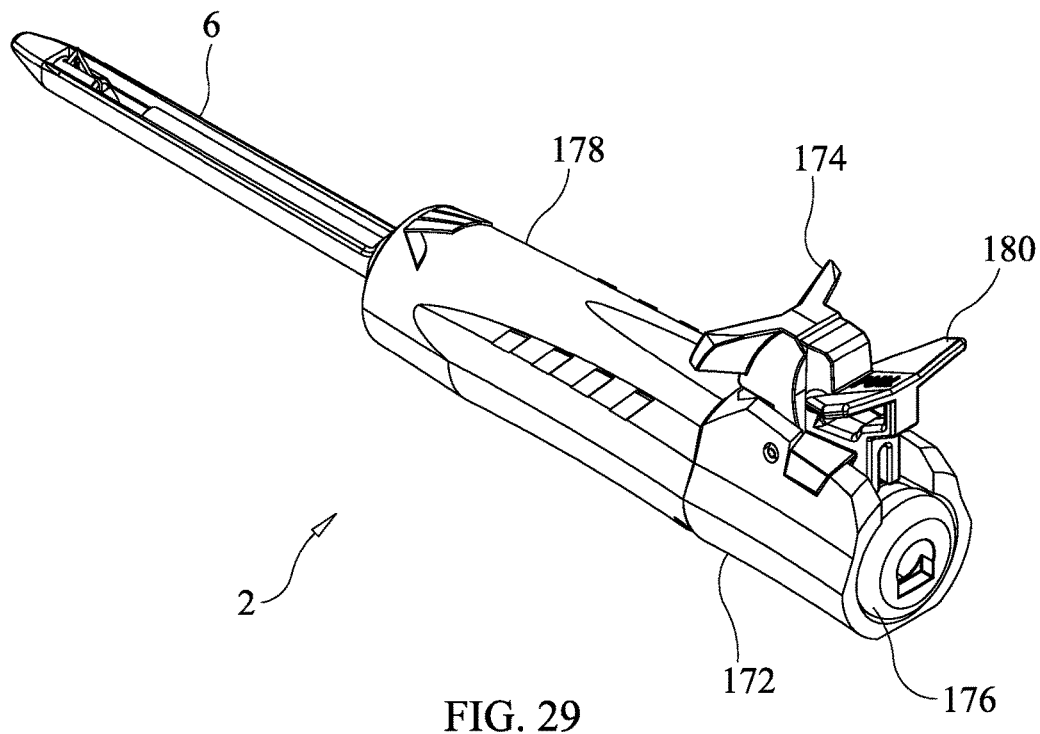
FIG. 29 is a perspective view of a second embodiment of an endoscopic surgical instrument formed in accordance with the present invention.
Figure 126:
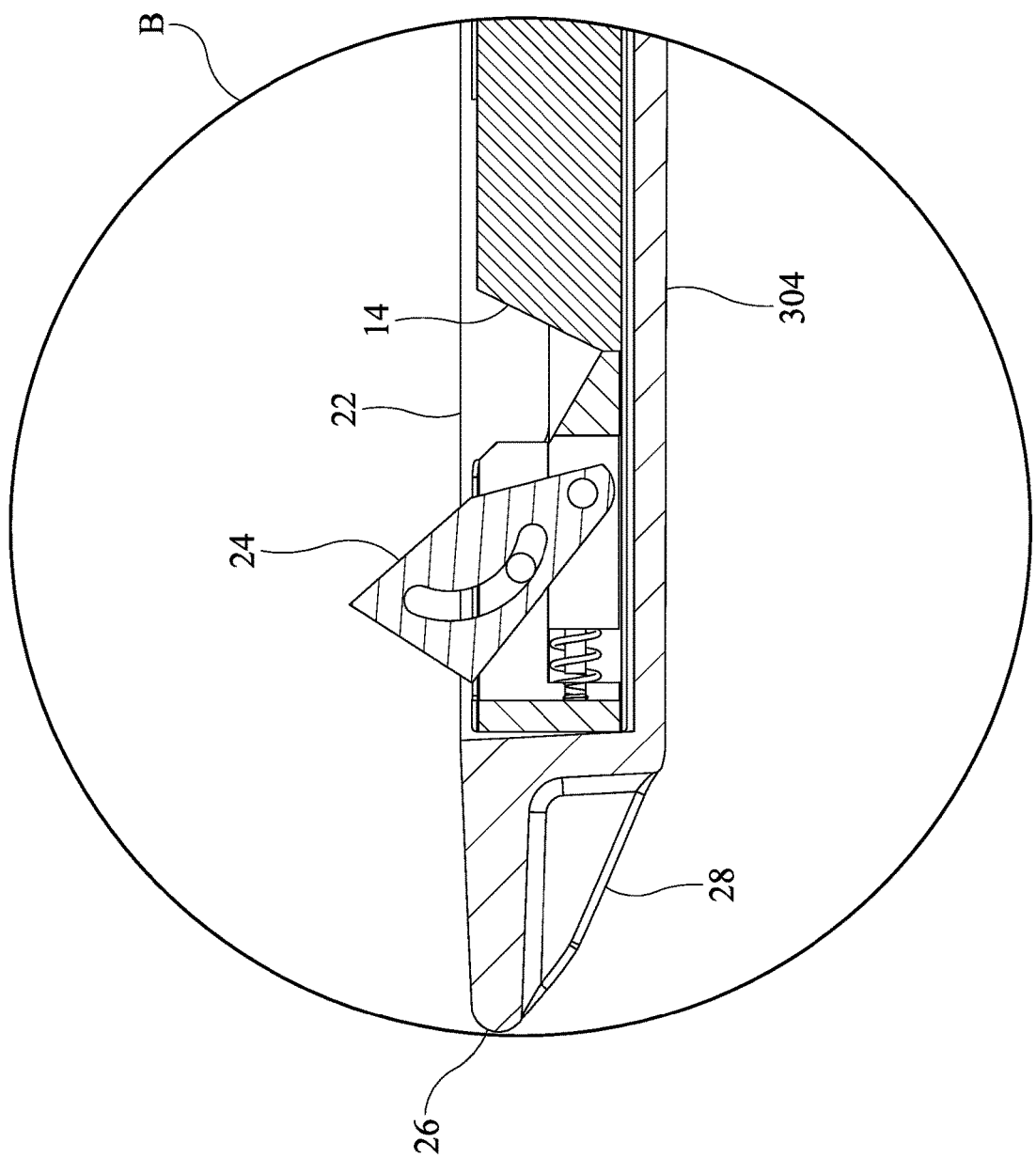

Another version of an endoscopic surgical instrument 2 having a retractable cutting blade 24, constructed in accordance with the present invention, is shown in FIGS. 29-126 of the drawings. In this alternative version of the surgical instrument 2, there are certain components used which are very similar in structure or function to, or have the same structure or function as, components of the surgical instrument 2 described previously and shown in FIGS. 1-28L. Accordingly, such components in this version of the surgical instrument 2 will be referred to with the same reference numbers as used in relation to the same or similar components of the previously described surgical instrument 2.

Figure 30:
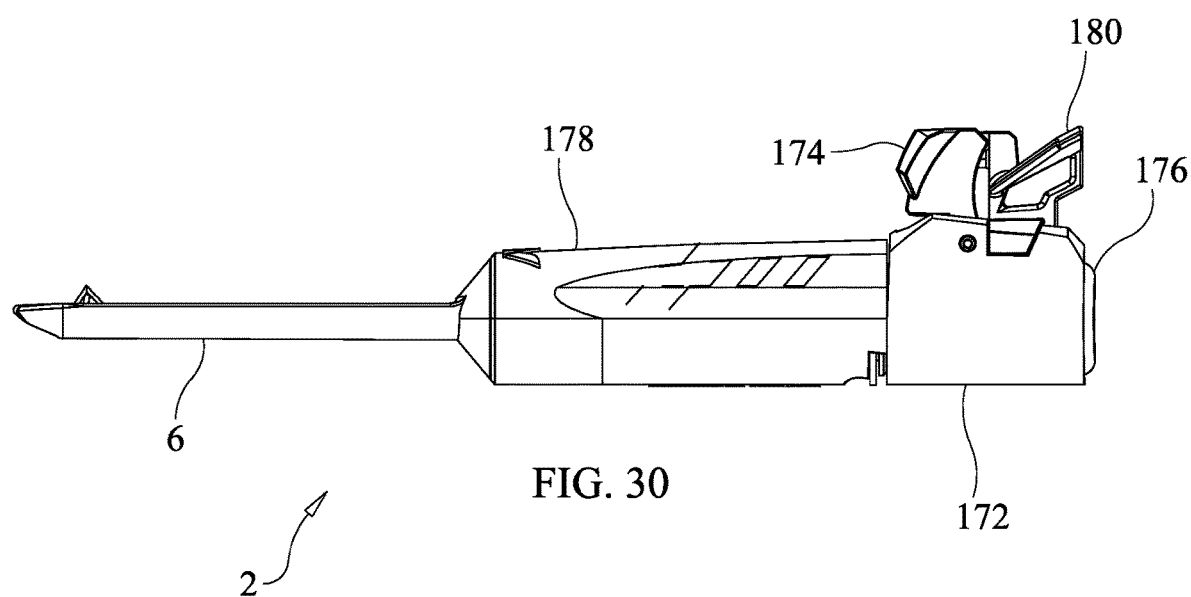
FIG. 30 is a side view of the endoscopic surgical instrument of the present invention shown in FIG. 29.
Figure 31:
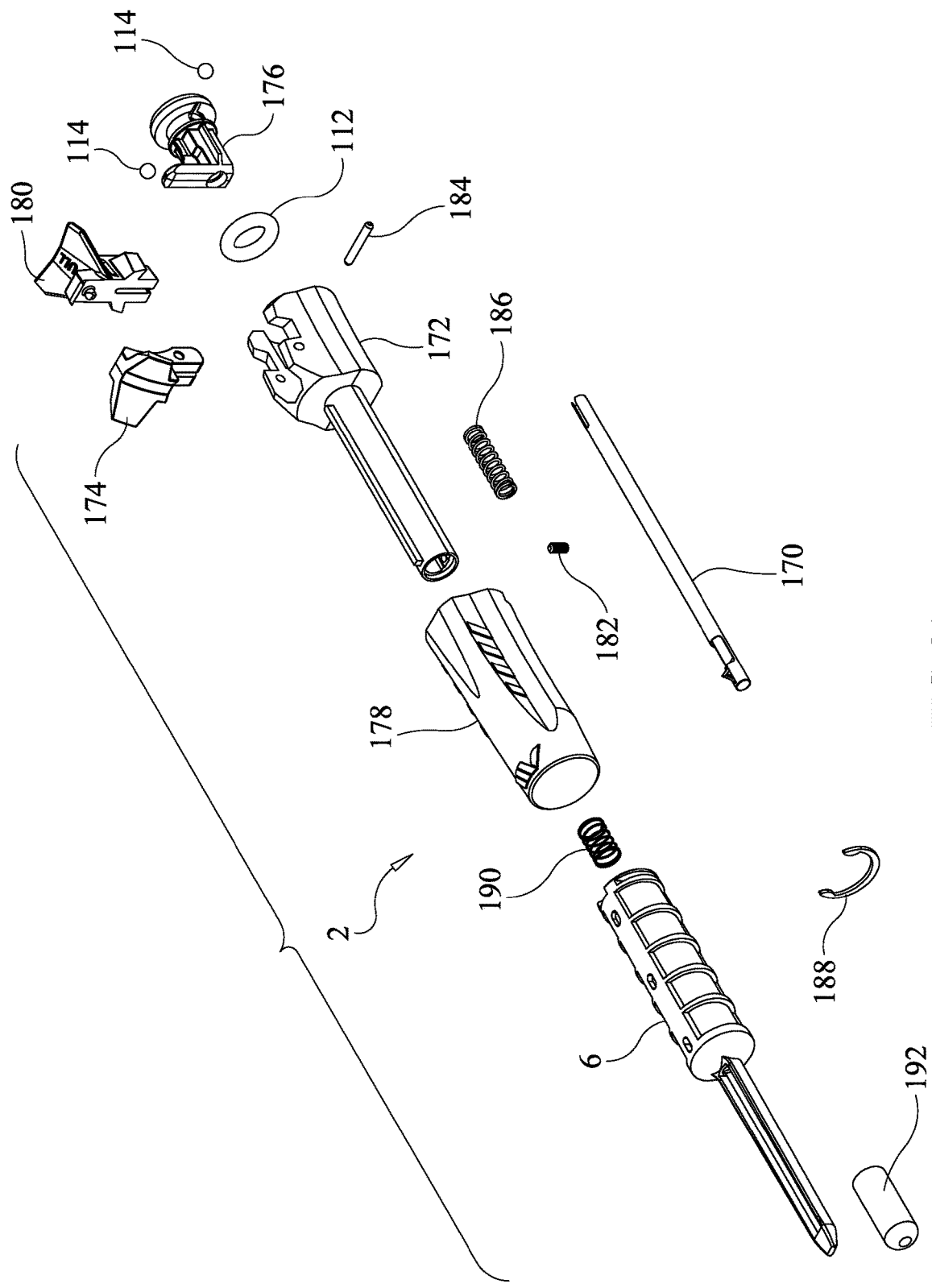
FIG. 31 is an exploded perspective view of the endoscopic surgical instrument of the present invention shown in FIGS. 29 and 30.
Figure 32:
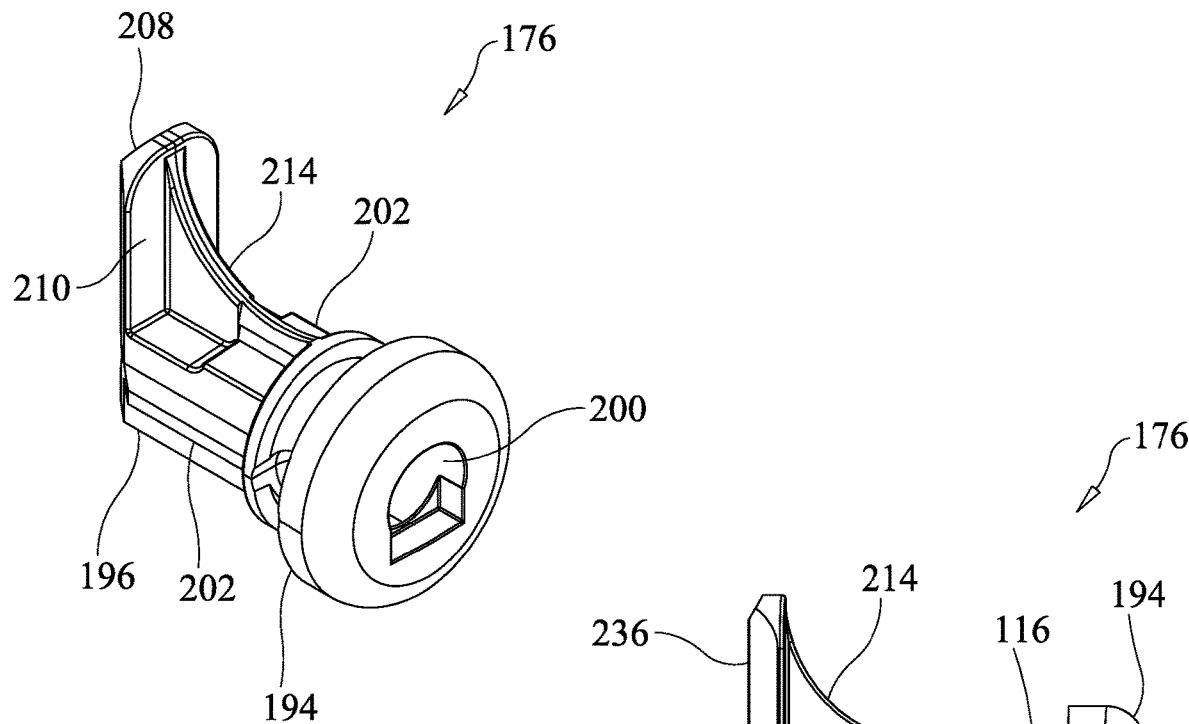
FIG. 32 is a perspective view of a scope coupler forming part of the second embodiment of the endoscopic surgical instrument of the present invention shown in FIGS. 29-31, and further forming part of a scope coupler assembly.
Figure 33:
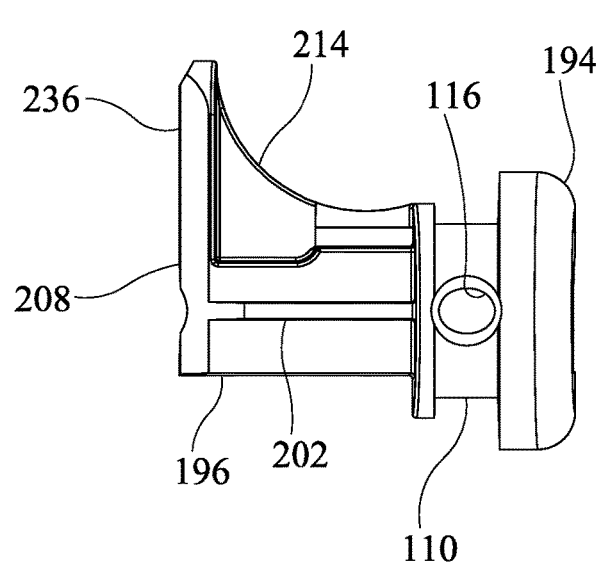
FIG. 33 is a side view of the scope coupler of the present invention shown in FIG. 32.
Figure 34:
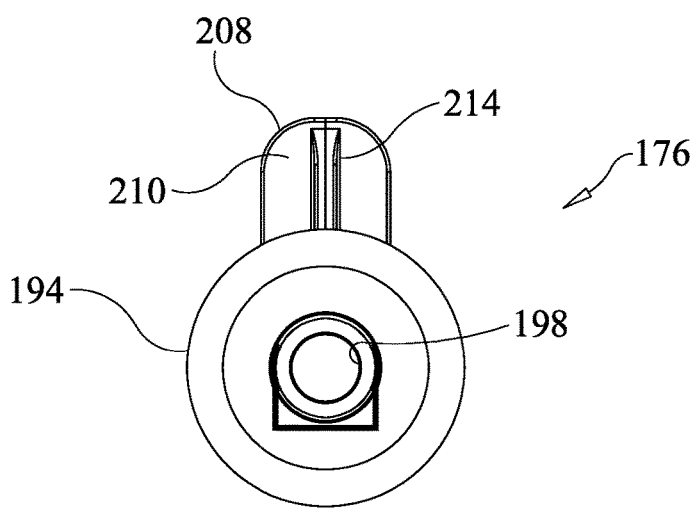
FIG. 34 is a rear view of the scope coupler of the present invention shown in FIGS. 32 and 33.
Figure 35:
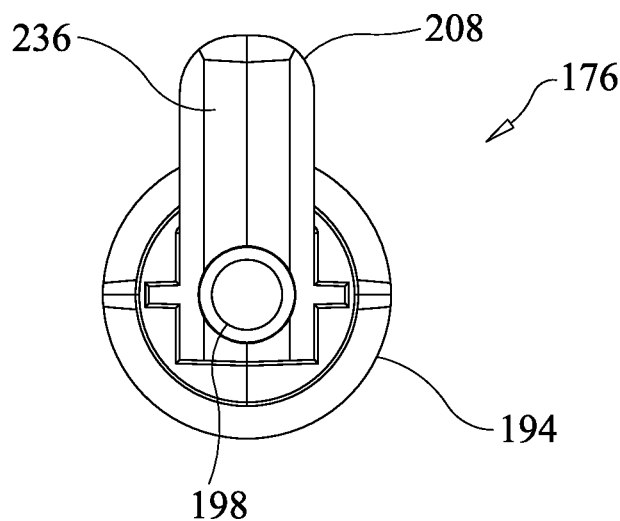
FIG. 35 is a front view of the scope coupler of the present invention shown in FIGS. 32-34.
Figure 36:
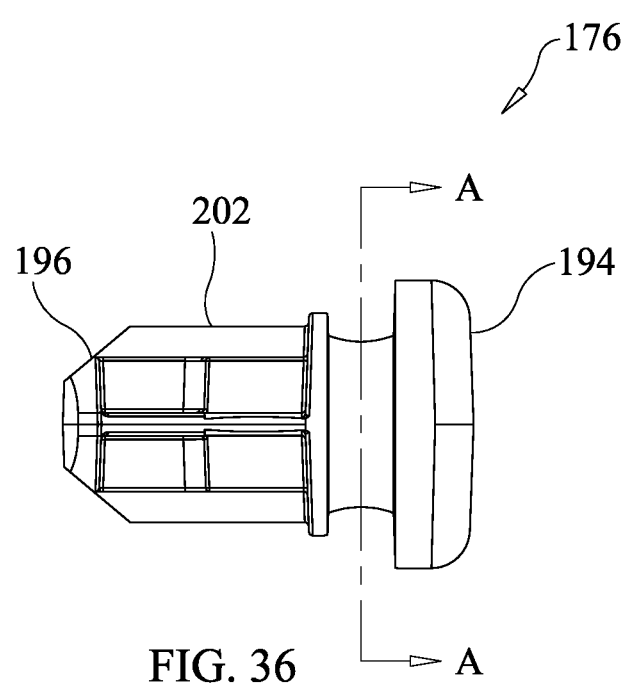
FIG. 36 is a top plan view of the scope coupler of the present invention shown in FIGS. 32-35.
Figure 37:
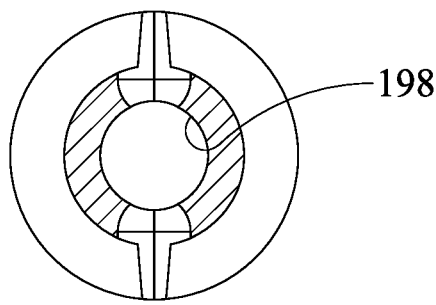
FIG. 37 is a cross-sectional view of the scope coupler of the present invention shown in FIGS. 32-36, taken along line A-A of FIG. 36.
Figure 42:
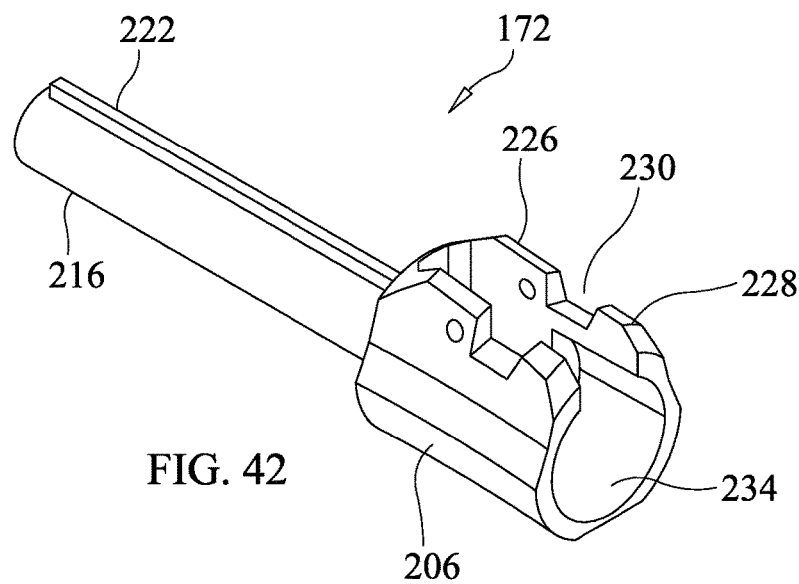
FIG. 42 is a perspective view of a front slide forming part of the second embodiment of the endoscopic surgical instrument of the present invention shown in FIGS. 29-31, and further forming part of a front slide assembly.
Figure 43:
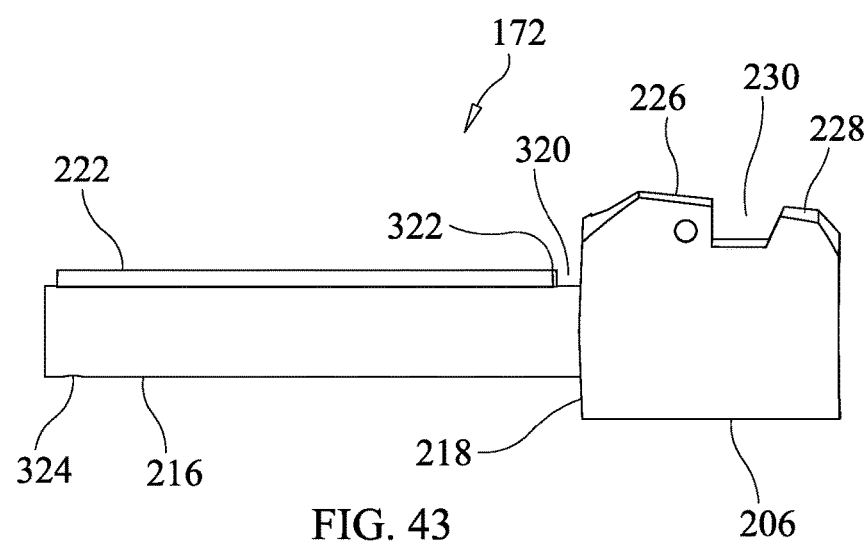
FIG. 43 is a side view of the front slide of the present invention shown in FIG. 42.
Figure 44:
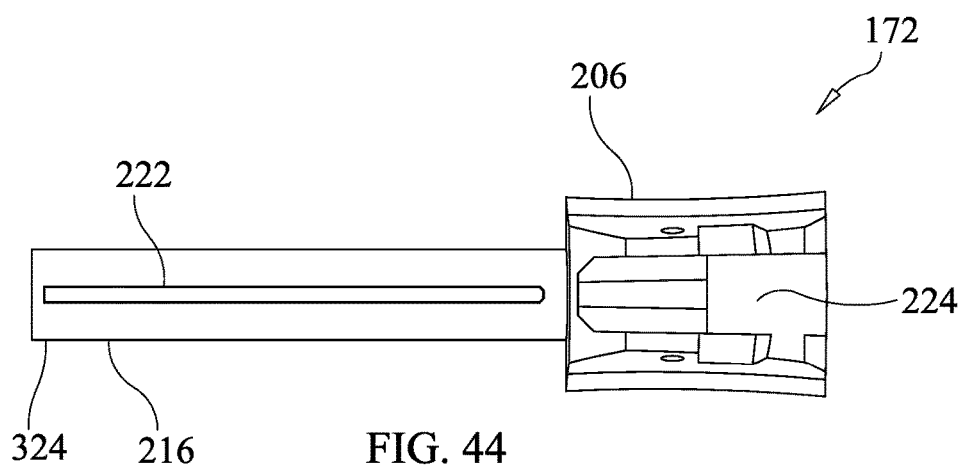
FIG. 44 is a top plan view of the front slide of the present invention shown in FIGS. 42 and 43.
Figure 45:
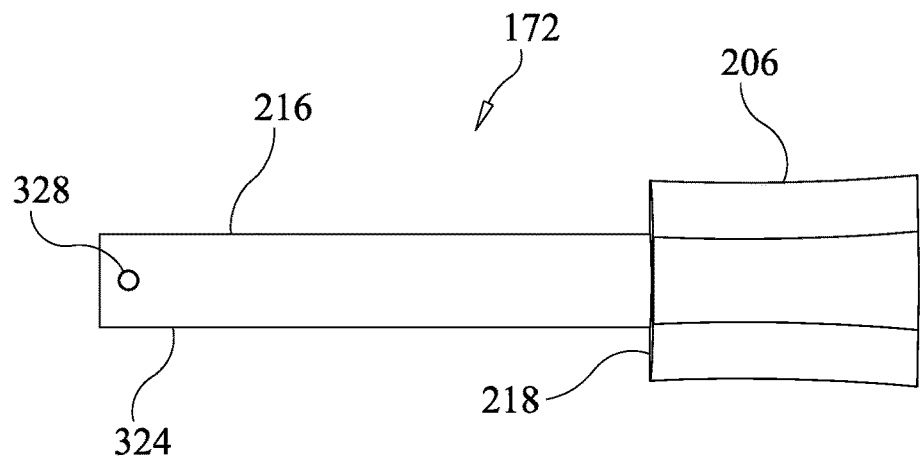
FIG. 45 is a bottom plan view of the front slide of the present invention shown in FIGS. 42-44.
Figure 46:
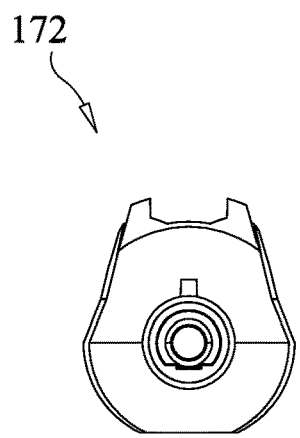
FIG. 46 is a front view of the front slide of the present invention shown in FIGS. 42-45.
Figure 47:
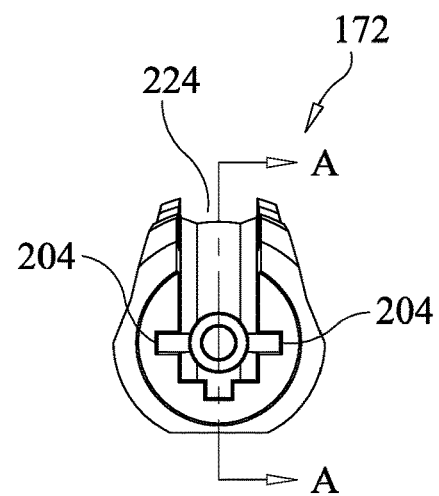
FIG. 47 is a rear view of the front slide of the present invention shown in FIGS. 42-46.
Figure 48:
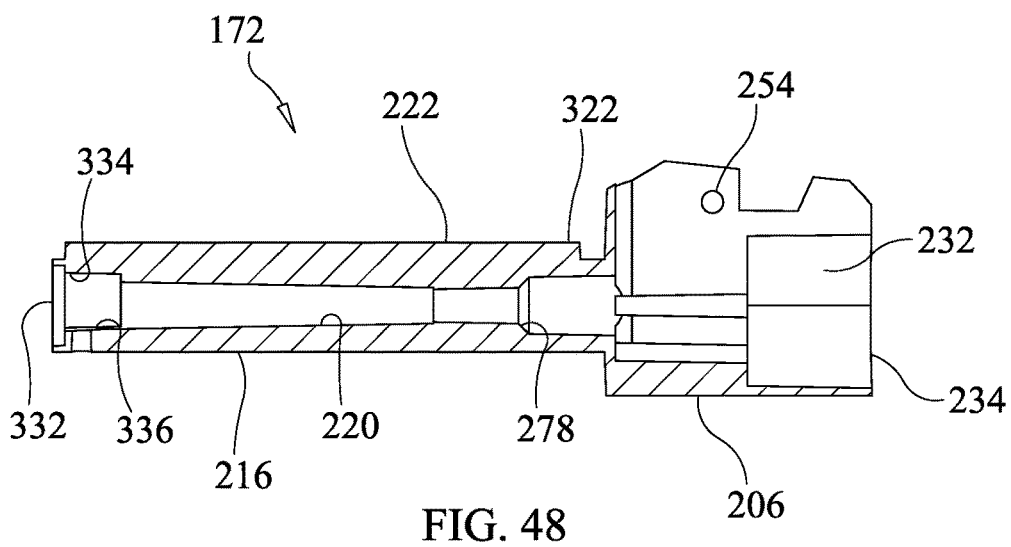
FIG. 48 is a cross-sectional view of the front slide of the present invention shown in FIGS. 42-47, taken along line A-A of FIG. 47.
Figure 52:
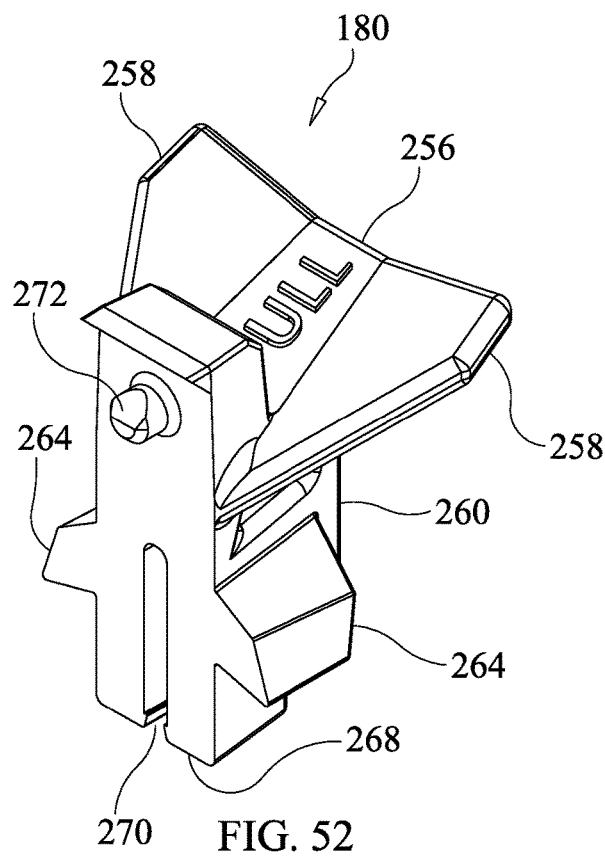
FIG. 52 is a perspective view of a safety piece forming part of the second embodiment of the endoscopic surgical instrument of the present invention shown in FIGS. 29-31.
Figure 53:
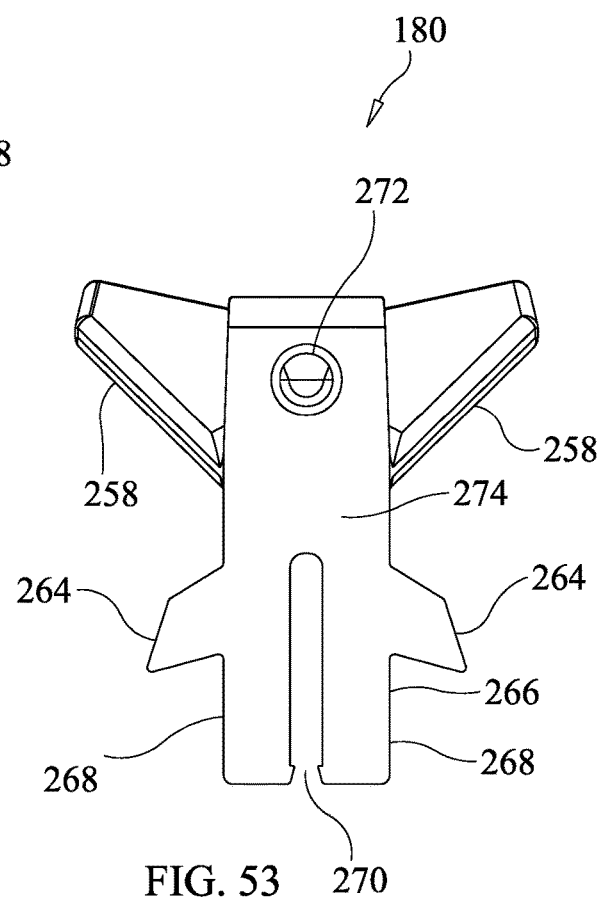
FIG. 53 is a front view of the safety piece of the present invention shown in FIG. 52.
Figure 54:
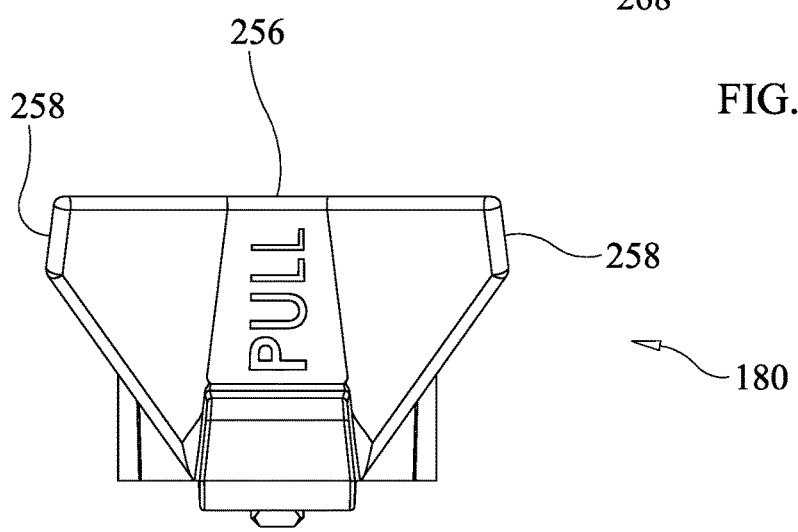
FIG. 54 is a top plan view of the safety piece of the present invention shown in FIGS. 52 and 53.
Figure 55:
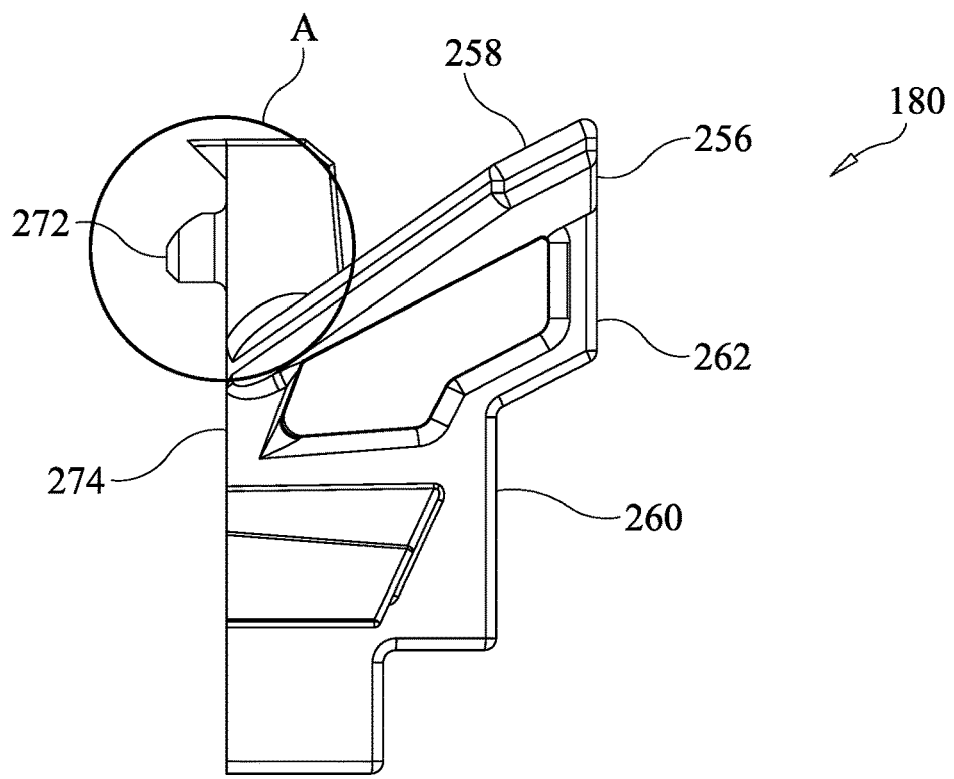
FIG. 55 is a side view of the safety piece of the present invention shown in FIGS. 52-54.
Figure 56:
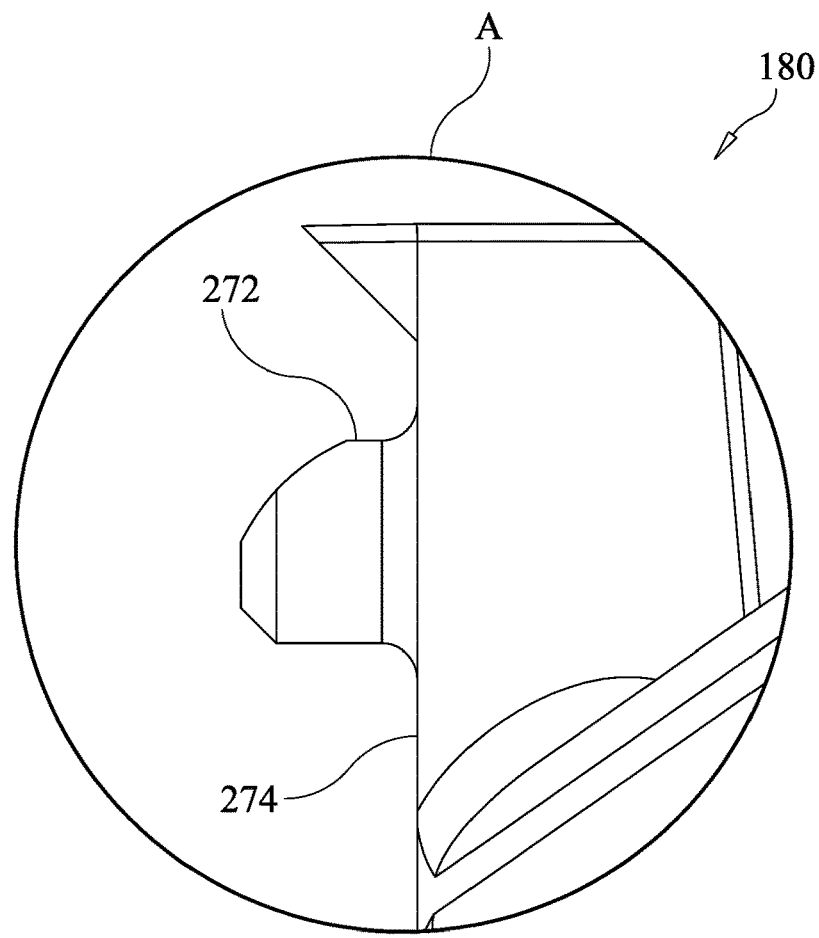
FIG. 56 is a detailed side view of a portion of the safety piece of the present invention shown in FIGS. 52-55, the portion being shown encircled by the circular line A of FIG. 55.

Reference should initially be had to FIGS. 29-31 of the drawings, which show the alternative version of the endoscopic surgical instrument 2 of the present invention in a fully assembled form (FIGS. 29 and 30) and in an exploded view (FIG. 31).

In one form, this alternative embodiment of the surgical instrument 2 of the present invention may include the following components: a blade tube assembly 170, a cannula 6, a front slide 172, a hammer 174, a scope coupler 176, a sleeve 178, a safety piece 180, an O-ring 112, one or more ball bearings 114, a set screw 182, a slotted spring pin 184, a hammer return compression spring 186, a retaining ring 188, a cannula compression spring 190 and an end cap 192. Furthermore, the scope coupler 176, the O-ring 112 and the ball bearings 114, when assembled together, form a scope coupler assembly. When the front slide 172, the hammer 174, the hammer return compression spring 186, the slotted spring pin 184 and the scope coupler assembly are assembled together, they define a front slide assembly. The cannula 6 is joined to the sleeve 178 with the retaining ring 188, and together, with the set screw 182 and the cannula compression spring 190, they define a sleeve/cannula assembly. The blade tube assembly 170 includes a blade tube 48, an alignment ring 60 and a retractable cutting blade assembly 54. The retractable cutting blade assembly 54 includes a top blade housing 136, a bottom blade housing 138, an actuator pin 140, a retractable cutting blade 24, at least one compression spring 142 and a pivot pin 144. The structure of each of these components of the endoscopic surgical instrument 2 of the present invention will now be described in detail, as well as their assembly into a fully constructed surgical instrument 2.

FIGS. 32-41 show one form of a scope coupler 176 of the scope coupler assembly forming part of the endoscopic surgical instrument 2 of the present invention. The scope coupler assembly includes the scope coupler 176, the pair of ball bearings 114 and the O-ring 112. The scope coupler assembly is structured to mate with an endoscope 14 (the term "endoscope" used herein is meant to include arthroscopes and other similarly structured instruments) and hold the endoscope 14 in place on the surgical instrument 2 of the present invention until the endoscope 14 is forcefully removed from the surgical instrument 2.

The scope coupler 176 is a relatively axially short, generally tubular member formed with a cylindrical rear section 194 and a front section 196 having a body shaped generally as a rectangular parallelepiped joined to the cylindrical rear section 194. There is an axial bore 198 formed through the scope coupler 176. The axial bore 198 receives therein through a rear axial opening 200 in communication with the bore 198 the relatively small diameter, elongated, tubular optical section forming the distal end portion of an endoscope 14. An example of an endoscope 14 which is envisioned to be used with the surgical instrument 2 of the present invention is Part No. 0502-104130 manufactured by Stryker Corporation of Kalamazoo, Michigan.

The outer surface of the side wall of the cylindrical rear section 194 of the scope coupler 176 has circumferentially formed therein a circular groove 110 in which is received the O-ring 112. Furthermore, the outer surface of the side wall of the cylindrical rear section 194 of the scope coupler 176 has formed within the groove 110 two radially extending, diametrically opposed openings 116 that communicate with the axial bore 198 formed through the scope coupler 176. Each radially disposed opening 116 receives a respective ball bearing 114 underneath the O-ring 112 seated in the groove 110. At least a portion of the surface of each ball bearing 114 extends into the axial bore 198 of the scope coupler 176.

The purpose of using the combination of an O-ring 112 and one or more ball bearings 114 is to allow an endoscope 14 to be securely retained axially on the surgical instrument 2 of the present invention until forcibly removed therefrom. The embodiment of the surgical instrument 2 of the present invention shown in FIGS. 1-28L and previously described employs essentially the same structure of an O-ring 112 and ball bearings 114 as described above to secure an endoscope 14 on the surgical instrument 2 of the present invention until the endoscope 14 is forcibly removed therefrom.

Figure 122:
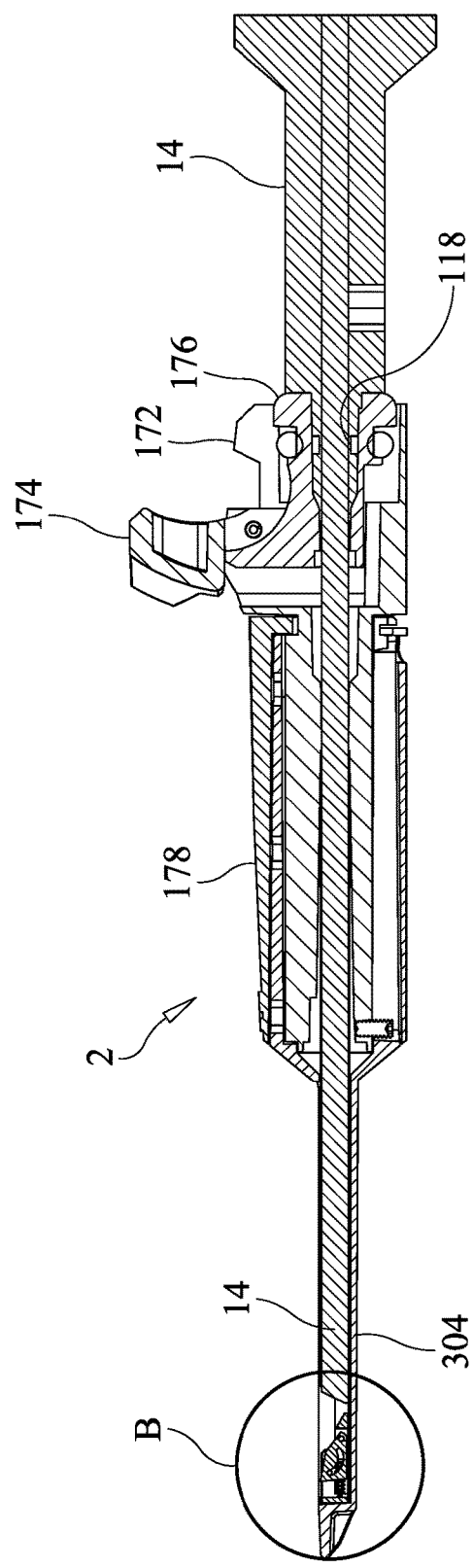
Figure 123:
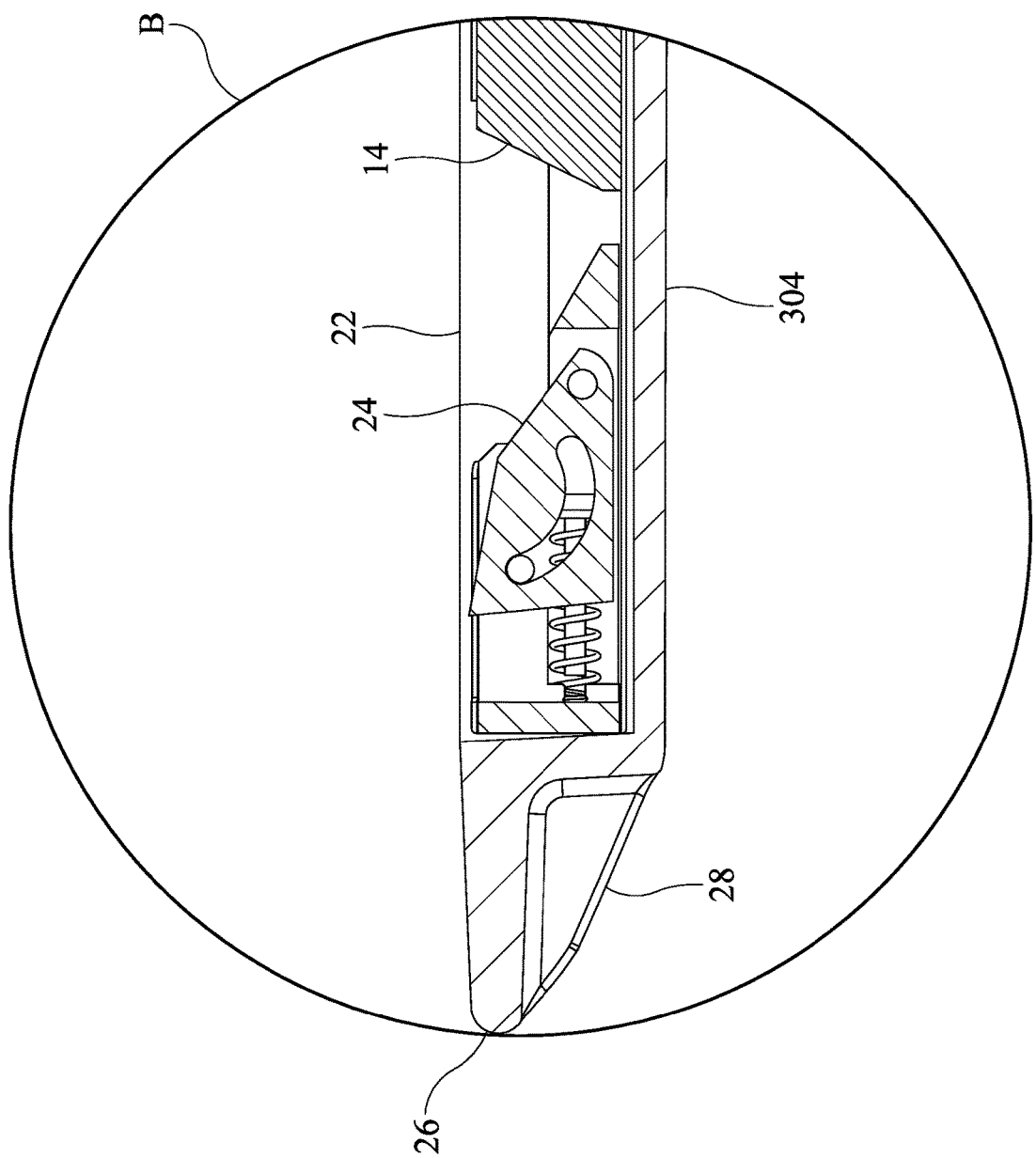
Figure 124:
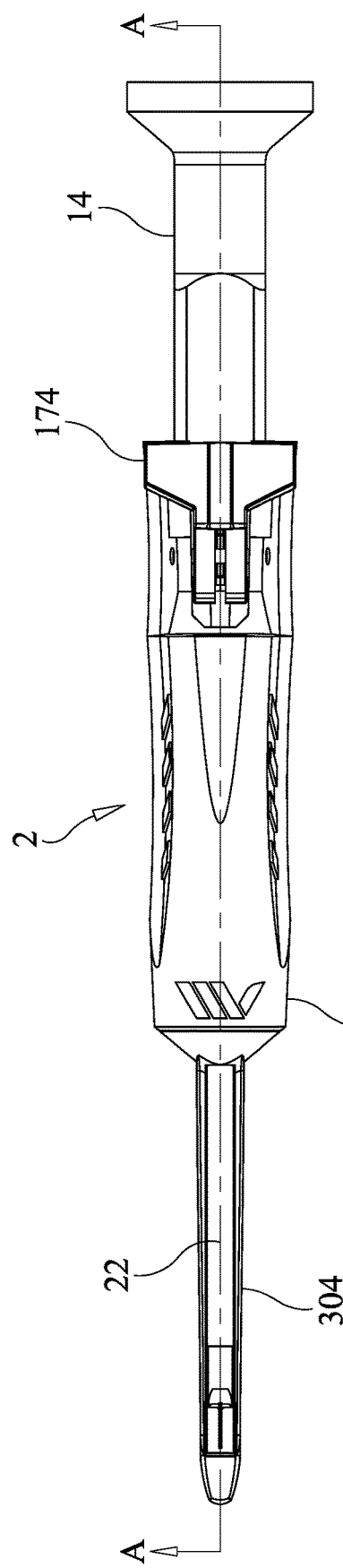
Figure 125:
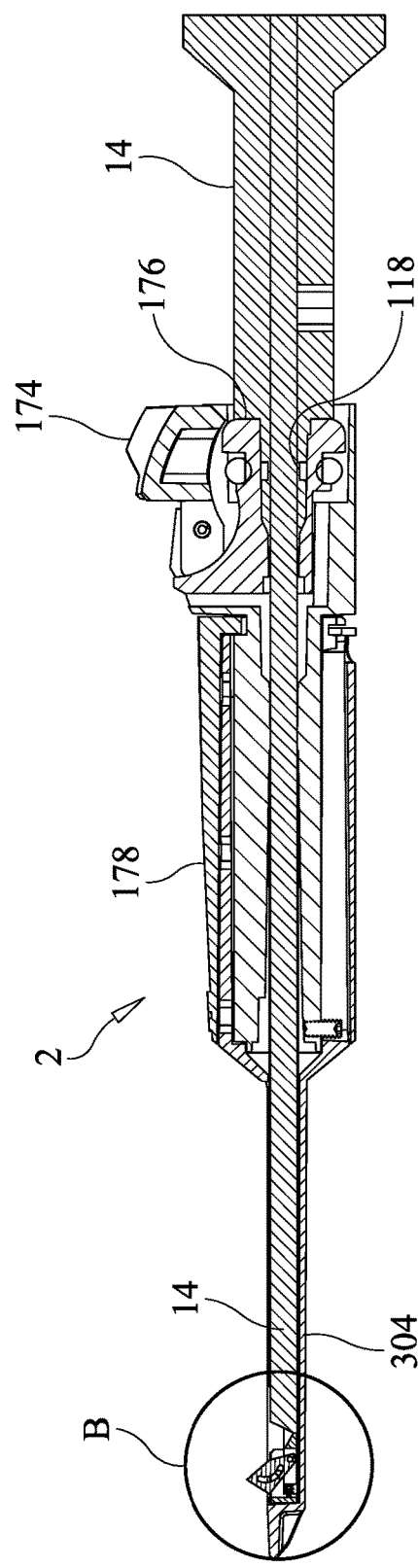

As shown in FIGS. 122 and 124 of the drawings, and as also described previously in relation to the earlier embodiment of the surgical instrument 2 of the present invention and shown in FIG. 6, many endoscopes 14 have a circular groove 118 formed in a cylindrical outer wall near the proximal end thereof. When the endoscope 14 is inserted into the scope coupler 176 of the surgical instrument 2, the groove 118 on the endoscope 14 is aligned with the ball bearings 114 partially protruding from their respective openings 116 radially into the bore 198 on the scope coupler 176. The endoscope 14 is pushed axially by the surgeon into the axial bore 198 of the scope coupler 176 until portions of the ball bearings 114 come to rest in the groove 118 of the endoscope 14, selectively locking the endoscope 14 in a proper position on the surgical instrument 2 of the present invention. The endoscope 14 may be removed axially from the surgical instrument 2 by overcoming the force exerted thereon by the ball bearings 114, biased radially inwardly by O-ring 112 of the surgical instrument 2. The O-ring 112 retains the ball bearings 114 in place in their respective openings 116 on the scope coupler 176 yet allows radial movement of the ball bearings 114 when the endoscope 14 is inserted into or removed from the surgical instrument 2.

The rectangular body of the front section 196 of the scope coupler 176 includes a pair of axially extending fins or ribs 202 protruding outwardly from opposite lateral side walls of the body of the front section 196. As will be explained in greater detail, these fins or ribs 202 will be slidably received by respective oppositely disposed slots 204 formed in the rear main body 206 of the front slide 172 when the scope coupler 176 and front slide 172 are assembled together.

The front section 196 of the scope coupler 176 also includes a strike plate 208 formed as an upstanding planar wall affixed to or integrally formed with the body of the front section 196 and extending perpendicularly to the longitudinal axis of the scope coupler 176 at the distal end thereof opposite the cylindrical rear section 194. As will be further described, this strike plate 208 provides a rear bearing surface 210 contacted by a pivoting lower end portion 212 of the hammer 174 to move the scope coupler 176, and an endoscope 14 attached thereto, in a forward or rearward direction with respect to the front slide 172 when the scope coupler 176 is coupled thereto. The scope coupler 176 also includes a knee brace 214 joined to and extending outwardly from the upper side wall of the body of the front section 196 and the rear bearing surface 210 of the strike plate 208. The purpose of the knee brace 214 is to strengthen the connection of the strike plate 208 to the body of the front section 196, since the hammer 174, when pivoted, exerts a force on the strike plate 208. The opposite bottom wall of the body of the front section 196 of the scope coupler 176 is substantially flat.

The front slide 172 of this alternative version of the surgical instrument 2 of the present invention is shown in FIGS. 42-48. The front slide 172 includes a rear main body 206 and a front section formed as an elongated, tubular member 216 extending axially outwardly from a front wall 218 of the rear main body 206. The tubular member 216 of the front slide 172 has a bore 220 extending axially therethrough. The outer surface of the tubular member 216 of the front slide 172 includes a guide rib 222 protruding outwardly therefrom and extending axially along at least a portion of the axial length thereof.

The rear main body 206 of the front slide 172 is generally U-shaped in transverse cross-section and includes an outer side wall which is rounded at the bottom of the body 206 and which extends upwardly to define a relatively wide slot or opening 224 at the top of the main body 206 that is straddled by laterally opposite, upwardly extending, spaced apart front arms 226 and rear arms 228, the front and rear arms 226, 228 on respective lateral sides of the top opening 224 defining a space 230 therebetween for receiving portions of the safety piece 180, as will be explained in greater detail. The rear main body 206 is further formed with an internal bore 232, which communicates with the axial bore 220 of the tubular front section 216 and which extends to the rear end of the main body 206 to define an open side 234 thereat. The internal bore 232 of the rear main body 206 is dimensioned to slidably receive at least a portion, or all, of the axial length of the scope coupler 176 through the rear open side 234 thereof when the two components 172, 176 are assembled together. More specifically, the diameter of the internal bore 232 of the rear main body 206 is greater than that of the axially extending bore 220 of the tubular front section 216. Furthermore, the internal bore 232 of the rear main body 206 of the front slide 172 communicates with the top opening 224 of the rear main body 206.

All or a front portion of the scope coupler 176 is received by the enlarged internal bore 232 of the rear main body 206 of the front slide 172 through the rear open side 234 thereof, the scope coupler 176 being oriented such that the front surface 236 of the strike plate 208, which is opposite the rear bearing surface 210 thereof, faces toward the front of the rear main body 206 and the tubular front section 216 of the front slide 172. Furthermore, the axial bore 198 of the scope coupler 176 is axially in alignment with the axial bore 220 of the tubular front section 216 and the enlarged internal bore 232 of the rear main body 206 when the scope coupler 176 and the front slide 172 are assembled together. In this manner, the optical viewing distal end of an endoscope 14 may pass through the axial bores 198, 220, 232 of the scope coupler 176 and the front slide 172 when the endoscope 14 is mounted on the surgical instrument 2 of the present invention.

An inner wall of the rear main body 206 of the front slide 172 which defines the enlarged internal bore 232 has formed therein two diametrically opposed slots 204. These slots 204 receive respective fins 202 formed on the front section 196 of the scope coupler 176 when the scope coupler 176 is received by the internal bore 232 of the rear main body 206 of the front slide 172. The slots 204 not only allow the scope coupler 176 to move reciprocatingly within the enlarged internal bore 232 of the rear main body 206 of the front slide 172, but also help maintain the proper orientation and alignment of the scope coupler 176, and an endoscope 14 coupled thereto, with respect to the front slide 172 and, more generally, the surgical instrument 2.

The hammer 174 of the surgical instrument 2 of the present invention is shown in FIGS. 49-51. The hammer 174 is structured with a main body having a forked or clevis-like lower portion 212 formed of two parallelly extending, spaced apart legs 240 defining a slot 238 therebetween, and an opposite upper portion 242. The upper portion 242 includes a concave curved rear wall 244 and an opposite front wall 246 from which extends generally laterally outwardly a double wing handle 248 formed as protruding planar members 250 extending angularly in opposite directions from the front wall 246. A surgeon performing a surgical procedure may use his thumb of either his left hand or his right hand to engage one of the planar members 250 of the double wing handle 248 to facilitate not only axial movement of the endoscope 14 relative to the surgical instrument 2 but also the retraction or protrusion of the cutting blade 24 through a slot 22 formed in the cannula 6, as will be described in greater detail.

Figure 115:
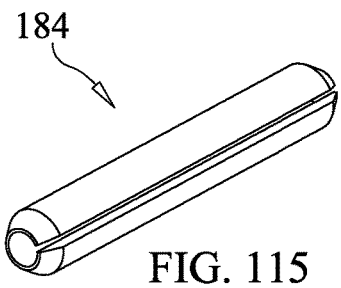
FIG. 115 is a perspective view of a slotted spring pin forming part of the second embodiment of the endoscopic surgical instrument of the present invention shown in FIGS. 29-31, and further forming part of the front slide assembly.
Figure 116:
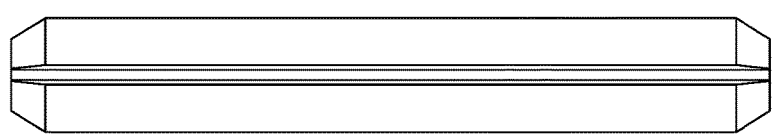
FIG. 116 is a side view of the slotted spring pin of the present invention shown in FIG. 115.
Figure 117:
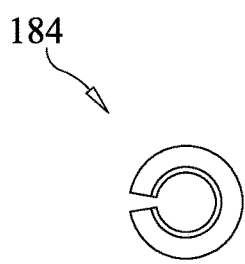

The main body of the hammer 174, and more preferably, the legs 240 of the lower portion 212 thereof include a bore or bores 252 formed laterally therethrough, which bore or bores 252 receive the slotted spring pin 184 (see FIGS. 115-117) to pivotally mount the hammer 174 to the front slide 172. More specifically, the upwardly extending front arms 226 situated on opposite sides of the top opening 224 formed in the rear main body 206 of the front slide 172 include openings 254 formed through their thicknesses which also receive the slotted spring pin 184 which passes through the hammer 174. When constructing the front slide assembly, the scope coupler 176 is first received by the enlarged internal bore 232 of the rear main body 206 of the front slide 172 through the rear open side 234 thereof. Then, the hammer 174 is received through the top opening 224 formed in the rear main body 206, with the spaced apart legs 240 and slot 238 of the forked lower portion 212 of the main body of the hammer 174 straddling the upwardly extending knee brace 214 of the scope coupler 176 and such that the laterally extending, pin-receiving bore or bores 252 of the hammer 174 are situated in alignment with the openings 254 formed in the opposite, upwardly extending front arms 226 of the rear main body 206 of the front slide 172. The slotted spring pin 184 is received through the arm openings 254 of the front slide 172 and the laterally extending bore or bores 252 of the hammer 174 to pivotally secure the hammer 174 in place on the front slide 172, with the upper portion 242 of the hammer 174 and the double wing handle 248 extending outwardly of the top opening 224 formed in the rear main body 206 of the front slide 172. When assembled in this manner, the legs 240 of the hammer 174 will engage the rear bearing surface 210 of the strike plate 208 of the scope coupler 176 when the double wing handle 248 is pivoted rearwardly downwardly by the surgeon using finger pressure. This causes the forked lower portion 212 of the hammer 174 to exert pressure on the rear bearing surface 210 of the strike plate 208 of the scope coupler 176, resulting in the distal end of an endoscope 14 attached to the scope coupler 176 of the surgical instrument 2 to move axially forward through the bore 220 of the tubular front section 216 of the front slide 172 which, in turn, will cause the cutting blade 24 to extend outwardly through an elongated slot 22 formed in the top wall 20 of the cannula 6, as will be described in greater detail.

In summary, the hammer 174 may reside in at least two positions on the front slide 172. In a first position in which the hammer 174 is disposed substantially upright on the front slide 172, the lower portion 212 of the hammer 174 may engage, but does not exert a forward force on, the strike plate 208 such that an endoscope 14 attached to the surgical instrument 2 by way of the scope coupler 176 is in a first relatively rearward axial position relative to the surgical instrument 2. In this rearward position, the distal tip of the endoscope 14 will not engage, or will not sufficiently engage, the retractable cutting blade assembly 54 to cause the cutting blade 24 to protrude from the cannula slot 22, as will be described in greater detail. Thus, the cutting blade 24 will remain retracted within the surgical instrument 2. The first position of the hammer 174 described above may be referred to herein as the "blade retracted position". However, when the hammer 174 is pivoted downwardly and rearwardly to reside in a second position, the lower portion 212 of the hammer 174 exerts a force on the strike plate 208 and forces the scope coupler 176, and an endoscope 14 coupled to the scope coupler 176, forward on the surgical instrument 2 such that the endoscope 14 is now in a second, relatively more forward axial position relative to the surgical instrument 2. In this forward position, the distal tip of the endoscope 14 will now engage the retractable cutting blade assembly 54 sufficiently to cause the cutting blade 24 to protrude from the cannula slot 22 of the surgical instrument 2, as will be described in greater detail. The second position of the hammer 174 described above may be referred to herein as the "blade extended position".

To prevent the hammer 174 from inadvertently pivoting rearwardly on the front slide 172, which causes the retractable cutting blade 24 to protrude through the cannula slot 22, a safety piece 180 is provided, which is shown in FIGS. 52-56. The safety piece 180 is preferably in a noticeable color, such as bright yellow, green or orange, so that it is distinguishable and different from the color of the sleeve 178, front slide 172 and scope coupler 176 of the instrument 2. In this way, a surgeon will easily recognize that the safety piece 180 is in place on the surgical instrument 2, rendering the instrument 2 inoperable and safe to handle.

The safety piece 180 has a main body, with a wing handle 256 formed by two triangular planar members 258 extending outwardly from the rear wall 260 of the main body and at the upper portion 262 thereof. With this configuration, the wing handle 256 is easily graspable by a surgeon so that it may be forcibly removed from the instrument 2 prior to a surgical procedure, allowing the hammer 174 to pivot on the front slide 172 on which the hammer 174 is mounted. The main body of the safety piece 180 also has two shoulders 264 projecting outwardly from opposite lateral side walls of the main body. The lower portion 266 of the main body is split to define two legs 268 which are separated from each other by a slot 270. Like the legs 240 of the hammer 174, the legs 268 of the safety piece 180 straddle the knee brace 214 of the scope coupler 176, with knee brace 214 being received by the slot 270 between the legs 268, when the safety piece 180 is mounted on the front slide 172.

The safety piece 180 is removably received in the top opening 224 of the rear main body 206 of the front slide 172, directly behind and engaging the rear wall 244 of the hammer 174. When in place on the front slide 172, the safety piece 180 prevents the hammer 174 from pivoting from the blade retracted position to the blade extended position. The outwardly extending shoulders 264 rest on the top edges of the outer side wall of the rear main body 206 and in opposite spaces 230 defined between the adjacent front and rear arms 226, 228 on each side of the top opening 224 so that the surgeon knows that the safety piece 180 is fully received and properly mounted on the front slide 172, rendering the surgical instrument 2 inoperable and preventing the safety piece 180 from inadvertently falling out of the top opening 224 formed in the rear main body 206 of the front slide 172 during shipment or misuse of the surgical instrument 2.

As a further precaution, the safety piece 180 may include a protrusion or nub 272, projecting outwardly from the front wall 274 of the main body at the upper portion 262 thereof. When the safety piece 180 is properly seated in the top opening 224 of the rear main body 206 of the front slide 172, directly behind and engaging the hammer 174, the projecting nub 272 of the safety piece 180 is received by a slot or elongated recess 276 formed in the rear wall 244 of the hammer 174 that faces the front wall 274 of the safety piece 180, essentially coupling the safety piece 180 to the hammer 174, so that the safety piece 180 is even more securely mounted on the rear main body 206 of the front slide 172 of the surgical instrument 2 unless forcibly removed from the front slide 172, to further ensure that the safety piece 180 will not inadvertently fall out of the top opening 224 in the rear main body 206 of the front slide 172 no matter what disposition the surgical instrument 2 is in or what impacts the instrument 2 receives during shipment.

Figure 57:
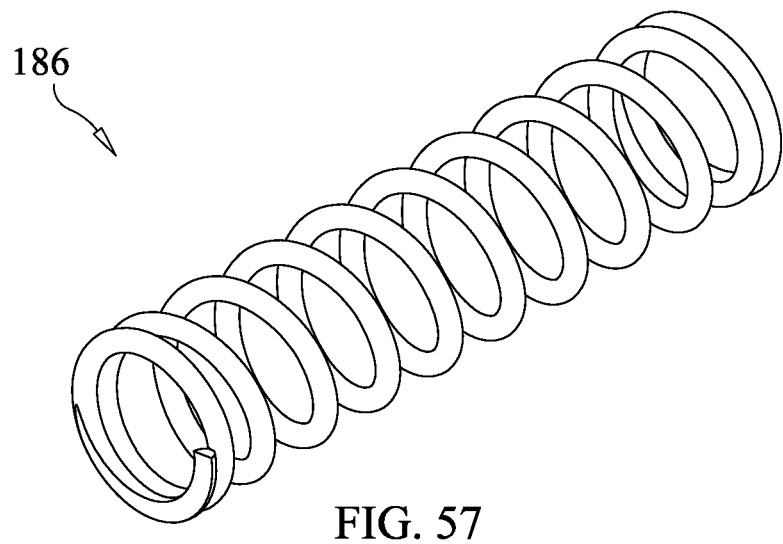
FIG. 57 is a perspective view of a hammer return compression spring forming part of the second embodiment of the endoscopic surgical instrument of the present invention shown in FIGS. 29-31, and further forming part of the front slide assembly.
Figure 58:
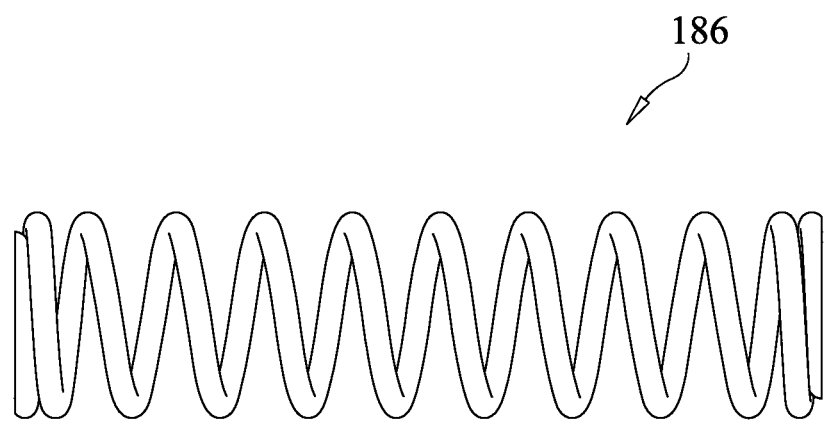
FIG. 58 is a side view of the hammer return compression spring of the present invention shown in FIG. 57.
Figure 59:
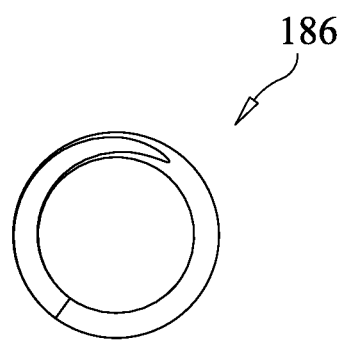
FIG. 59 is an end view of the hammer return compression spring of the present invention shown in FIGS. 57 and 58.
Figure 60:
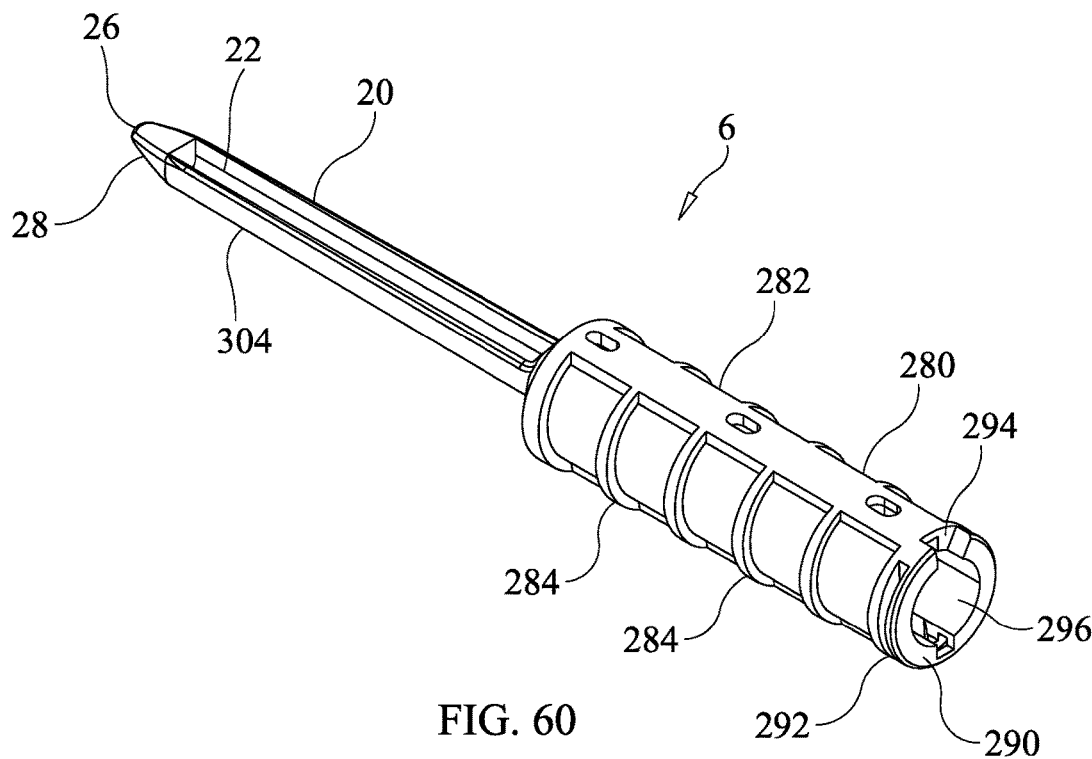
FIG. 60 is a perspective view of a cannula forming part of the second embodiment of the endoscopic surgical instrument of the present invention shown in FIGS. 29-31, and further forming part of a sleeve/cannula assembly.
Figure 61:
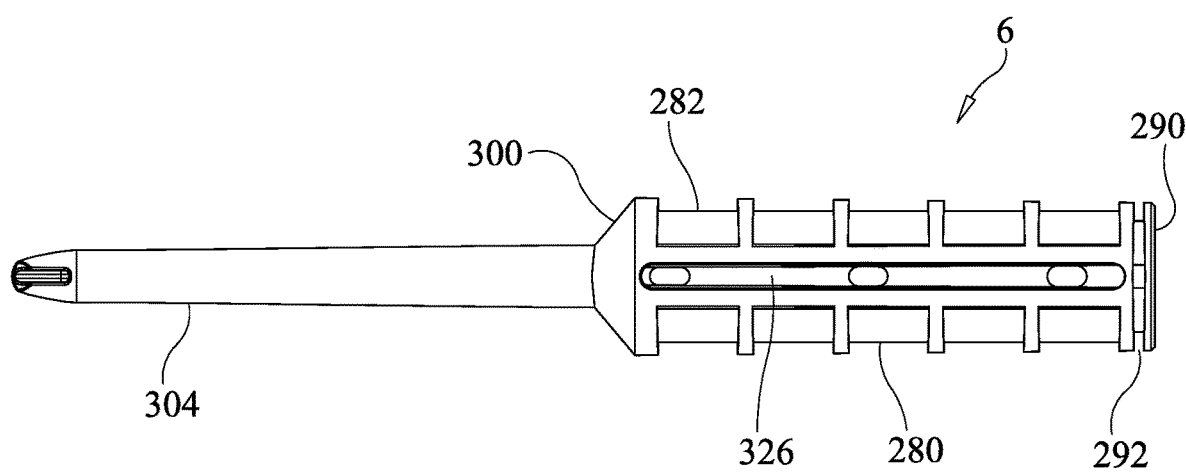
FIG. 61 is a bottom plan view of the cannula of the present invention shown in FIG. 60.
Figure 65:
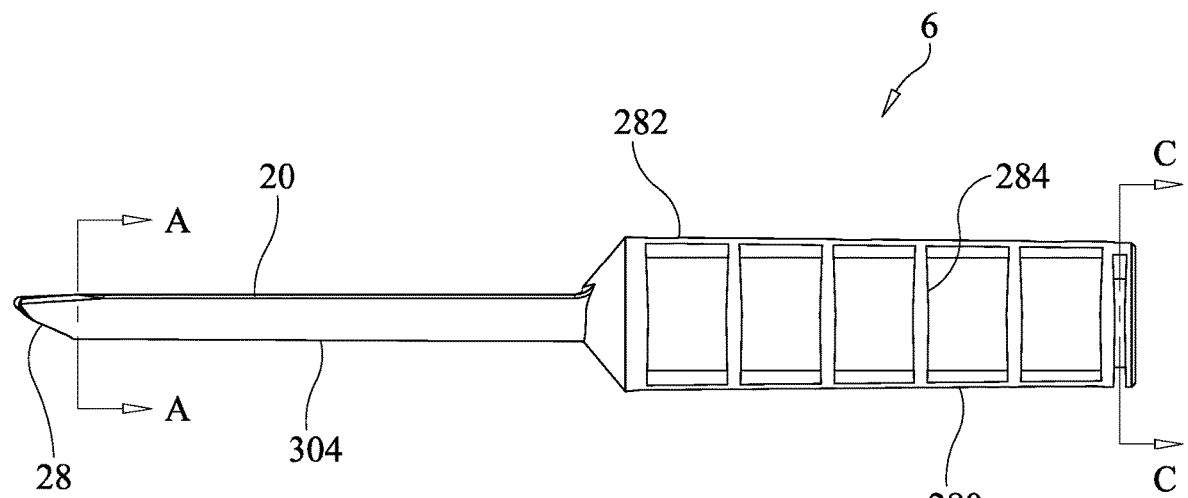
FIG. 65 is a side view of the cannula of the present invention shown in FIGS. 60-64.
Figure 66:
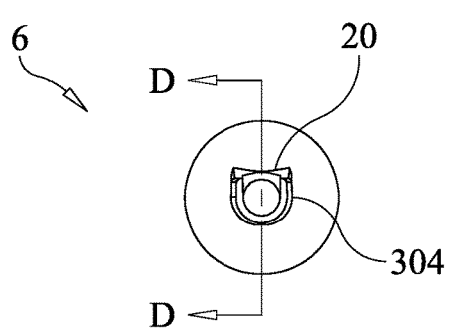
FIG. 66 is a cross-sectional view of the cannula of the present invention shown in FIGS. 60-65, taken along line A-A of FIG. 65.
Figure 67:
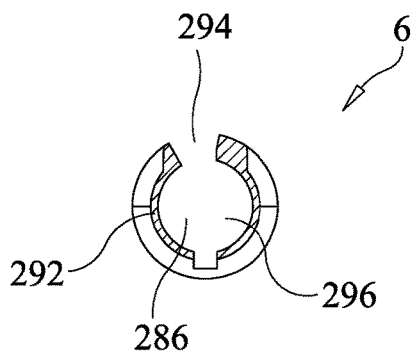
FIG. 67 is a cross-sectional view of the cannula of the present invention shown in FIGS. 60-66, taken along line D-D of FIG. 66.
Figure 68:
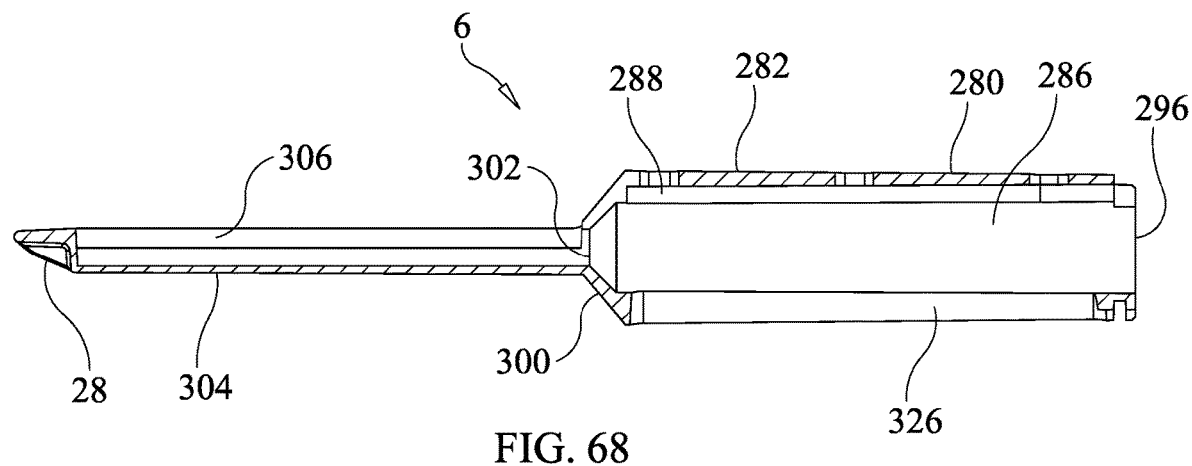
FIG. 68 is a cross-sectional view of the cannula of the present invention shown in FIGS. 60-67, taken along line C-C of FIG. 65.
Figure 69:
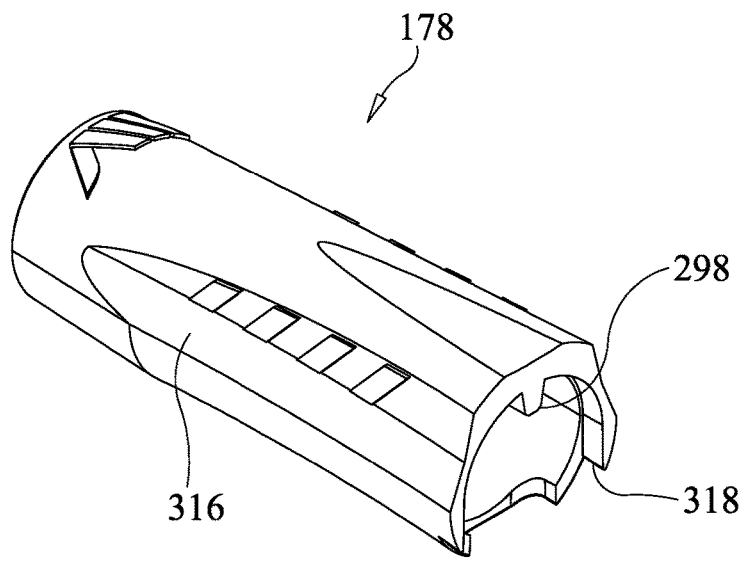
FIG. 69 is a perspective view of a sleeve forming part of the second embodiment of the endoscopic surgical instrument of the present invention shown in FIGS. 29-31, and further forming part of the sleeve/cannula assembly.
Figure 70:
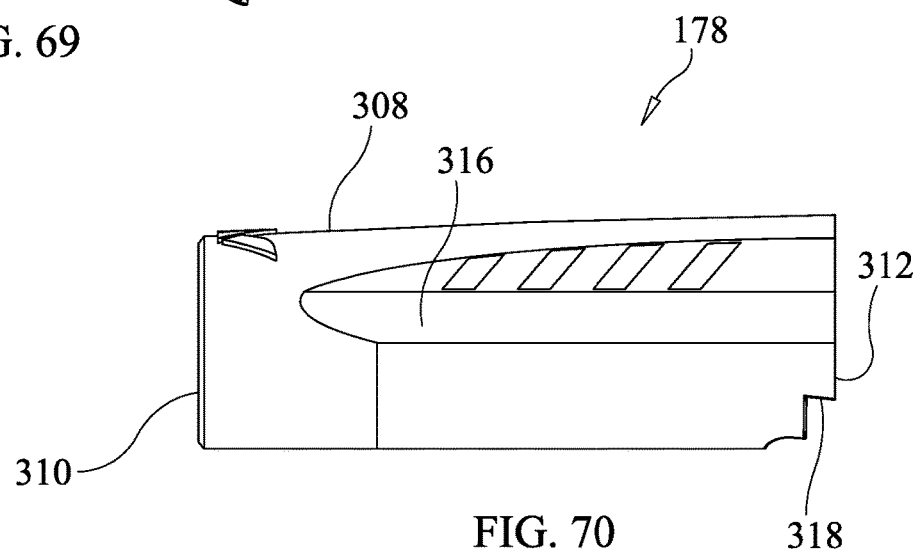
FIG. 70 is a side view of the sleeve of the present invention shown in FIG. 69.
Figure 71:
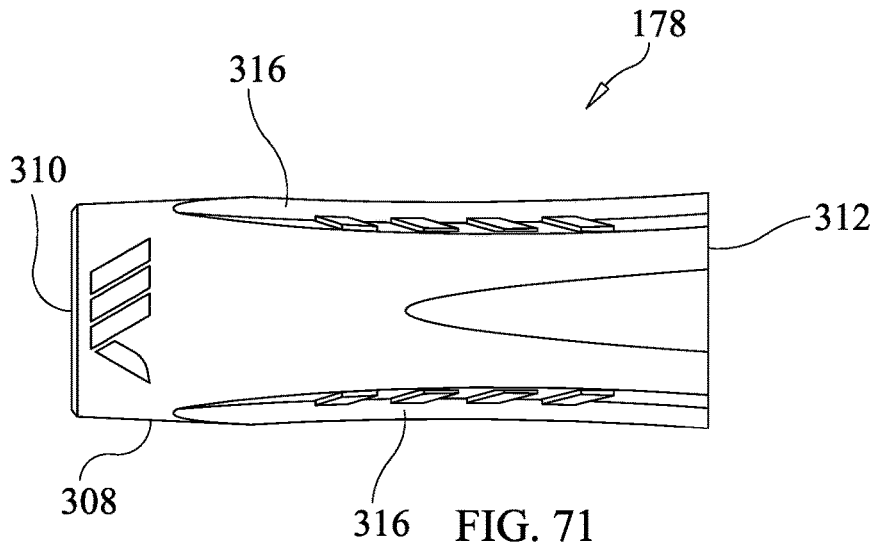
FIG. 71 is a top plan view of the sleeve of the present invention shown in FIGS. 69 and 70.
Figure 72:
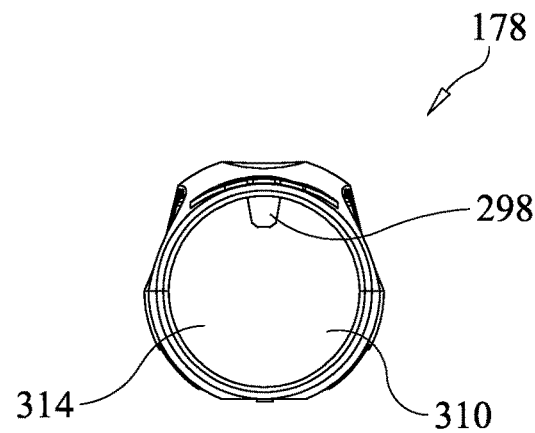
FIG. 72 is a front view of the sleeve of the present invention shown in FIGS. 69-71.
Figure 73:
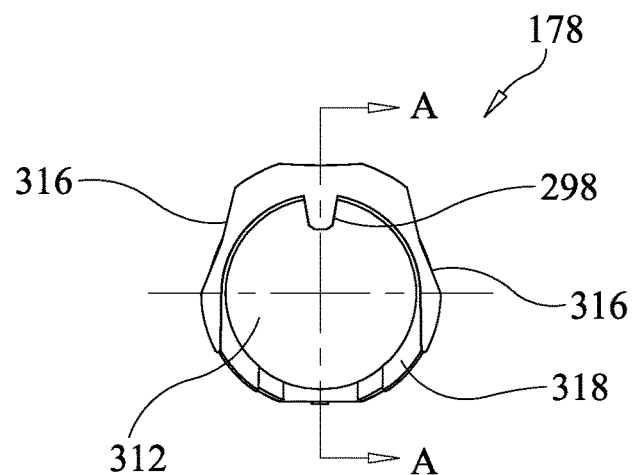
FIG. 73 is a rear view of the sleeve of the present invention shown in FIGS. 69-72.
Figure 74:
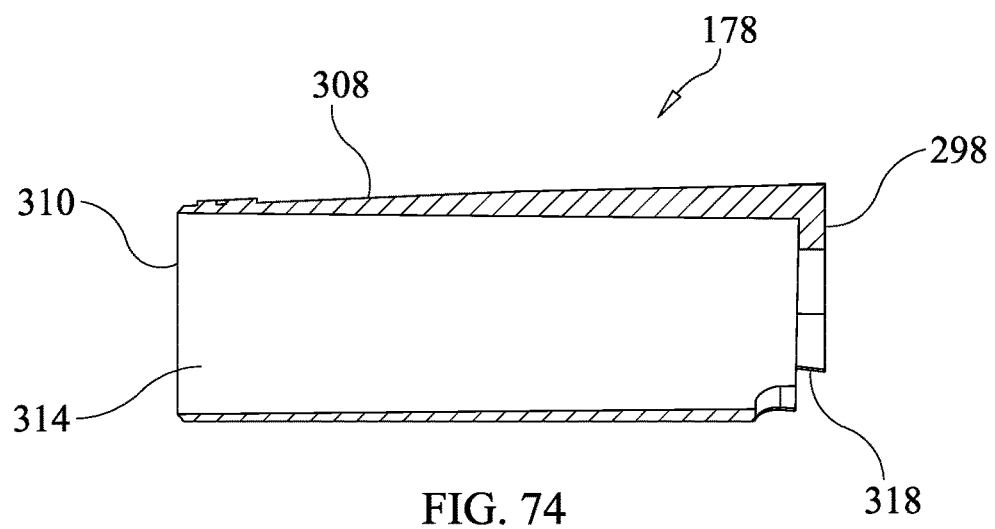
FIG. 74 is a cross-sectional view of the sleeve of the present invention shown in FIGS. 69-73, taken along line A-A of FIG. 73.

A hammer return spring 186 (see FIGS. 57-59), preferably in the form of a compression spring, is positioned in the enlarged internal bore 232 of the rear main body 206 of the front slide 172 and the axial bore 220 of the tubular front section 216 of the front slide 172. One axial end of the spring 186 is seated on and engages a radially extending wall 278 internal to the axial bore 220 of the tubular front section 216 of the front slide 172, and the other axial end of the spring 186 engages the front surface 236 of the strike plate 208 of the scope coupler 176. The spring 186 is axially in alignment with the bore 198 of the scope coupler 176 and the bore 220 of the tubular front section 216 of the front slide 172 so that, when an endoscope 14 is coupled to the surgical instrument 2, the distal end of the endoscope 14 will pass through the axial center of the hammer return spring 186 without interference from the spring 186.

The spring 186, preferably always compressed even slightly, exerts a force on the front surface 236 of the strike plate 208 of the scope coupler 176, when mounted on the front slide 172, to bias the scope coupler 176 axially rearwardly within the enlarged internal bore 232 of the rear main body 206 of the front slide 172. This will, in turn, cause the hammer 174 to remain pivoted in the blade retraced position, essentially upright on the front slide 172, as the lower, split end portion 212 of the hammer 174 engages the rear bearing surface 210 of the strike plate 208 of the scope coupler 176. Thus, when it is desired to extend the cutting blade 24 through the cannula slot 22 during a surgical procedure, the surgeon pulls back rearwardly on the double wing handle 248 of the hammer 174 to move the hammer 174 to the blade extended position, which causes the forked lower portion 212 of the hammer 174 to pivot and exert pressure on the rear bearing surface 210 of the strike plate 208 of the scope coupler 176 against the bias of the spring 186, driving the scope coupler 176 and an endoscope 14 coupled thereto axially forward partially through the enlarged internal bore 232 of the rear main body 206 of the front slide 172. The distal tip of the endoscope 14 will then engage the retractable cutting blade assembly 54 within the blade tube 48, which causes the cutting blade 24 to project outwardly from the cannula slot 22.

When the surgeon releases the double wing handle 248 of the hammer 174, the hammer 174 will return to the blade retracted position on the front slide 172 due to the force exerted by the compressed spring 186 on the front surface 236 of the strike plate 208 of the scope coupler 176, pushing the scope coupler 176, and the attached endoscope 14, axially rearwardly in the enlarged internal bore 232 of the rear main body 206 of the front slide 172. The hammer 174 will pivot on the front slide 172 to the blade retracted position, since the forked lower portion 212 of the hammer 174 is in contact and moves with the rear bearing surface 210 of the strike plate 208 of the scope coupler 176.

Figure 113:
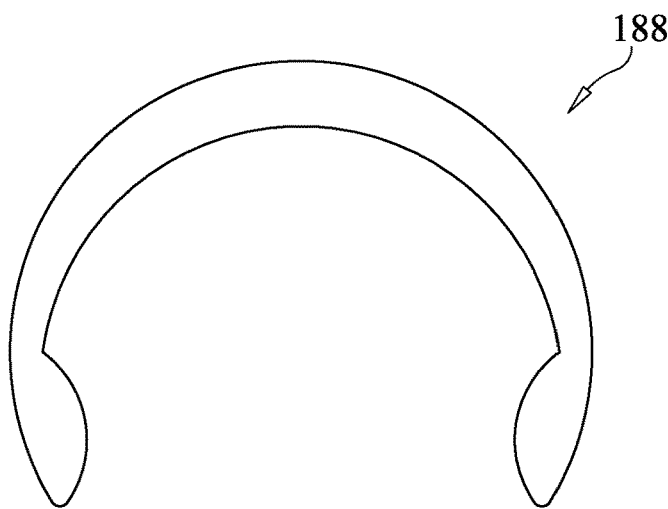
FIG. 113 is a front view of a retaining ring forming part of the second embodiment of the endoscopic surgical instrument of the present invention shown in FIGS. 29-31, and further forming part of the sleeve/cannula assembly.
Figure 114:
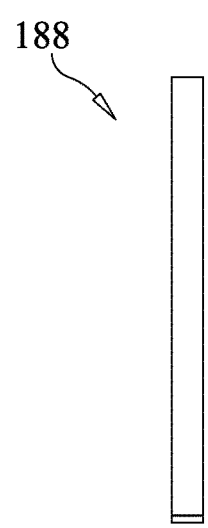
FIG. 114 is a side view of the retaining ring of the present invention shown in FIG. 113.

The cannula 6 of this version of the surgical instrument 2 is shown in FIGS. 60-68 of the drawings. The cannula 6 includes a generally cylindrical, barrel-like rear section 280 having an outer side wall 282 which is strengthened by a plurality of ribs 284 formed on the exterior surface thereof, the ribs 284 extending at least partially circumferentially about the exterior surface, adjacent ribs 284 being spaced apart from each other axially on the cylindrical rear section 280 of the cannula 6. The outer side wall 282 of the cylindrical rear section 280 of the cannula 6 defines an interior bore 286. As will be described in greater detail, the interior surface of the outer side wall 282 which faces the bore 286 has formed therein a groove 288 extending at least partially over the axial length of the cylindrical rear section 280, which groove 288 may slidably receive the guide rib 222 formed on the tubular front section 216 of the front slide 172. Thus, the rear axial wall 290 of the cylindrical rear section 280 is open to define a rear opening 296 for receiving in the interior bore 286 the elongated tubular front section 216 of the front slide 172. Furthermore, the exterior surface of the outer side wall 282 of the cylindrical rear section 280 of the cannula 6 has formed therein a partially circumferential groove 292 residing in proximity to the open rear end 290 of the cylindrical rear section 280, the groove 292 being provided for seating therein the retaining ring 188 (see FIGS. 113 and 114) that is used for assembling the cannula 6 and the sleeve 178 together, as will be described in greater detail. Additionally, an arcuate slot 294 is formed in the rear wall 290 of the cylindrical rear section 280 of the cannula 6 that surrounds the rear opening 296 of the cannula's rear section 280. This slot 294 receives a lock/unlock protrusion 298 of the sleeve 178, as will be described in greater detail.

The front wall 300 of the cylindrical rear section 280 of the cannula 6 is convexly conically shaped and has a central opening 302 formed through the thickness thereof. This conically-shaped front wall 300 is joined to an elongated, slotted, tubular member 16 of the cannula 6.

The tubular member 16 of the cannula 6 has formed axially therein an internal lumen 306 that extends from the conically-shaped front wall 300 of the cylindrical rear section 280 which attaches to the front slide 172. The tubular member 16 of the cannula 6 includes a flattened top wall 20, and a slot 22 formed through the thickness of the flattened top wall 20 and extending axially thereon over most or at least a portion of the longitudinal length thereof. The slot 22 is provided to allow the retractable cutting blade 24 to project outwardly therefrom, as will be explained in greater detail. Preferably, the cannula 6, or at least the tubular member 16 thereof, is transparent so that an endoscope or arthroscope 14 received by the surgical instrument 2 of the present invention and which passes through at least a portion of the lumen 306 of the cannula 6 can view through the clear, transparent tubular member 16 of the cannula 6 any tissue and other anatomical features at a surgical site when a surgeon is performing a procedure on a patient.

The tubular member 16 of the cannula 6 of this version of the surgical instrument 2 is similar in many respects to the cannula 6 of the surgical instrument 2 described previously and shown in FIGS. 1-28L of the drawings. However, in a preferred form of the present invention, the slot 22 formed in the flattened top wall 20 of the cannula 6 of this version of the surgical instrument 2 of the present invention and shown in FIGS. 60, 62 and 65-67 may be transversely wider than the slot 22 formed in the flattened top wall 20 of the cannula 6 of the surgical instrument 2 shown in FIGS. 1-28L. Even more preferably, the width of the cannula slot 22 is about 0.5 millimeters, and occupies an angle of about 180 degrees transversely across the tubular member 16 of the cannula 6.

The distal end 26 of the elongated tubular member 16 of the cannula 6 is preferably closed and blunt, with a curved end, to define an obturator thereat so that the cannula 6, when being positioned at a surgical site, will minimize any injury to the tissue that the cannula 6 comes in contact with. As will be described in greater detail, the retractable cutting blade 24 housed by the blade tube 48, as can be seen in FIGS. 90-93, is positioned at the distal end 26 of the elongated tubular member 16 of the cannula 6, but slightly axially inwardly of the obturator end thereof.

The sleeve 178 of the surgical instrument 2 is shown in FIGS. 69-74 of the drawings. The sleeve 178 is a generally cylindrical member formed with an outer side wall 308 which defines an open front axial end 310 and an opposite open rear axial end 312, and an internal bore 314 extending between and being in communication with the open front and rear axial ends 310, 312 of the sleeve 178. The cylindrical rear section 280 of the cannula 6 is received by the internal bore 314 of the sleeve 178 through the open front axial end 310 of the sleeve 178.

The generally cylindrically-shaped, outer side wall 308 of the sleeve 178 preferably includes flattened portions 316, preferably situated substantially diametrically opposite each other. These flattened portions 316 facilitate the grasping of the sleeve 178, and the at least partial rotation of the sleeve 178 on the cannula 6, by a surgeon using either his left or right hand.

The sleeve 178 further includes a relatively short lock/unlock protrusion 298, as mentioned previously, extending radially outwardly from the interior surface of the outer side wall 308 of the sleeve 178 and partially into the internal bore 314 of the sleeve 178. The lock/unlock protrusion 298 is situated in proximity to the open rear axial end 312 of the sleeve 178. When the cannula 6 and sleeve 178 are assembled together, this lock/unlock protrusion 298 will reside in the arcuate slot 294 formed in the rear wall 290 of the cylindrical rear section 280 of the cannula 6 at the rear axial opening 296 thereof, and is movable within the arcuate slot 294 to permit the sleeve 178 to be at least partially rotatable on the cylindrical rear section 280 of the cannula 6, the reason for which will become apparent from the following disclosure.

The cylindrical rear section 280 of the cannula 6 is received by the bore 314 of the sleeve 178, with the rear wall 290 of the cannula 6 that defines the rear axial opening 296 abutting against the lock/unlock protrusion 298 of the sleeve 178. The cylindrical rear section 280 of the cannula 6 is held in place within the sleeve 178 by the retaining ring 188 being received by and seated in the circumferential groove 292 formed in the outer side wall 282 of the cylindrical rear section 280 of the cannula 6 at the open rear wall 290 thereof. The retaining ring 188 is an open, partially circumferential and resilient flat member which may be forced into the groove 292 and which also engages an arcuate cut away portion 318 of the outer side wall 308 of the sleeve 178 at the open rear end 290 of the sleeve 178 to hold the cannula 6 and sleeve 178 together but to allow some rotational movement between the sleeve 178 and the cannula 6, which movement is limited by the arcuate extent of the slot 294 and the movement of the lock/unlock protrusion 298 of the sleeve 178 therewithin. The rotational movement of the sleeve 178 relative to the front slide 172 is preferably about 15 degrees to about 30 degrees. As will be described in greater detail, when the sleeve 178 is partially rotated on the front slide 172 in a first direction, for example, in a counterclockwise direction when viewing the sleeve 178 from the open rear wall 290 thereof, the sleeve lock/unlock protrusion 298 will move within the arcuate slot 294 of the cannula 6 to a "lock" position in which the sleeve/cannula assembly will remain axially fixed on the front slide 172 of the instrument 2. However, when the sleeve 178 is rotated on the front slide 172 in a second direction which is opposite to the first direction, for example, in a clockwise direction when viewing the sleeve 178 from the open rear wall 290 thereof, the sleeve lock/unlock protrusion 298 will move within the arcuate slot 294 of the cannula 6 to an "unlock" position in which the sleeve/cannula assembly is relatively axially movable on at least a portion of the tubular front section 216 of the front slide 172, thus allowing the front slide assembly, with the scope coupler 176 and blade tube 48 attached to the front slide 172, and an endoscope or arthroscope 14 coupled thereto, to be partially withdrawn axially from the sleeve/cannula assembly in a rearward direction, with or without the cutting blade 24 protruding outwardly from the cannula slot 22.

The tubular front section 216 of the front slide 172 is received by the interior bore 286 of the cylindrical rear section 280 of the cannula 6 through the rear opening 296 defined by the rear wall 290 thereof. More specifically, the guide rib 222 of the front slide 172 which extends axially along at least a portion of the axial length of the tubular front section 216 is slidably received by the axially extending groove 288 formed in the interior surface of the side wall 282 of the cylindrical rear section 280 of the cannula 6 such that, when the sleeve 178 is in the "unlock" position, the front slide assembly is axially movable relative to the sleeve/cannula assembly, with the guide rib 222 being axially slidable within the groove 288 of the cylindrical rear section 280 of the cannula 6. Preferably, the cannula 6 cannot rotate relative to the front slide 172, and only the sleeve 178 can partially rotate on the cannula 6 between the "lock" position and the "unlock" position when the tubular front section 216 of the front slide 172 is fully received by the interior bore 286 of the cylindrical rear section 280 of the cannula 6. When the sleeve 178 is in the 'unlock" position and the front slide 172 is in a retracted state (i.e., the tubular front section 216 of the front slide 172 is not fully received by the interior bore 186 of the cylindrical rear section 280 of the cannula 6) relative to the cannula 6 and sleeve 178, preferably neither the sleeve 178 nor the cannula 6 can rotate on the front slide 172.

When the sleeve 178 is in the "lock" position, the sleeve lock/unlock protrusion 298 is in alignment with the guide rib 222 on the front slide 172. There is a space 320 between the proximal end 322 of the guide rib 222 and the front wall 218 of the rear main body 206 of the front slide 172 from which the tubular front section 216 extends. This space 320 is dimensioned to receive therein the sleeve lock/unlock protrusion 298 when the sleeve 178 is in the "lock" position. The proximal end 322 of the guide rib 222 of the front slide 172 preferably engages the sleeve lock/unlock protrusion 298 when the sleeve 178 is in the "lock" position and the lock/unlock protrusion 298 is residing in the rib space 320 and is in alignment with the guide rib 222 to prevent axial movement between the front slide 172 and the cannula 6 and sleeve 178. However, when the sleeve 178 is rotated on the cylindrical rear section 280 of the cannula 6 to the "unlock" position, the sleeve lock/unlock protrusion 298 is no longer residing in the rib space 320 or in alignment with the guide rib 222. Such permits relative axial movement between the front slide 172 and the cannula 6 and sleeve 178.

Figure 75:
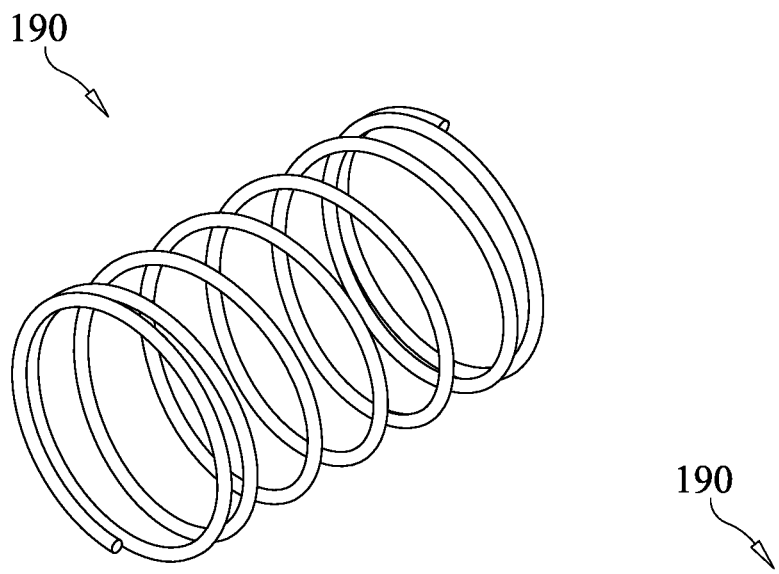
FIG. 75 is a perspective view of a cannula compression spring forming part of the second embodiment of the endoscopic surgical instrument of the present invention shown in FIGS. 29-31, and further forming part of the sleeve/cannula assembly.
Figure 76:
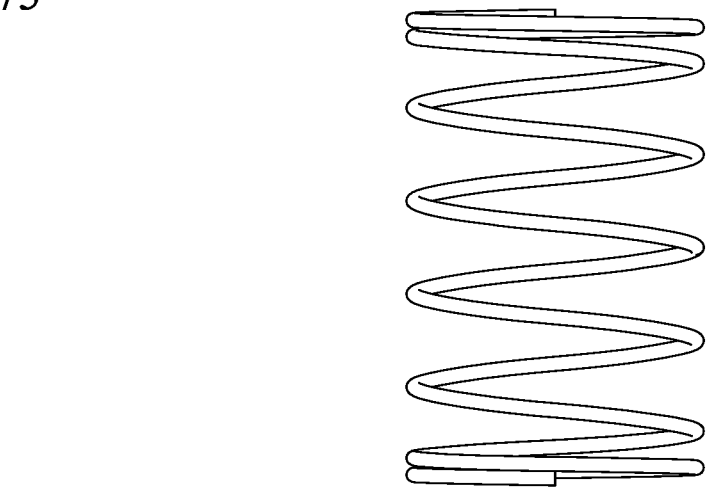
FIG. 76 is a side view of the cannula compression spring of the present invention shown in FIG. 75.
Figure 77:
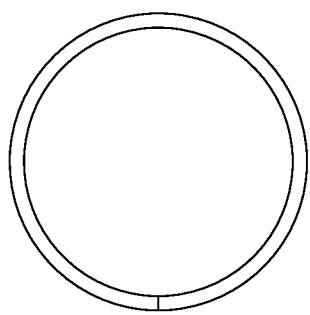
FIG. 77 is an end view of the cannula compression spring of the present invention shown in FIGS. 75 and 76.

To help prevent inadvertent relative axial movement between the sleeve/cannula assembly and the front slide assembly, a cannula compression spring 190 (see FIGS. 75-77) may be used. This spring 190 is positioned during assembly of the surgical instrument 2 between the inside surface of the conically shaped front wall 300 of the cylindrical rear section 280 of the cannula 6 and the distal end portion 324 of the tubular front section 216 of the front slide 172. The cannula spring 190 may function in several ways. In one embodiment of the surgical instrument 2, the spring 190, when expanded, biases the sleeve/cannula assembly in a rearward axial direction on the front slide assembly, that is, toward the front wall 218 of the rear main body 206 of the front slide 172. One axial end of the spring 190 may be affixed to the inside surface of the conically shaped front wall 300 of the cylindrical rear section 280 of the cannula 6, or to another surface of the cylindrical rear section 280, and the other axial end of the spring 190 may be affixed to the distal end portion 324 of the tubular front section 216 of the front slide 172, or to another surface on the front slide 172. A surgeon during a surgical procedure may rotate the sleeve 178 on the cannula 6 to the "unlock" position and, against the expanding bias of the spring 190, retract the front slide assembly rearwardly on the sleeve/cannula assembly. After this procedure is performed, and under the control of the surgeon, the expanded spring 190 will exert a force on the sleeve/cannula assembly and the front slide assembly to move these assemblies in a direction toward one another. In another embodiment, the cannula spring 190 is normally compressed between the conically shaped front wall 300 of the cylindrical rear section 280 of the cannula 6 and the distal end portion 324 of the tubular front section 216 of the front slide 172 when the sleeve/cannula assembly and the front slide assembly are assembled together. The spring 190 thus indirectly exerts a force on the sleeve lock/unlock protrusion 298 to keep it in frictional contact with the proximal end 322 of the guide rib 222 on the tubular front section 216 of the front slide 172 within the rib space 320, with the sleeve lock/unlock protrusion 298 being in alignment with the guide rib 222, to maintain the sleeve 178 in the "lock" position unless forcibly rotated by the surgeon to the "unlock" position.

Figure 78:
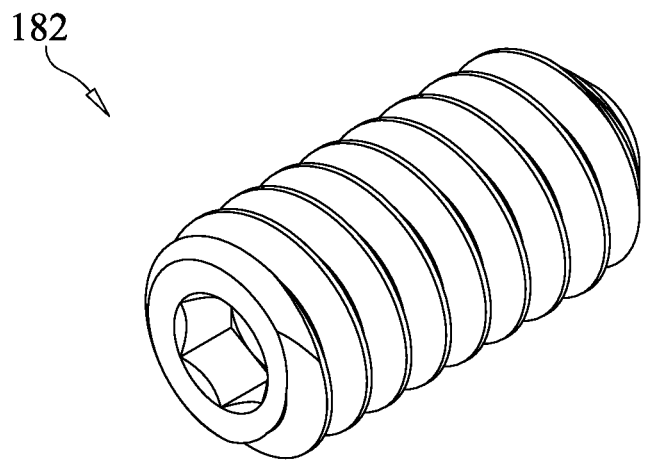
FIG. 78 is a perspective view of a set screw forming part of the second embodiment of the endoscopic surgical instrument of the present invention shown in FIGS. 29-31, and further forming part of the sleeve/cannula assembly.
Figure 79:
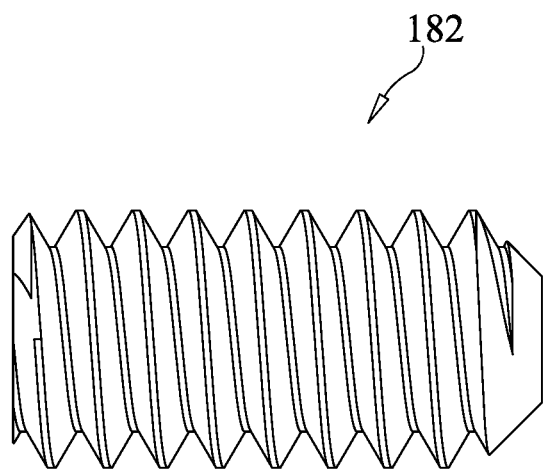
FIG. 79 is a side view of the set screw of the present invention shown in FIG. 78.
Figure 80:
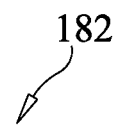
FIG. 80 is an end view of the set screw of the present invention shown in FIGS. 78 and 79.
Figure 81:
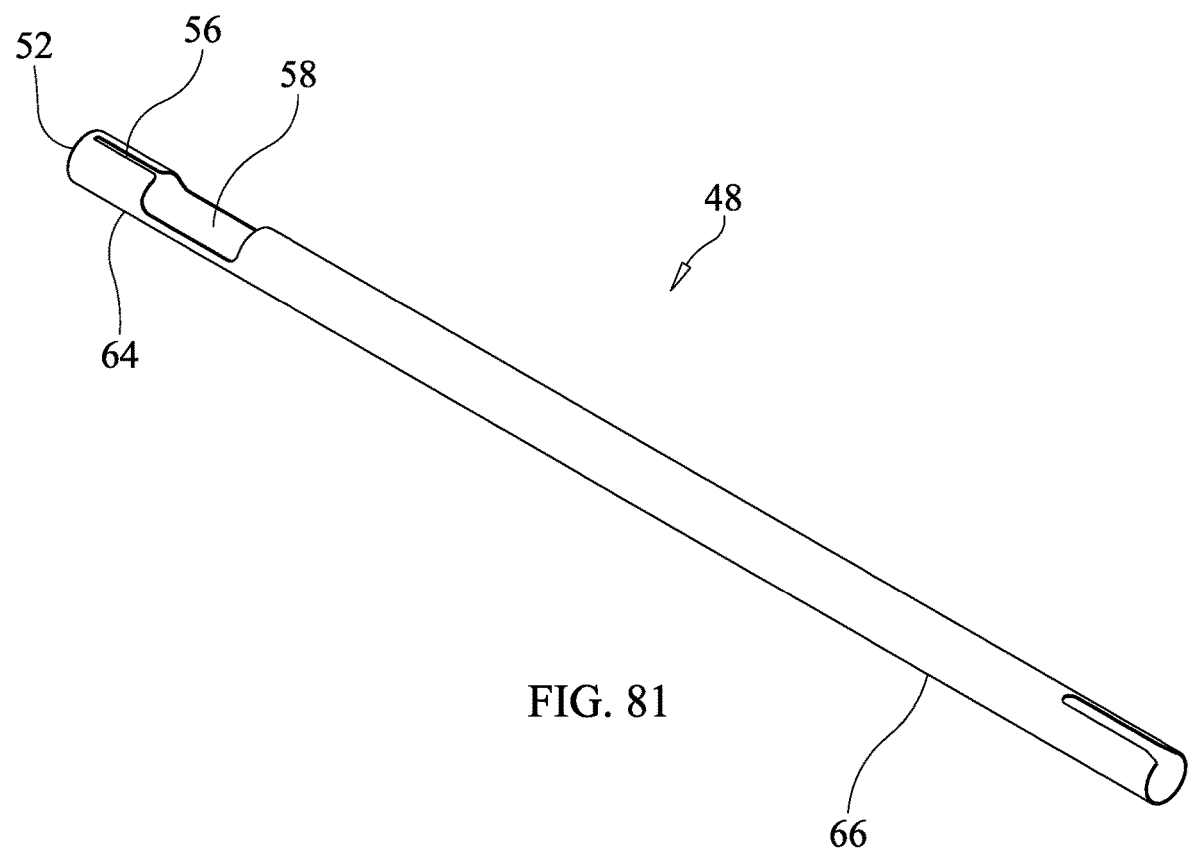
FIG. 81 is a perspective view of a blade tube forming part of the second embodiment of the endoscopic surgical instrument of the present invention shown in FIGS. 29-31, and further forming part of a blade tube assembly.
Figure 82:
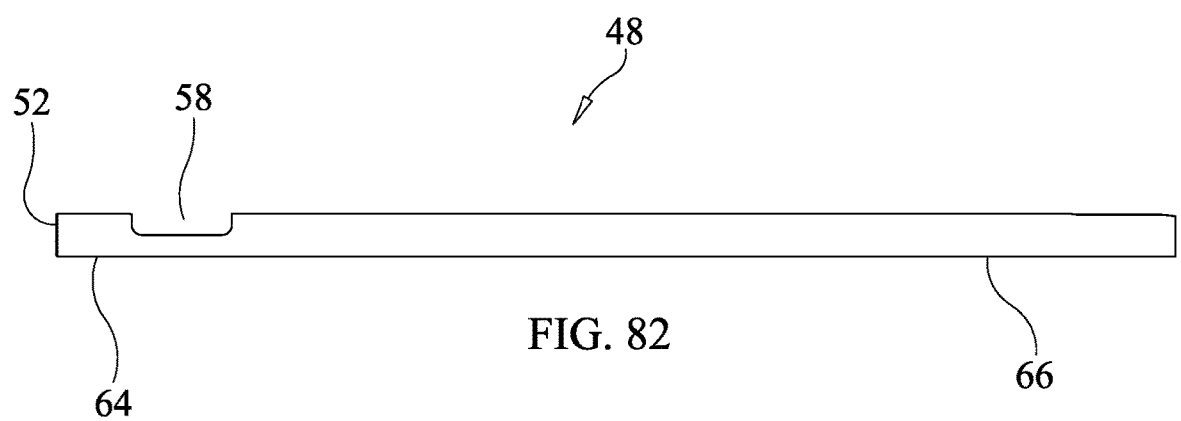
FIG. 82 is a side view of the blade tube of the present invention shown in FIG. 81.
Figure 83:
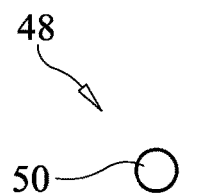
FIG. 83 is a rear view of the blade tube of the present invention shown in FIGS. 81 and 82.
Figure 84:
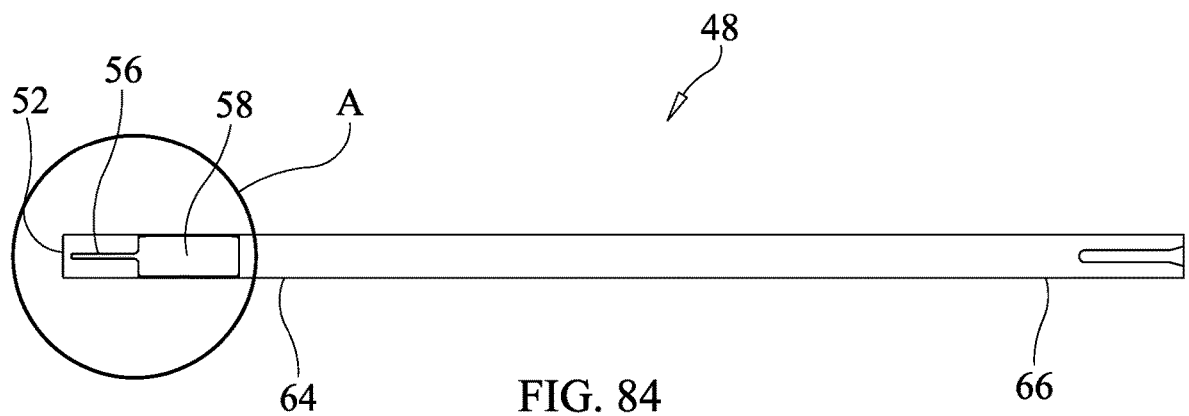
FIG. 84 is a top plan view of the blade tube of the present invention shown in FIGS. 81-83.
Figure 85:
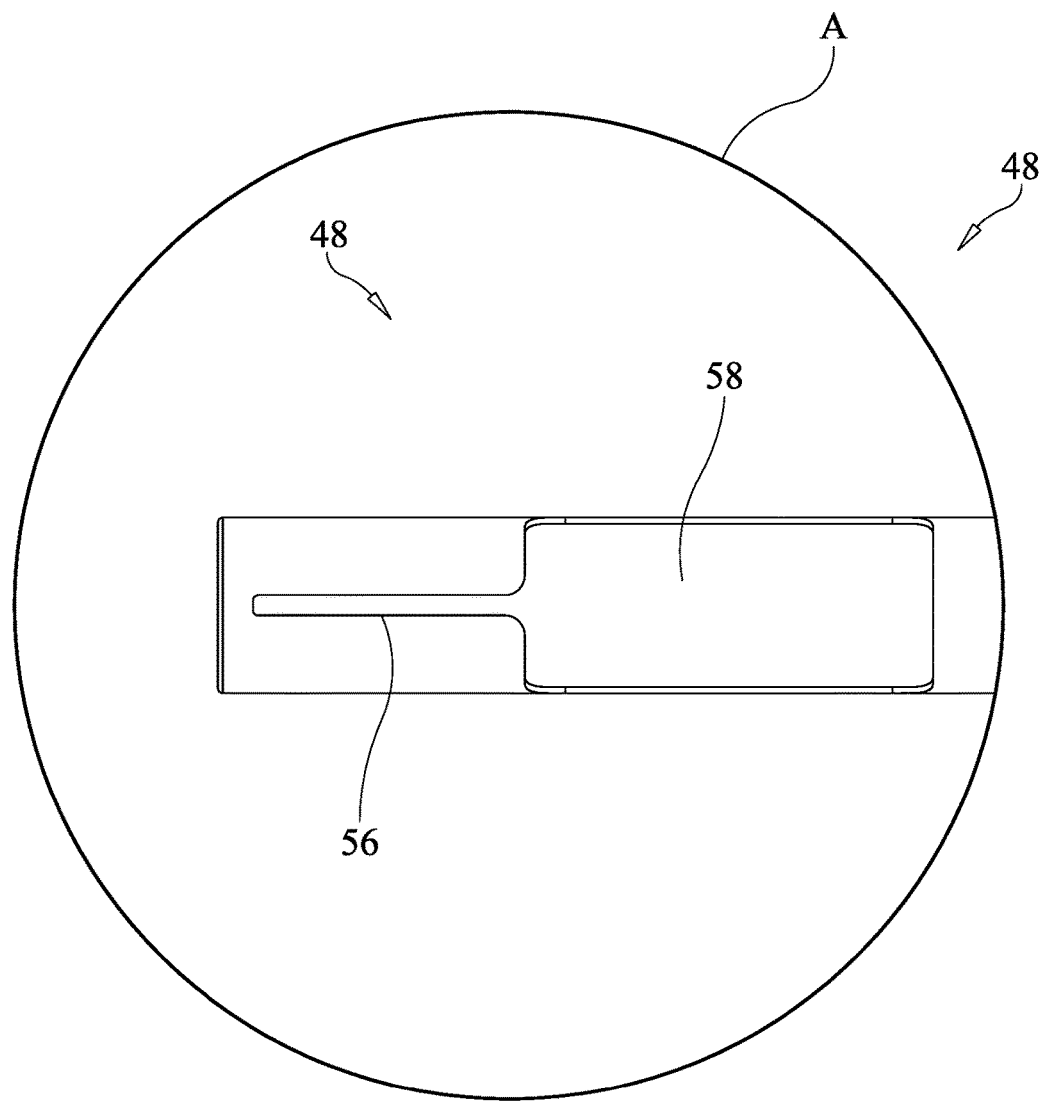
FIG. 85 is a detailed side view of a portion of the blade tube of the present invention shown in FIGS. 81-84, the portion being shown encircled by the circular line A of FIG. 84.
Figure 86:
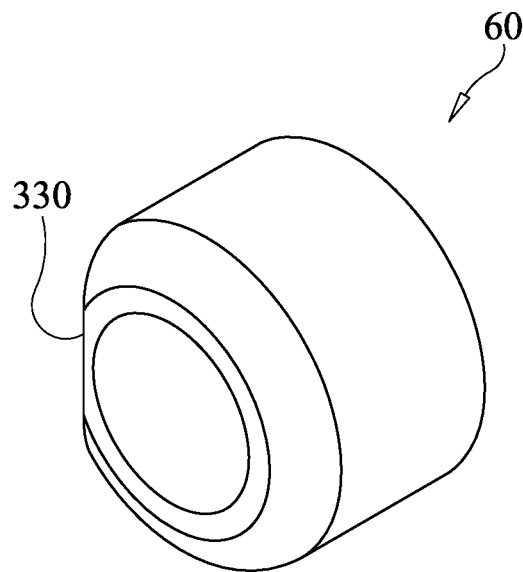
FIG. 86 is a perspective view of an alignment ring forming part of the second embodiment of the endoscopic surgical instrument of the present invention shown in FIGS. 29-31, and further forming part of the blade tube assembly.
Figure 87:
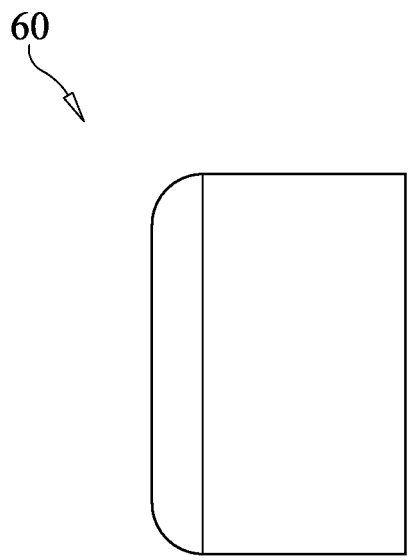
FIG. 87 is a side view of the alignment ring of the present invention shown in FIG. 86.
Figure 88:
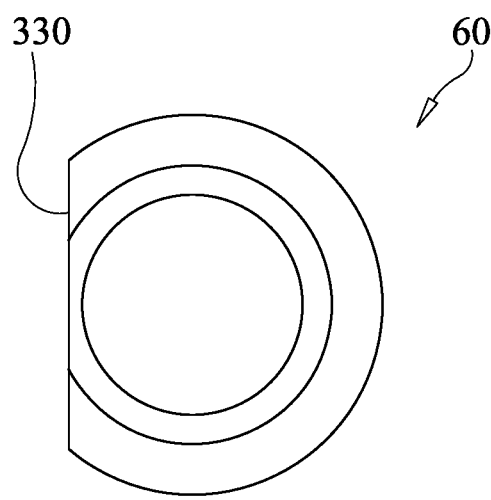
FIG. 88 is a rear view of the alignment ring of the present invention shown in FIGS. 86 and 87.
Figure 89:
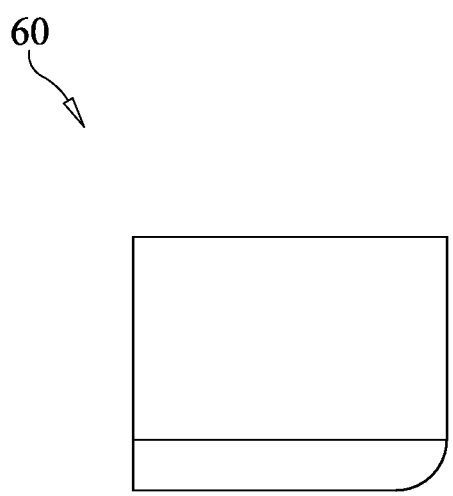
FIG. 89 is a top plan view of the alignment ring of the present invention shown in FIGS. 86-88.

The outer side wall 282 of the cylindrical rear section 280 of the cannula 6 also has a slot 326 (see FIG. 61), closed at opposite ends, formed through the thickness thereof. The slot 326 extends axially on the cylindrical rear section 280 at least partially along the length thereof. This slot 326 is dimensioned in its width to receive a stop member, such as the set screw 182 shown in FIGS. 78-80.

The tip of the set screw 182 is received in a threaded or unthreaded opening 328 formed in the tubular front section 216 of the front slide 172 near the distal end portion 324 thereof, the opening 328 being positioned to be in alignment with the slot 326. The set screw 182 is screwed into the opening 328 sufficiently such that the head of the screw 328 will not contact the inside surface of the outer side wall 308 of the sleeve 178 so as not to impede rotational movement of the sleeve 178 on the cylindrical rear section 280 of the cannula 6, but a portion of the set screw 182 will extend outwardly from the front slide 172 into the confines of the slot 326. The cooperation of the set screw 182 and the slot 326 causes the sleeve/cannula assembly to remain fixed to the front slide assembly, but will allow relative axial movement between the two assemblies when the sleeve 178 is in the "unlock" position on the cannula 6, the set screw 182 reciprocatingly sliding within the slot 326 from one closed end of the slot 326 to the opposite closed end of the slot 326 when the front slide assembly and the sleeve/cannula assembly move axially relative to one another. The set screw 182 or other form of stop member thus limits the extent to which these two assemblies may move relative to one another.

Figure 90:
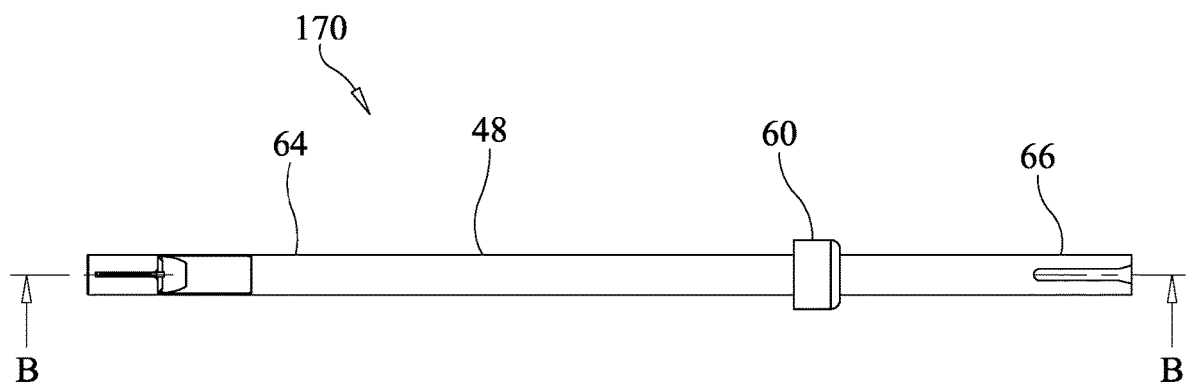
FIG. 90 is a top plan view of the blade tube assembly of the present invention comprising the blade tube shown in FIGS. 81-85 and the alignment ring shown in FIGS. 86-89 mounted thereon.
Figure 91:
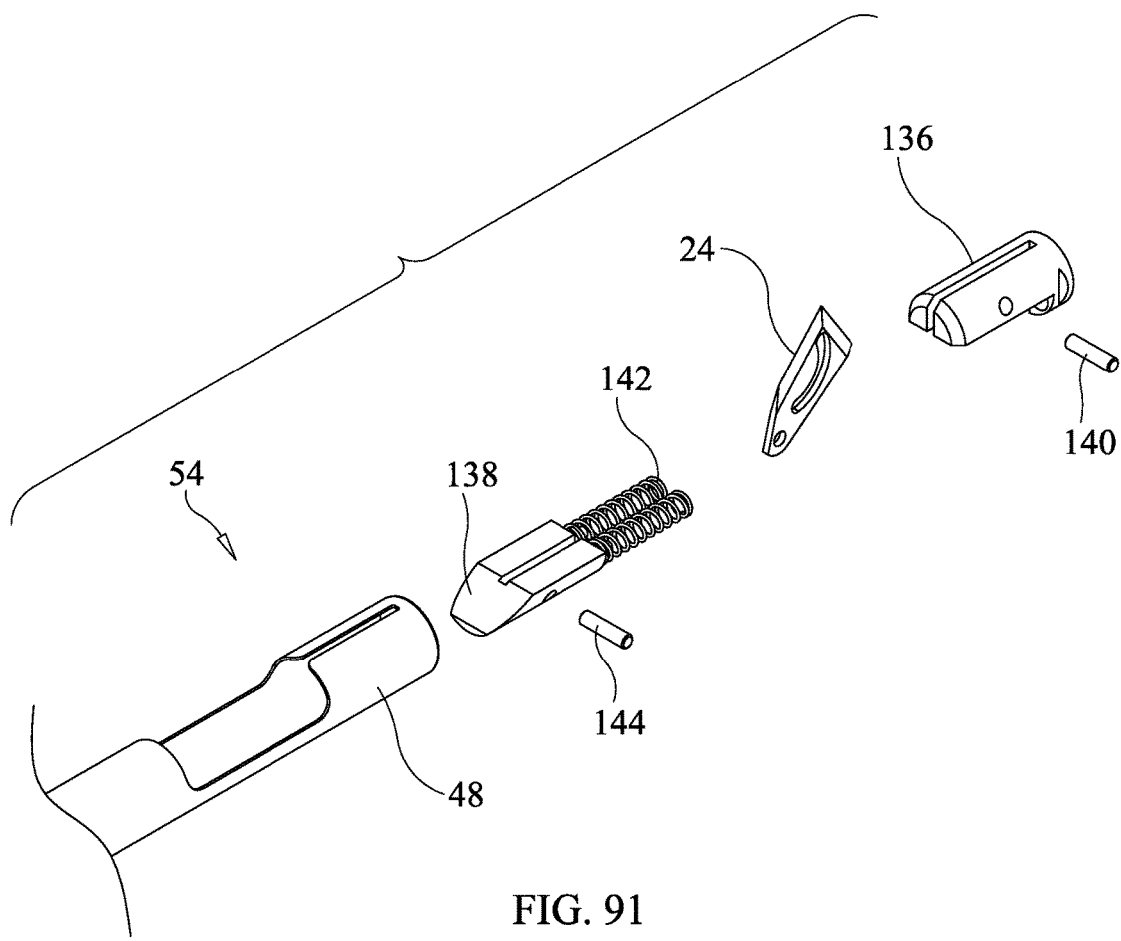
FIG. 91 is an exploded perspective view of a retractable cutting blade assembly forming part of the second embodiment of the endoscopic surgical instrument of the present invention shown in FIGS. 29-31, and further forming part of the blade tube assembly.
Figure 92:
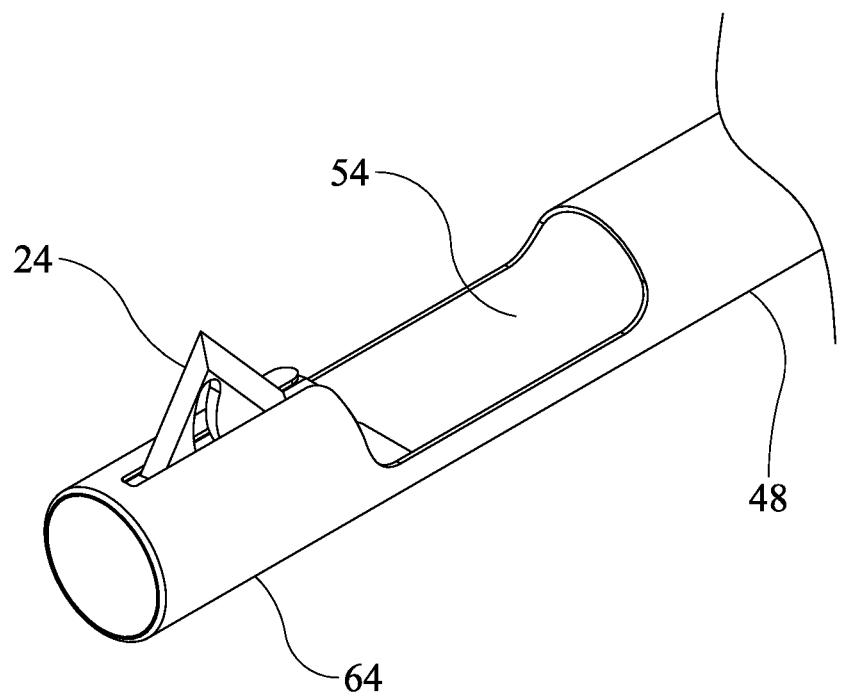
FIG. 92 is a perspective view of the distal end portion of the blade tube of the present invention shown in FIGS. 81-85 and a retractable cutting blade forming part of the retractable cutting blade assembly of the present invention shown in FIG. 91.
Figure 93:
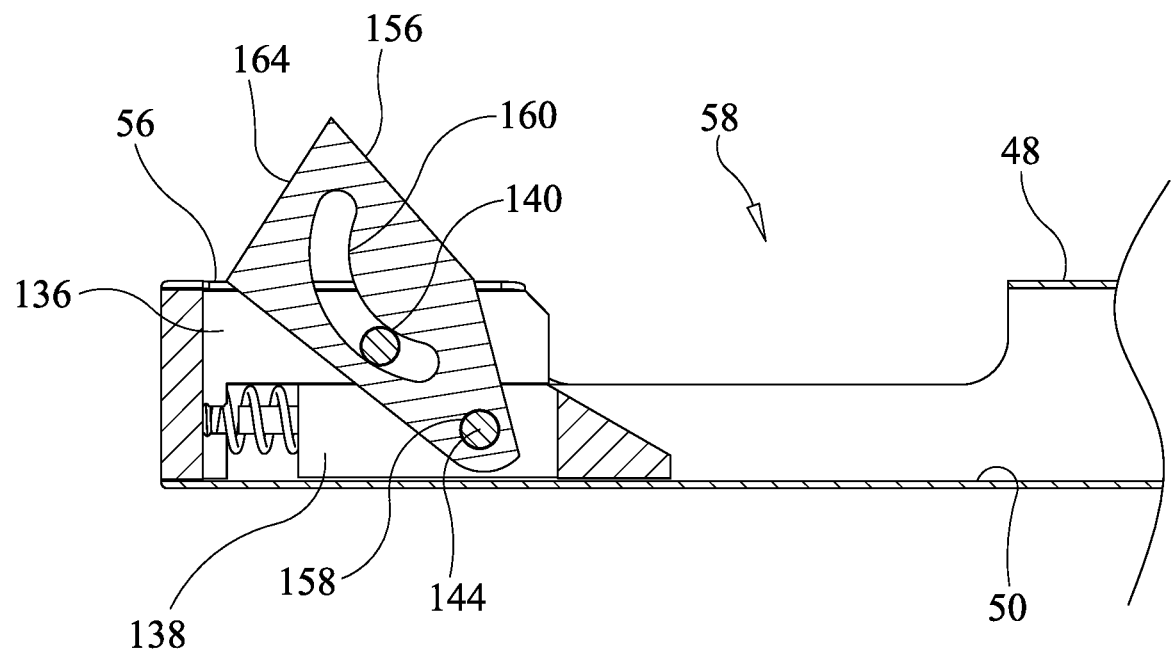
FIG. 93 is a cross-sectional view of the distal end portion of the blade tube assembly and retractable cutting blade assembly of the present invention, taken along line B-B of FIG. 90.
Figure 94:
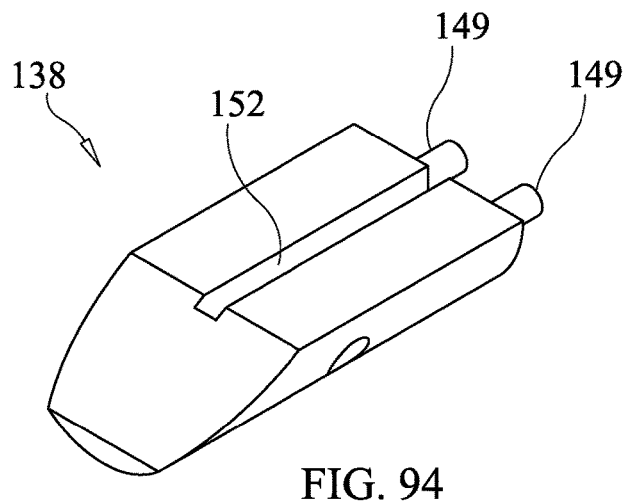
FIG. 94 is a perspective view of a bottom blade housing forming part of the second embodiment of the endoscopic surgical instrument of the present invention shown in FIGS. 29-31, and further forming part of the retractable cutting blade assembly.
Figure 95:
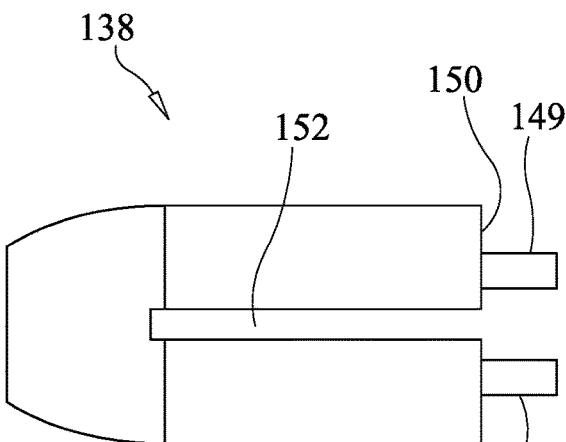
FIG. 95 is a top plan view of the bottom blade housing of the present invention shown in FIG. 94.
Figure 96:
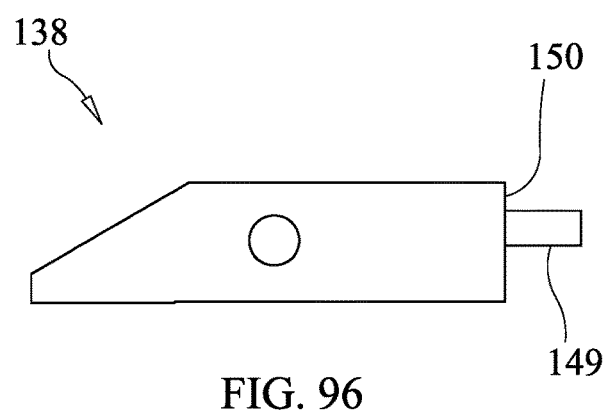
FIG. 96 is a side view of the bottom blade housing of the present invention shown in FIGS. 94 and 95.
Figure 97:
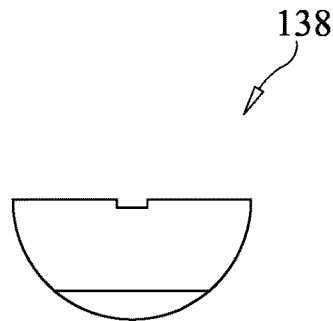
FIG. 97 is a rear view of the bottom blade housing of the present invention shown in FIGS. 94-96.
Figure 98:
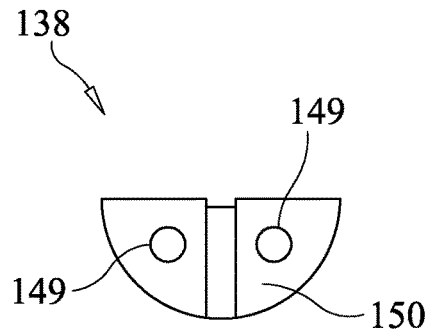
FIG. 98 is a front view of the bottom blade housing of the present invention shown in FIGS. 94-97.
Figure 99:
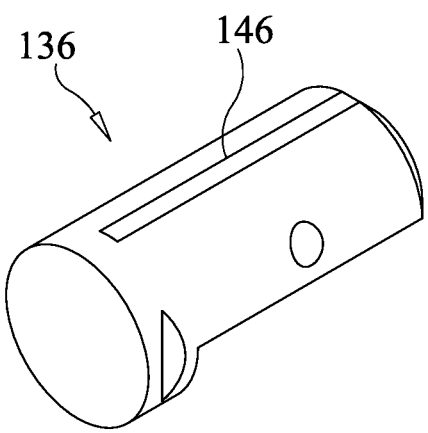
FIG. 99 is a perspective view of a top blade housing forming part of the second embodiment of the endoscopic surgical instrument of the present invention shown in FIGS. 29-31, and further forming part of the retractable cutting blade assembly.
Figure 100:
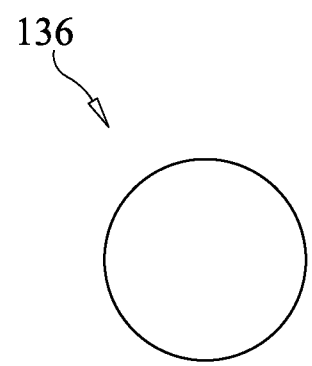
FIG. 100 is a front view of the top blade housing of the present invention shown in FIG. 99.
Figure 101:
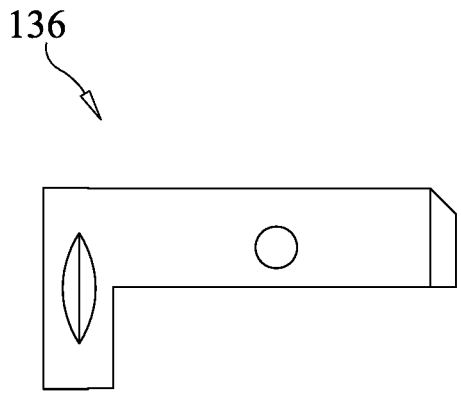
FIG. 101 is a side view of the top blade housing of the present invention shown in FIGS. 99 and 100.
Figure 102:
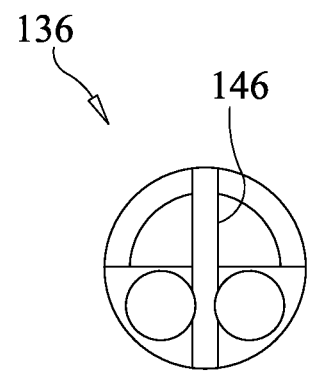
FIG. 102 is a rear view of the top blade housing of the present invention shown in FIGS. 99-101.
Figure 103:
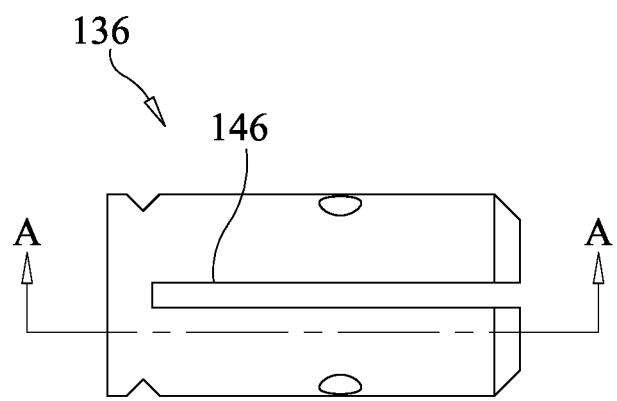
FIG. 103 is a top plan view of the top blade housing of the present invention shown in FIGS. 99-102.
Figure 104:
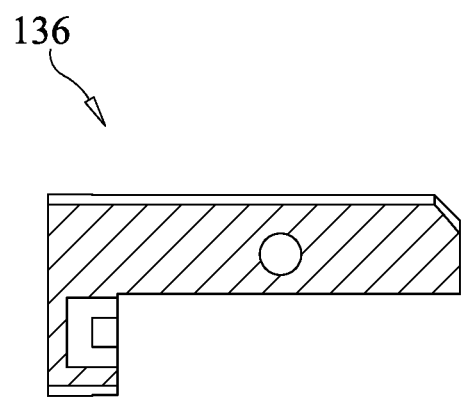
FIG. 104 is a cross-sectional view of the top blade housing of the present invention shown in FIGS. 99-103, taken along line A-A of FIG. 103.
Figure 105:
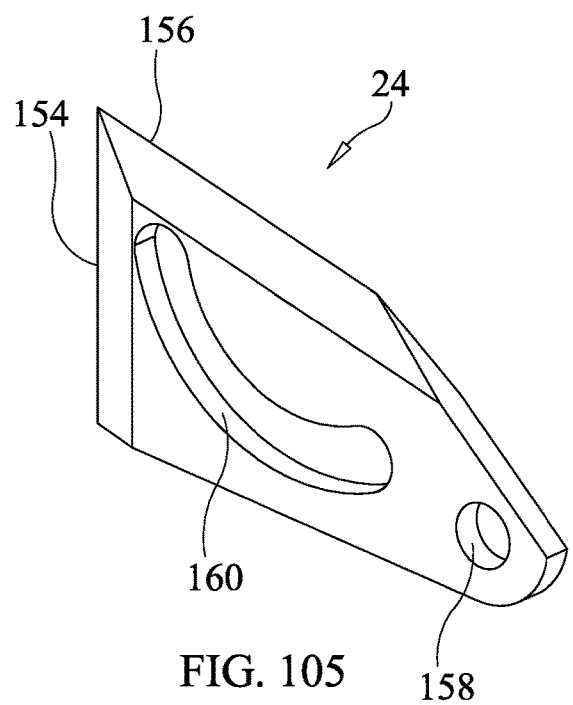
FIG. 105 is a perspective view of a cutting blade forming part of the second embodiment of the endoscopic surgical instrument of the present invention shown in FIGS. 29-31, and further forming part of the retractable cutting blade assembly.
Figure 106:
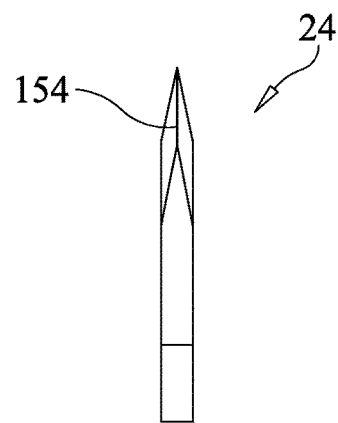
FIG. 106 is a bottom plan view of the cutting blade of the present invention shown in FIG. 105.
Figure 107:
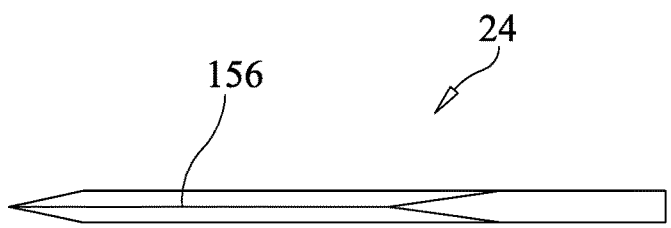
FIG. 107 is a top plan view of the cutting blade of the present invention shown in FIGS. 105 and 106.
Figure 108:
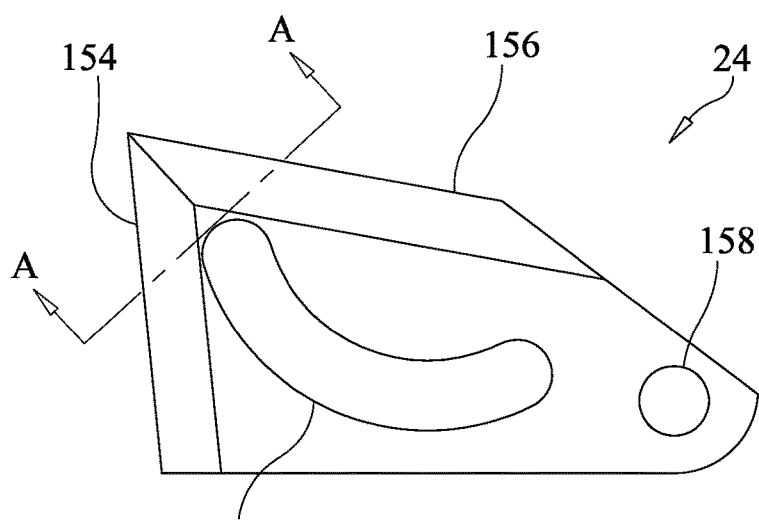
FIG. 108 is a side view of the cutting blade of the present invention shown in FIGS. 105-107.
Figure 109:
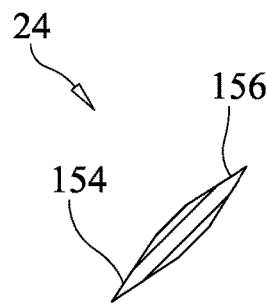
FIG. 109 is a cross-sectional view of the cutting blade of the present invention shown in FIGS. 105-108, taken along line A-A of FIG. 108.
Figure 110:
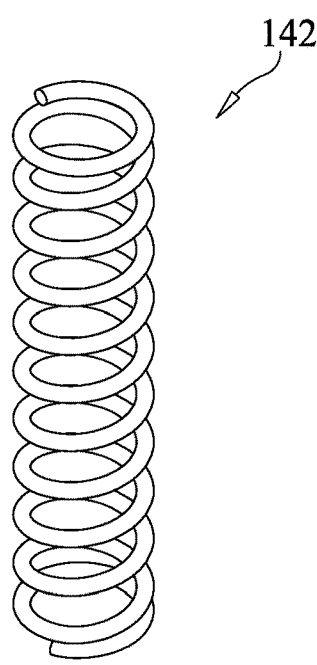
FIG. 110 is a perspective view of a compression spring forming part of the second embodiment of the endoscopic surgical instrument of the present invention shown in FIGS. 29-31, and further forming part of the retractable cutting blade assembly.

This second embodiment of the surgical instrument 2 of the present invention also includes a blade tube assembly 170, as shown in FIG. 90, which is structured similarly to, and includes most if not all of the components of, the inner tube 48 and the retractable cutting blade assembly 54 of the first embodiment of the surgical instrument 2 described previously and shown in FIGS. 1-28L of the drawings.

More specifically, the blade tube assembly 170 includes the blade tube 48 (see FIGS. 81-85), an alignment ring 60 (see FIGS. 86-89) fixedly mounted on the outer surface of the side wall of the blade tube 48 at a predetermined position on the axial length of the blade tube 48, and a retractable cutting blade assembly 54 (see FIGS. 90-93) located in proximity to the distal end 52 of the blade tube 48 and within the bore 50 thereof.

Even more specifically, the blade tube 48 defines a bore 50 that extends axially therethrough, and has a closed distal end 52 (the distal end 52 of the blade tube 48 may be closed by a top blade housing 136 forming part of the retractable cutting blade assembly 54). As will be explained in greater detail, the blade tube 48 is receivable by the tubular member 16 of the cannula 6 in the lumen 306 thereof.

In proximity to the distal end 52 of the blade tube 48, within the bore 50 thereof, is located the retractable cutting blade assembly 54. The cutting blade 24 selectively projects from and retracts into the bore 50 through a narrow slot 56 formed in the side wall of the blade tube 48. Slightly axially inwardly from the distal end 52 of the blade tube 48 is a window 58 defined by a cutaway portion of the side wall over about a 180°, or slightly greater, portion of the side wall. This window 58 is provided so that the distal end of an endoscope or arthroscope 14, which is angled at about 30°, may view through this window 58 and through the clear, transparent cannula 6 any tissue or anatomical structure of a patient at a surgical site during a surgical procedure. As will be explained in greater detail, the distal tubular portion of the endoscope 14 is received by the bore 50 of the blade tube 48 so that the viewing end thereof is positioned in proximity to the window 58 formed in the side wall of the blade tube 48.

Near the proximal end 66 of the blade tube 48, or spaced partially axially inwardly thereof, is fixedly mounted an alignment ring 60 extending radially outwardly from the outer surface of the side wall of the blade tube 48. A portion of the alignment ring 60 is cut away to form a flattened chordal surface 330. This alignment ring 60 and the proximal portion 66 of the blade tube 48 extending beyond the alignment ring 60 are received by the bore 220 of the tubular front section 216 of the front slide 172. The distal end portion 324 of the tubular front section 216 is shaped to form a recessed opening 332 with a surrounding lip 334, the recessed opening 332 being in communication with the bore 220 of the tubular front section 216 of the front slide 172 and further being formed with a complementary shape to that of the alignment ring 60, that is, the rounded inner surface of the side wall that defines the lip 334 of the tubular front section 216 of the front slide 172 includes a flattened portion 336 situated on a substantially diametrically opposite side of the tubular front section 216 from where the guide rib 222 is located. This flattened portion 336 of the inner surface of the side wall mates with the flattened chordal surface 330 of the alignment ring 60 when the ring 60 and proximal end 66 of the blade tube 48 are received by the bore 220 of the tubular front section 216 of the front slide 172 so that the blade tube 48 is properly positioned on the front slide 172, with the blade slot 56 formed in the tube 48 being in alignment with the slot 22 formed in the tubular member 16 of the cannula 6. Furthermore, the alignment ring 60 is fixedly positioned on the blade tube 48 at a predetermined location on the axial length thereof so that the distal end portion 64 of the blade tube 48 projects axially from the distal end portion 324 of the tubular front section 216 of the front slide 172 a predetermined distance so as to be received by and extend through most of the full axial length of the cannula lumen 306. A proximal end portion 66 of the blade tube 48 that extends axially beyond the alignment ring 60 passes through at least a portion of the bore 220 formed axially through the tubular front section 216 of the front slide 172.

The retractable cutting blade assembly 54 will now be described, and reference should be had to FIGS. 90-110 of the drawings. The retractable cutting blade assembly 54 is positioned at the distal end portion 64 of the blade tube 48 and preferably forms a closure at the open end of the tube 48. The retractable cutting blade assembly 54 includes a top blade housing 136, a bottom blade housing 138, an actuator pin 140, a retractable cutting blade 24, at least one compression spring 142 and a pivot pin 144.

More specifically, and as shown in FIGS. 99-104 of the drawings, the top blade housing 136 is situated at the distal end portion 52 of the blade tube 48, as mentioned previously, and closes the end of the tube 48. Thus, the top blade housing 136 is fixedly mounted in the blade tube 48. The top blade housing 136 includes a slot 146 formed through the thickness thereof through which the cutting blade 24 may extend from and retract into. This slot 146 in the top blade housing 136 is positioned to be in alignment with a similar slot 56 formed through the thickness of the outer wall of the blade tube 48 so that the cutting blade 24 may project from and retract into both slots 146, 56.

Figure 111:
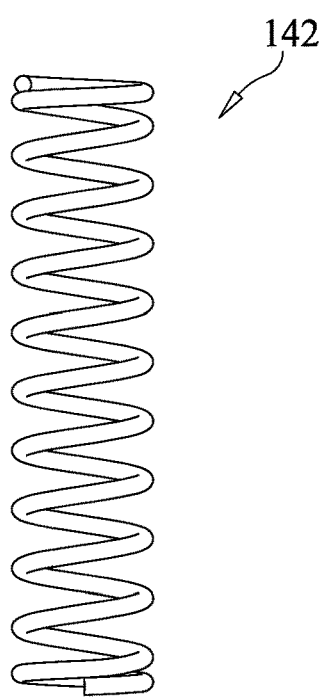
FIG. 111 is a side view of the compression spring of the present invention shown in FIG. 110.
Figure 112:
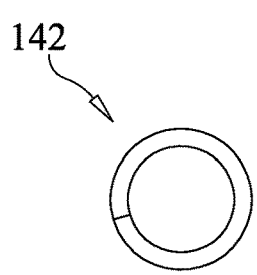
FIG. 112 is an end view of the compression spring of the present invention shown in FIGS. 110 and 111.

The bottom blade housing 138 (see FIGS. 94-98) slides reciprocatingly in the bore 50 of the blade tube 48 and at least partially under the top blade housing 136. The bottom blade housing 138 is slidably joined to the top blade housing 136 by one or two compression springs 142 (see FIGS. 110-112), one axial end of each of which is connected to a shoulder 148 of the top blade housing 136, and the opposite axial end of each of which is mounted on a respective retaining post 149 extending outwardly from an end wall 150 of the bottom blade housing 138 that faces the shoulder 148 of the top blade housing 136. The bottom blade housing 138 also includes a slot 152 formed in an upper surface thereof, which slot 152 is positioned to be in alignment with the slot 146 of the top blade housing 136. The slot 152 in the bottom blade housing 138 also at least partially receives a portion of the cutting blade 24, as will be described below.

There is a pivot pin 144 that passes transversely through the body of the bottom blade housing 138. This pivot pin 144 holds one end of the cutting blade 24 in place in the slot 152 of the bottom blade housing 138, and allows the cutting blade 24 to pivot thereon and within the slot 152. Similarly, there is an actuator pin 140 which passes transversely through the top blade housing 136 and through the slot 146 formed therein.

The retractable cutting blade 24 (see FIGS. 105-109) includes a forward facing sharpened edge 154 and a rearward facing sharpened edge 156. The blade 24 also includes an opening 158 formed transversely therethrough located generally opposite the cutting edges 154, 156 and at a lower portion of the blade 24. This opening 158 receives the pivot pin 144 of the bottom blade housing 138, and the pivot pin 144 secures the blade 24 to the bottom blade housing 138 but allowing it to pivot thereon.

The retractable cutting blade 24 further includes an arcuate slot 160 formed through the thickness thereof and at an upper portion thereof, nearer the sharpened edges 154, 156 than where the pivot pin opening 158 is located. This arcuate slot 160 is provided for receiving the actuator pin 140 that passes through the top blade housing 136. The actuator pin 140, when received by this arcuate slot 160 formed in the cutting blade 24, causes the cutting blade 24 to move within the slot 146 of the top blade housing 136 between an extended position (when the actuator pin 140 is at or near the bottom end of the arcuate slot 160) and a retracted position (when the actuator pin 140 is located at or near the upper end of the arcuate slot 160).

The compression spring 142 biases the bottom blade housing 138 away from the top blade housing 136. When pressure is exerted on the bottom blade housing 138 by the tip of an endoscope or arthroscope 14 to compress the spring 142, the bottom blade housing 138 moves forward, towards the top blade housing 136. As a result, the cutting blade 24 pivots on the pivot pin 144 of the bottom blade housing 138 and is guided in its movement by the actuator pin 140 situated within the arcuate slot 160 formed therein. Since the top blade housing 136 is fixed within the blade tube 48, movement of the bottom blade housing 138 towards the top blade housing 136 causes the cutting blade 24 to move from a retracted state, with the actuator pin 140 being situated at or near the upper end of the arcuate slot 160 formed in the blade 24, to an extended state, with the actuator pin 140 being located at or near the lower end of the arcuate slot 160 formed through the blade 24, such that the blade 24 extends outwardly of the slot 146 formed in the top blade housing 136 as well as the aligned slot 56 formed in the blade tube 48.

When the tip of the endoscope or arthroscope 14 is withdrawn in the blade tube 48, the compression spring 142 relaxes and causes the bottom blade housing 138 to move away from the top blade housing 136, resulting in the cutting blade 24 being retracted within the slot 146 formed in the top blade housing 136 and the slot 56 formed in the blade tube 48, due to the blade 24 pivoting on the pivot pin 144 and being affixed to the slidable bottom blade housing 138, and with the actuator pin 140 now occupying the top end of the arcuate slot 160 formed in the cutting blade 24. Accordingly, the retraction and extension of the cutting blade 24 through the slot 56 in the blade tube 48 and the slot 22 of the tubular member 16 of the cannula 6 may be easily controlled by the surgeon at any time during a surgical procedure by how far the tip of the endoscope 14 extends into the blade tube 48 of the surgical instrument 2.

More specifically, the surgeon may easily control the extent to which the distal end or tip of the endoscope or arthroscope 14 extends into the blade tube 48 of the surgical instrument 2 by adjusting the position of the hammer 174 on the front slide 172. Even more specifically, when the hammer 174 of the surgical instrument 2 is in an upright position on the front slide 172, it exerts little or no forward force on the scope coupler 176. An endoscope or arthroscope 14 received by the surgical instrument 2 and properly affixed to the scope coupler 176 of the instrument 2 will not extend into the blade tube 48 so far as to actuate the retractable blade assembly 54 and, accordingly, the cutting blade 24 will remain in a retracted position within the blade tube 48. However, by pivoting the hammer 174 on the front slide 172 about 90 degrees against the bias of the hammer return spring 186 from its upright position on the front slide 172 such that the hammer 174 is in a reclining, lowered position on the front slide 172, the hammer 174 will exert a forward force on the scope coupler 176 and the endoscope or arthroscope 14 attached to the scope coupler 176. The tip or distal end of the endoscope or arthroscope 14 will now sufficiently engage the retractable cutting blade assembly 54 and, in particular, cause the bottom blade housing 138 to slide against the bias of the compression spring 142 towards the top blade housing 136, causing the cutting blade 24 to extend upwardly through the slot 56 of the blade tube 48 and the slot 22 of the outer cannula 6 to effect the cutting of tissue during a surgical procedure.

In preparing this second embodiment of the instrument 2 of the present invention for a surgical procedure, such as the procedure described earlier that is performed on a patient afflicted with carpal tunnel syndrome, the distal end of an endoscope 14 is inserted into the rear axial opening 200 of the scope coupler 176 forming part of the front slide assembly until portions of the ball bearings 114 are seated in the groove 118 of the endoscope's body and the endoscope 14 is secured to, but removable by force from, the scope coupler 176 and generally the surgical instrument 2. Once the endoscope 14 is properly attached to the surgical instrument 2, the distal end of the endoscope 14 will be positioned within the blade tube 48 to be in close proximity to the retractable cutting blade assembly 54 without moving the bottom blade housing 138 forward so that the blade 24 remains in a retracted state within the blade tube 48. During this time, the sleeve 178 is in the "lock" position so that the sleeve/cannula assembly remains axially stationary on the front slide assembly. As a precaution, the safety piece 180 should remain in place on the front slide assembly to prevent the hammer 174 from inadvertently being pivoted downwardly on the front slide 172, which would otherwise have caused the endoscope 14 to engage the retractable cutting blade assembly 54 and cause the blade 24 to project through the cannula slot 22.

An incision is made just proximal or distal to the transverse carpal ligament, making an entry portal. The distal end portion 26 of the cannula 6, attached to the surgical instrument 2 and the endoscope or arthroscope 14, is inserted into the entry portal, and the front obturator end of the cannula 6 is introduced into the incision and used to create a passage under the carpal transverse ligament, but superficial to the median nerve, with the slot 22 of the cannula 6 facing the transverse carpal ligament. The procedure is observed with the optical system of the endoscope 14. By rotating the sleeve 178 to the "unlock" position, the front slide assembly, with the endoscope 14 and the blade tube assembly 170 attached thereto, may be axially rearwardly withdrawn from the sleeve/cannula assembly such that the optical system at the distal end of the endoscope 14 may be moved axially within the transparent tubular member 16 of the cannula 6 to observe and image the target tissue and surrounding tissues. The distal end of the endoscope or arthroscope 14, received by the blade tube 48 of the surgical instrument 2, may view such tissue through the window 58 formed in the blade tube 48, without actuating the retractable cutting blade assembly 54 so that the cutting blade 24 remains retracted within the blade tube 48 of the surgical instrument 2.

The instrument 2, during this procedure of observation of the tissue at the surgical site, is in the "lock" mode to prevent the distal end or tip of the endoscope 14 from inadvertently actuating the retractable cutting blade assembly 54. It should be noted that the slot 22 of the transparent tubular member 16 of the cannula 6, formed on the flat top wall 20 thereof, may remain positioned in alignment to face the transverse carpal ligament and will be in proper position when the blade 24 is extended from the cannula slot 22.

After the visualization step has been performed, as described above, the tubular front section 216 of the front slide assembly, which includes the scope coupler assembly having the endoscope 14 attached thereto, is moved forward axially on the sleeve/cannula assembly. The cooperation of the guide rib 222 on the front slide 172 and the groove 288 of the cylindrical rear section 280 of the cannula 6 always maintains the proper alignment of the blade slot 56 of the blade tube 48 with the slot 22 formed in the tubular member 16 of the cannula 6 no matter the axial position of the front slide assembly with respect to the sleeve/cannula assembly so that the cutting blade 24, when the retractable cutting blade assembly 54 is actuated, will project through both slots 56, 22. If desired, the safety piece 180 may now be removed and the hammer 174 may be pivoted by the surgeon to the downward position on the front slide 172 of the surgical instrument 2 against the bias of the hammer return spring 186 and locked into place or held in this position by the surgeon exerting finger pressure on the double wing handle 248 thereof. This causes the distal end of the endoscope 14 to sufficiently engage the retractable cutting blade assembly 54, causing the cutting blade 24 to project outwardly not only from the slot 56 in the blade tube 48 but also the slot 22 of the cannula 6. Even though the angle-cut distal end of the endoscope 14 has moved forward within the blade tube 48 to sufficiently engage the retractable cutting blade assembly 54, it is still in alignment with the viewing window 58 to observe the tissue being severed at the surgical site.

Like the first embodiment of the surgical instrument 2 described previously and shown in FIGS. 1-28L of the drawings, an advantage of this second embodiment of the surgical instrument 2 of the present invention is that it allows the surgeon to extend the cutting blade 24 in any axial position on the front tubular member 16 of the cannula 6 such that the transverse carpal ligament may be severed starting from the distal margin thereof or the proximal margin thereof, or any point in between, since the retraction and extension of the cutting blade 24 may be easily controlled by the surgeon during the surgical procedure.

The surgeon may use this version of the endoscopic instrument 2 during the surgical procedure in several ways. The surgeon may choose to move the cutting blade 24, while still retracted, to a particular position along the axial length of the front tubular member 16 of the cannula 6 so that the blade 24 is in alignment with an anatomical structure at the surgical site that is desired to be severed. The surgeon does this by rotating the sleeve 178 with respect to the cannula 6 and the front slide assembly to the "unlock" position so that the front slide assembly, with the blade tube 48 and the endoscope 14 coupled thereto, may be axially slidably moved with respect to the sleeve/cannula assembly. The hammer 174 is retained in an upright position on the front slide 172 so that the cutting blade 24 remains in a retracted position. During this maneuver, the safety piece 180 may be retained in place on the front slide assembly to prevent the blade 24 from inadvertently being exposed through the cannula slot 22. The surgeon may now remove the safety piece 180 and pivot the hammer 174 rearwardly to a downward position on the front slide 172. The hammer 174, when pivoted to this position, will exert pressure on the scope coupler 176 and move the scope coupler 176 forward on the front slide 172 a predetermined distance against the bias of the hammer return spring 186 so that the tip of the endoscope 14 coupled to the instrument 2 will sufficiently engage the sliding bottom blade housing 138 of the retractable cutting blade assembly 54 within the blade tube 48 to cause the cutting blade 24 to project through the blade tube slot 56 and the cannula slot 22.

The blade 24 is extended through the slot 22 of the cannula 6 and the cutting edge 154, 156 of the blade 24 is moved into contact with the transverse carpal ligament. The transverse carpal ligament is severed by either withdrawing the cutting blade 24 or advancing the cutting blade 24 in either axial direction on the cannula 6 by moving the front slide assembly in a forward direction or rearward direction with respect to the sleeve/cannula assembly and with the hammer 174 in the downward, blade projecting position.

Alternatively, the sleeve 178 may remain in the "lock" position to prevent relative axial movement between the sleeve/cannula assembly and the front slide assembly, and the hammer 174, with the safety piece 180 removed, is pivoted from the upright position to the downward position on the front slide 172. The cutting blade 24 extends from the cannula slot 22, and the cutting edge 156 of the blade 24 is moved into contact with the far margin of the transverse carpal ligament and the transverse carpal ligament is divided by withdrawing the cannula 6 and the surgical instrument 2 towards the entry portal, thereby drawing the cutting edge 156 of the blade 24 through the transverse carpal ligament. The blade 24 may then be retracted back into the cannula 6 when the near margin of the transverse carpal ligament has been reached and severed.

After the transverse carpal ligament has been severed, and with the surgical instrument 2 still maintained at the surgical site, the hammer 174 on the surgical instrument 2 may then be pivoted by the surgeon to the upright position to retract the cutting blade 24 through the cannula slot 22. After the cutting operation, the endoscope 14, still attached to the surgical instrument 2, may view the surgical site through the transparent tubular member 16 of the cannula 6 and the window 58 of the blade tube 48 to visualize the cut edges of the transverse carpal ligament. If any strands of the transverse carpal ligament remain uncut, the blade 24 can then be extended out from the cannula slot 22 again to sever those strands. Alternatively, if the surgical instrument 2 during the cutting procedure is withdrawn towards the entry portal while the cutting edge 156 of the blade 24, extending through the cannula slot 22, is drawn through the transverse carpal ligament, the cutting blade 24 may then be retracted, and the front tubular member 16 of the cannula 6, affixed to the surgical instrument 2, may then be moved back towards the far margin of the transverse carpal ligament through the formed passage, and the optical system of the endoscope 14 may be used to visualize the cut edges of the transverse carpal ligament to determine if any strands or sections of the ligament remain uncut.

The surgical instrument 2 of the present invention permits at all times the visualization of the integrity of the underlying median nerve and tendons attached to the digits. While visualizing the nerves and tendons, release is confirmed by passive manipulation of the digits through their range of motion. The front tubular member 16 of the cannula 6 is then withdrawn and removed from the entry portal. The surgical instrument 2 is then properly discarded as medical waste. The wound is closed and a soft bandage is applied. In some cases, a splint is also applied to immobilize the wrist for up to a week.

Figure 118:
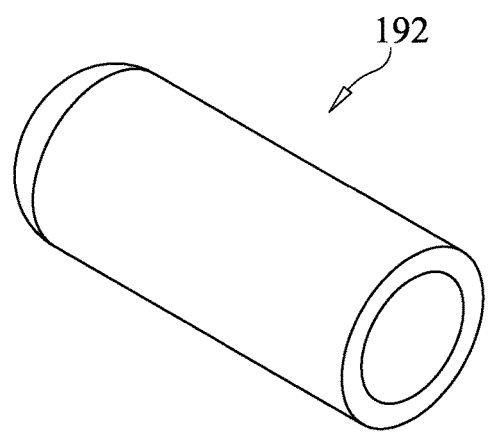
Figure 119:
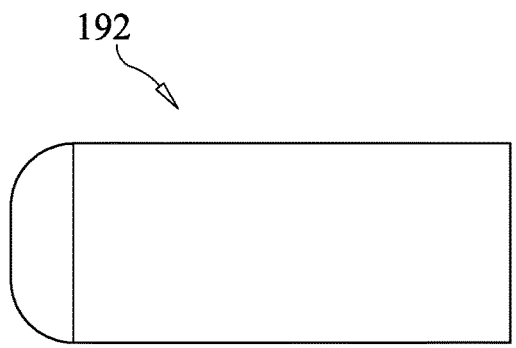
Figure 120:
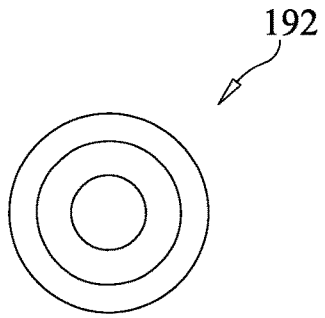
Figure 121:
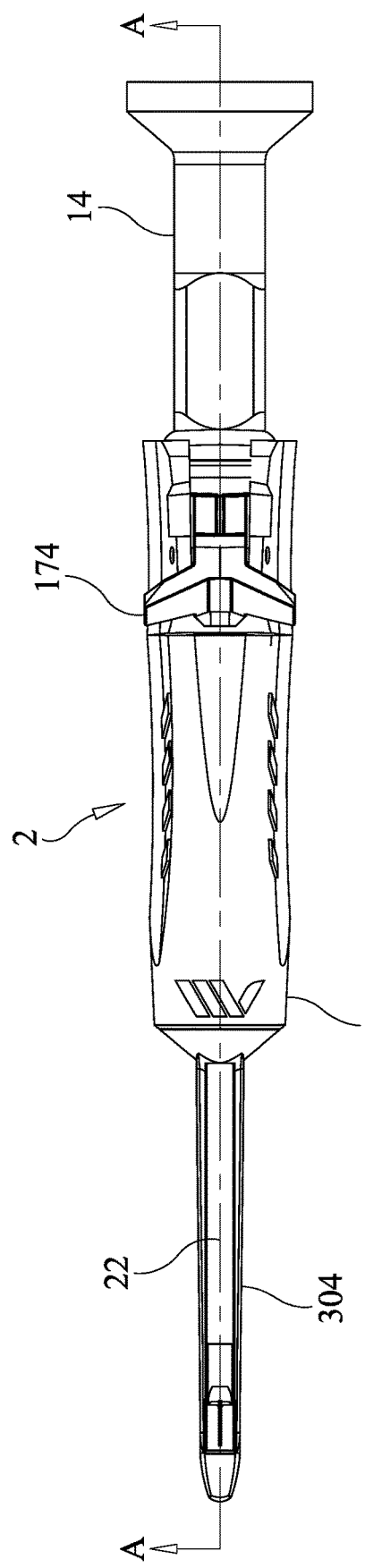

During transport of the surgical instrument 2, or prior to its use, or when the instrument 2 is discarded after a surgical procedure, the end cap 192 (see FIGS. 118-120) is securely fitted onto the distal end portion 26 of the front tubular member 16 of the cannula 6. The axial length of the end cap 192 is preferably chosen to cover a portion of the cannula 6 where the retractable cutting blade assembly 54 within the blade tube 48 resides when the sleeve 178 is in the "lock" position so as to prevent exposure of the cutting blade 24 through the cannula slot 22 should the hammer 174 be inadvertently moved to the blade extended position. As a further precaution, the safety piece 180 should always be installed on the surgical instrument 2 when the instrument 2 is not being used.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An endoscopic surgical instrument, which comprises:
a front slide, the front slide having a rear main body and an elongated, tubular member, the rear main body having an outer side wall defining a hammer receiving opening and an internal bore in communication with the hammer receiving opening, the main body further having a front wall joined to the outer side wall, the elongated, tubular member being joined to the main body at the front wall thereof and extending axially outwardly from the front wall, the elongated, tubular member having a bore extending axially therethrough, the bore of the elongated, tubular member being in communication with the internal bore of the rear main body;
a scope coupler assembly, the scope coupler assembly including a scope coupler and having means for removably mounting an endoscope or arthroscope on the scope coupler, at least a portion of the scope coupler being received by the internal bore of the front slide such that the scope coupler is mounted on the rear main body of the front slide and is reciprocatingly movable within the internal bore of the rear main body;
a hammer, the hammer being pivotally mounted on the rear main body of the front slide, the hammer having a main body, the hammer main body including an upper portion which extends outwardly of the rear main body of the front slide and through the hammer receiving opening formed therein, and a lower portion disposed opposite the upper portion and extending inwardly of the rear main body of the front slide and into the internal bore thereof, the hammer being pivotable on the rear main body of the front slide between a blade retracted position and a blade extended position, the lower portion of the hammer being engageable with the scope coupler such that the scope coupler is in a first, forward position on the front slide when the hammer is in the blade extended position and is in a second, rearward position on the front slide which is different from the first, forward position when the hammer is in the blade retracted position;
a cannula, the cannula having a generally cylindrical rear section and an elongated, slotted tubular member, the rear section of the cannula having an outer side wall defining an interior bore formed in the rear section, and a front wall having an opening formed through the thickness thereof, the slotted tubular member being joined to and extending outwardly from the front wall of the rear section of the cannula, the tubular member including an outer side wall defining a lumen within the tubular member and having a slot formed through the thickness of the outer side wall in communication with the lumen, the slot extending at least partially along an axial length of the tubular member of the cannula, the lumen being in alignment and communication with the opening formed in the front wall of the rear section of the cannula, the cannula being mounted on the front slide such that the tubular member of the front slide is received by the interior bore of the rear section of the cannula;
a sleeve, the sleeve being mounted on the rear section of the cannula and being at least partially rotatable thereon;
a blade tube, the blade tube having a proximal end portion and a distal end portion disposed axially opposite the proximal end portion, the proximal end portion being at least partially received by the bore of the tubular member of the front slide, and the distal end portion of the blade tube being received by the lumen of the tubular member of the cannula, the blade tube having formed therein a bore extending axially thereon and a blade slot formed thereon, the blade tube being positioned within the lumen of the tubular member of the cannula such that the blade slot is in alignment and communication with the axially-extending slot formed on the tubular member of the cannula; and
a retractable cutting blade assembly, the retractable cutting blade assembly being mounted in the internal axial bore of the blade tube in proximity to the distal end portion thereof, the retractable cutting blade assembly having a cutting blade, the cutting blade being positioned to be in alignment with the blade slot formed on the blade tube so as to selectively project outwardly from the blade tube through the blade slot of the blade tube and through the axially-extending slot formed in the tubular member of the cannula and to selectively retract into the bore of the blade tube;
wherein the front slide and blade tube are configured to receive at least a distal viewing end portion of the endoscope or arthroscope such that the distal viewing end portion of the endoscope or arthroscope is selectively engageable with the retractable cutting blade assembly;
wherein, when the hammer on the front slide is in the blade retracted position, the scope coupler is in the second, rearward position on the front slide to prevent the distal viewing end portion of the endoscope or arthroscope coupled to the scope coupler from exerting a blade extending force on the retractable cutting blade assembly, thereby maintaining the cutting blade in a retracted position within the bore of the blade tube; and wherein, when the hammer on the front slide is in the blade extended position, the scope coupler is in the first, forward position on the front slide to allow the distal viewing end portion of the endoscope or arthroscope coupled to the scope coupler to exert the blade extending force on the retractable cutting blade assembly, thereby causing the cutting blade to project outwardly of the blade tube through the blade slot formed therein and outwardly of the tubular member of the cannula through the axially-extending slot formed therein.

2. The endoscopic surgical instrument as defined by claim 1, wherein the scope coupler of the scope coupler assembly includes a main body having a front section and a rear section joined to the front section, at least the front section of the main body of the scope coupler being received by the internal bore of the front slide, the main body having an axial bore formed therethrough and further having formed in the rear section thereof a rear axial opening in communication with the axial bore for receiving a portion of the endoscope or arthroscope therethrough, the rear section of the main body having a side wall, the side wall having an outer surface, the outer surface having a groove formed therein, the outer surface of the side wall of the rear section of the scope coupler further having formed within the groove at least one radially extending opening that communicates with the axial bore formed through the main body of the scope coupler; and wherein the means of the scope coupler assembly for removably mounting the endoscope or arthroscope on the scope coupler includes an O-ring, the O-ring being seated in the groove, and at least one ball bearing, the at least one ball bearing being positioned underneath the O-ring disposed in the groove and is received by the at least one radially extending opening, at least a portion of the at least one ball bearing extending into the axial bore of the scope coupler.

3. The endoscopic surgical instrument as defined by claim 2, wherein the at least one radially extending opening formed in the groove and extending through the thickness of the side wall of the rear section of the main body of the scope coupler includes a portion thereof formed with a diameter which is less than a diameter of the at least one ball bearing received therein so that only the portion of the at least one ball bearing projects into the axial bore of the main body of the scope coupler, the at least one ball bearings being held in place in the at least one opening and biased radially inwardly towards the axial bore of the main body of the scope coupler by the O-ring.

4. The endoscopic surgical instrument as defined by claim 2, wherein the main body of the front slide includes an interior surface which faces the internal bore defined by the main body of the front slide, the interior surface having formed therein oppositely disposed slots; and wherein the front section of the main body of the scope coupler includes opposite lateral side walls, and further includes a pair of axially extending fins protruding outwardly from the opposite lateral side walls, the fins being slidably received by respective oppositely disposed slots formed in the interior surface of the main body of the front slide.

5. The endoscopic surgical instrument as defined by claim 2, wherein the scope coupler includes a strike plate formed as a planar wall affixed to or integrally formed with the main body at the front section thereof and extending perpendicularly to the axis of the scope coupler, the strike plate having a rear bearing surface contactable by the lower portion of the hammer to move the scope coupler in the first, forward position on the front slide when the hammer is pivoted to the blade extended position.

6. The endoscopic surgical instrument as defined by claim 5, wherein the lower portion of the main body of the hammer includes two parallelly extending, spaced apart legs;

wherein the scope coupler includes a knee brace joined to and extending outwardly from the main body of the scope coupler at the front section thereof and the rear bearing surface of the strike plate, the knee brace being provided to strengthen a connection between the strike plate and the main body of the scope coupler; and wherein the spaced apart legs of the lower portion of the main body of the hammer straddle the knee brace of the scope coupler.

7. The endoscopic surgical instrument as defined by claim 1, wherein the sleeve is a generally cylindrical member formed with an outer side wall which defines an open front axial end and an opposite open rear axial end, and an internal bore extending between and being in communication with the open front and rear axial ends of the sleeve, the outer side wall of the sleeve having an interior surface which faces the internal bore of the sleeve; and wherein the cylindrical rear section of the cannula is received by the internal bore of the sleeve through the open front axial end of the sleeve.

8. The endoscopic surgical instrument as defined by claim 7, wherein the outer side wall of the sleeve includes flattened portions disposed substantially diametrically opposite each other, the flattened portions facilitating the grasping of the sleeve, and the at least partial rotation of the sleeve on the cannula, by a user of the surgical instrument.

9. The endoscopic surgical instrument as defined by claim 7, wherein the tubular member of the front slide includes an outer surface, the outer surface including a rib protruding outwardly therefrom and extending axially along at least a portion of an axial length of the tubular member; and wherein the outer side wall of the cylindrical rear section of the cannula includes an interior surface facing the interior bore, the interior surface having formed therein a groove extending at least partially over an axial length of the cylindrical rear section, the groove slidably receiving the guide rib formed on the tubular member of the front slide; and wherein cooperation between the guide rib of the front slide and the groove formed in the cylindrical rear section of the cannula allows relative axial movement between the front slide and the cannula and prevents relative rotational movement between the front slide and the cannula.

10. The endoscopic surgical instrument as defined by claim 9, wherein the guide rib is spaced apart from the front wall of the rear main body of the front slide to define a space therebetween; and wherein the sleeve further includes a lock/unlock protrusion extending radially outwardly from the interior surface of the outer side wall of the sleeve and partially into the internal bore of the sleeve, the sleeve lock/unlock protrusion being disposed in proximity to the open rear axial end of the sleeve; wherein the sleeve is partially rotatable on the cylindrical rear section of the cannula between a lock position and an unlock position;

wherein, when the sleeve is in the lock position, the sleeve lock/unlock protrusion is in alignment with the guide rib on the front slide and resides within the rib space of the tubular member of the front slide to prevent relative axial movement between the front slide and the cannula; and wherein, when the sleeve is rotated on the cylindrical rear section of the cannula from the lock position to the unlock position, the sleeve lock/unlock protrusion is no longer residing in the rib space or in alignment with the guide rib to allow relative axial movement between the front slide and the cannula.

11. The endoscopic surgical instrument as defined by claim 10, wherein the cylindrical rear section of the cannula includes a rear wall, the rear wall having a rear opening formed therein, the rear opening being in communication with the interior bore of the cylindrical rear section of the cannula; and wherein an arcuate slot is formed in the rear wall of the cylindrical rear section of the cannula that surrounds the rear opening of the cannula, the slot receiving the lock/unlock protrusion of the sleeve, the rear wall of the cylindrical rear section of the cannula in which the arcuate slot is formed limiting the rotational movement of the sleeve relative to the cannula to the length of the arcuate slot.

12. The endoscopic surgical instrument as defined by claim 10, which further comprises:

a stop member; and wherein the outer side wall of the cylindrical rear section of the cannula has a slot having a first closed end and an opposite second closed end formed through the thickness thereof, the slot extending axially on the cylindrical rear section at least partially along a longitudinal length thereof, a width of the slot being dimensioned to receive the stop member, the stop member being affixed to the tubular member of the front slide at a position in alignment with the slot, the stop member extending radially outwardly a predetermined distance from the outer surface of the tubular member such that the stop member will not contact the interior surface of the outer side wall of the sleeve so as not to impede rotational movement of the sleeve on the cylindrical rear section of the cannula but will extend outwardly from the front slide into the confines of the slot of the rear section of the cannula, whereby cooperation of the stop member and the slot causes the cannula to remain fixed to the front slide but will allow relative axial movement between the front slide and the cannula when the sleeve is in the unlock position on the cannula, and wherein the stop member can reciprocatingly slide within the slot from the first closed end of the slot to the opposite second closed end of the slot when the front slide and the cannula move axially relative to one another, the stop member residing in the slot limiting the extent to which the cannula and front slide may move relative to one another.

13. The endoscopic surgical instrument as defined by claim 1, wherein the upper portion of the main body of the hammer includes a handle portion which is engageable by a user of the surgical instrument to effect pivotal movement of the hammer between the blade retracted position and the blade extended position.

14. The endoscopic surgical instrument as defined by claim 13, wherein the handle portion of the hammer includes protruding planar members extending angularly in mutually opposite directions.

15. The endoscopic surgical instrument as defined by claim 1, which further comprises a safety piece, the safety piece being receivable in the hammer receiving opening of the rear main body of the front slide and being forcibly removable therefrom, the safety piece, when received by the hammer receiving opening, preventing the hammer from pivoting on the front slide to the blade extended position.

16. The endoscopic surgical instrument as defined by claim 15, wherein the sleeve includes an outer side wall having a first color; and wherein at least a portion of the safety piece has a second color which is distinguishable and different from a color of the outer side wall of the sleeve so that a user of the surgical instrument will recognize whether the safety piece is in place mounted on the surgical instrument to render the instrument inoperable and safe to handle.

17. The endoscopic surgical instrument as defined by claim 15, wherein the safety piece includes a main body having an upper portion and a lower portion disposed opposite the upper portion, and a front wall which faces the hammer when the safety piece is received in the hammer receiving opening of the front slide, the safety piece further including a protrusion projecting outwardly from the front wall of the main body at the upper portion thereof;

wherein the main body of the hammer includes a rear wall and a recess formed in the rear wall, the rear wall of the main body of the hammer facing the front wall of the main body of the safety piece when the safety piece is received by the hammer receiving opening of the front slide; and wherein, when the safety piece is received by the hammer receiving opening of the front slide, the protrusion on the front wall of the safety piece is received by the recess formed in the rear wall of the hammer that faces the front wall of the safety piece, thereby coupling the safety piece to the hammer until the safety piece is forcibly decoupled therefrom and removed from the hammer receiving opening of the front slide.

18. The endoscopic surgical instrument as defined by claim 1, wherein the tubular member of the cannula includes a flattened top wall, the axially-extending slot being formed through the thickness of the flattened top wall and extending axially thereon over at least a portion of the longitudinal length thereof, the axially-extending slot being provided to allow the retractable cutting blade to project therefrom.

19. The endoscopic surgical instrument as defined by claim 1, wherein at least a portion of the tubular member of the cannula is transparent so that the endoscope or arthroscope whose distal end is received by the surgical instrument and which passes through at least a portion of the lumen of the cannula can view through the transparent portion of the cannula tissue or other anatomical features at a surgical site when a surgeon is performing a procedure on a patient using the surgical instrument.

20. The endoscopic surgical instrument as defined by claim 19, wherein the blade tube includes a side wall; and wherein a window is formed in the side wall of the blade tube near the distal end portion thereof, the window being defined by a cutaway portion of the side wall, the window being provided so that the distal viewing end portion of the endoscope or arthroscope received by the bore of the blade tube may view through the window formed in the blade tube and through the transparent portion of the tubular member of the cannula tissue or other anatomical structure of the patient at the surgical site during athe surgical procedure when the distal viewing end portion of the endoscope or arthroscope is positioned in proximity to the window formed in the side wall of the blade tube.

21. The endoscopic surgical instrument as defined by claim 20, wherein the window extends circumferentially on the side wall of the blade tube over about a 180 degree portion thereof.

22. The endoscopic surgical instrument as defined by claim 1, wherein the cannula includes a distal end and a proximal end situated axially opposite the distal end; and
wherein the tubular member is formed with a curved end at the distal end of the cannula to define an obturator thereat so that the cannula, when being positioned at a surgical site, will minimize any injury to tissue with which the cannula comes in contact.

23. The endoscopic surgical instrument as defined by claim 22, wherein the retractable cutting blade positioned at the distal end of the blade tube is disposed proximate to but axially inwardly from the obturator end of the cannula.

24. The endoscopic surgical instrument as defined by claim 1, wherein the distal end of the blade tube is closed.

25. The endoscopic surgical instrument as defined by claim 1, wherein the blade tube includes a side wall; and
wherein the surgical instrument further comprises an alignment ring, the alignment ring being mounted on the side wall of the blade tube and extending radially outwardly therefrom, the proximal end portion of the blade tube and the distal end portion of the blade tube respectively residing on opposite axial sides of the alignment ring, the alignment ring contacting the tubular member of the front slide and being fixedly positioned on the blade tube at a predetermined location on an axial length thereof so that the distal end portion of the blade tube projects axially outwardly from the tubular member of the front slide a predetermined distance so as to be received by and extend through at least a portion of the axial length of the lumen formed in the tubular member of the cannula.

26. The endoscopic surgical instrument as defined by claim 25, wherein the alignment ring includes an outer surface, the outer surface having a flattened portion;
wherein the tubular member of the front slide includes a distal end portion, the distal end portion of the tubular member of the front slide having an inner surface facing the bore of the tubular member, the inner surface having a flattened portion; and
wherein the alignment ring is at least partially received by the bore of the tubular member of the front slide, the flattened portion of the outer surface of the alignment ring being in alignment with and facing the flattened portion of the inner surface of the tubular member of the front slide.

27. The endoscopic surgical instrument as defined by claim 1, wherein the retractable cutting blade assembly positioned in proximity to the distal end portion of the blade tube further includes a top blade housing, a bottom blade housing, an actuator pin, at least one compression spring and a pivot pin;
wherein the top blade housing is fixedly mounted in the bore of the blade tube, the top blade housing having a slot formed through the thickness thereof through which the cutting blade may extend from and retract into, the slot in the top blade housing being positioned to be in alignment with the blade slot formed in the blade tube so that the cutting blade may project from and retract into each of the slot in the top blade housing and the blade slot formed in the blade tube;
wherein the bottom blade housing is slidable reciprocatingly within the bore of the blade tube, the bottom blade housing being movably joined to the top blade housing by the at least one compression spring, the at least one compression spring biasing the bottom blade housing away from the top blade housing, the bottom blade housing having a surface in which is formed a slot, the slot formed in the bottom blade housing being positioned to be in alignment with the slot formed in the top blade housing, the slot formed in the bottom blade housing at least partially receiving a portion of the cutting blade, the bottom blade housing being engageable by the distal viewing end portion of the endoscope or arthroscope when the distal viewing end portion thereof is received by the bore of the blade tube;
wherein the pivot pin passes transversely through the bottom blade housing and through the thickness of the cutting blade to allow the cutting blade to pivot thereon and within the slot of the bottom blade housing;
wherein the cutting blade has an arcuate slot formed through the thickness thereof, the actuator pin passing transversely through the top blade housing and through the slot formed therein and through the arcuate slot formed through the thickness of the cutting blade, the arcuate slot having a first end and an opposite second end;
wherein the actuator pin received by the arcuate slot formed in the cutting blade causes the cutting blade to move within the slot of the top blade housing between an extended position when the actuator pin is located near the first end of the arcuate slot and a retracted position when the actuator pin is located near the second end of the arcuate slot; and
wherein, when pressure is exerted on the bottom blade housing by the distal viewing end portion of the endoscope or arthroscope received by the bore of the blade tube and engaging the retractable cutting blade assembly and to compress the spring thereof, the bottom blade housing moves towards the top blade housing and causes the cutting blade to pivot on the pivot pin on the bottom blade housing, the cutting blade being guided in its movement by the actuator pin situated within the arcuate slot formed therein, the movement of the bottom blade housing towards the top blade housing causing the cutting blade to move from a retracted state, with the actuator pin being situated near the first end of the arcuate slot formed in the cutting blade, to an extended state, with the actuator pin being located near the second end of the arcuate slot formed in the cutting blade such that the cutting blade extends outwardly of the slot formed in the top blade housing and outwardly of the aligned blade slot formed in the blade tube; and
wherein, when the distal viewing end portion of the endoscope or arthroscope is moved in the bore of blade tube in a direction away from the distal end portion of the blade tube, the compression spring relaxes and causes the bottom blade housing to move away from the top blade housing, resulting in the cutting blade being retracted within the slot formed in the top blade housing and from the slot formed in the blade tube and caused by the blade pivoting on the pivot pin and being affixed to the slidable bottom blade housing, the actuator pin being situated near the second end of the arcuate slot formed in the cutting blade.

28. The endoscopic surgical instrument as defined by claim 1, wherein the cutting blade includes a forward facing sharpened edge and a rearward facing sharpened edge.

* * * * *